(12) United States Patent
Andrews et al.

(10) Patent No.: US 9,186,340 B2
(45) Date of Patent: *Nov. 17, 2015

(54) ISCHEMIA/REPERFUSION PROTECTION COMPOSITIONS AND METHODS OF USING

(75) Inventors: Matthew T. Andrews, Duluth, MN (US); Lester R. Drewes, Duluth, MN (US); Greg Beilman, Richfield, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 1218 days.

This patent is subject to a terminal disclaimer.

(21) Appl. No.: 12/595,586

(22) PCT Filed: Apr. 11, 2008

(86) PCT No.: PCT/US2008/060100
§ 371 (c)(1),
(2), (4) Date: Apr. 1, 2010

(87) PCT Pub. No.: WO2008/128095
PCT Pub. Date: Oct. 23, 2008

(65) Prior Publication Data
US 2010/0197758 A1     Aug. 5, 2010

Related U.S. Application Data

(60) Provisional application No. 60/911,460, filed on Apr. 12, 2007, provisional application No. 61/026,321, filed on Feb. 5, 2008.

(51) Int. Cl.
| | | |
|---|---|---|
| *A61K 31/405* | (2006.01) | |
| *A61K 31/185* | (2006.01) | |
| *A61K 31/19* | (2006.01) | |
| *A61K 9/00* | (2006.01) | |
| *A61K 31/12* | (2006.01) | |
| *A61K 31/404* | (2006.01) | |
| *A61K 31/4045* | (2006.01) | |

(52) U.S. Cl.
CPC .............. *A61K 31/19* (2013.01); *A61K 9/0019* (2013.01); *A61K 31/12* (2013.01); *A61K 31/404* (2013.01); *A61K 31/4045* (2013.01)

(58) Field of Classification Search
CPC ... A61K 31/12; A61K 31/19; A61K 31/4045; A61K 2300/00
See application file for complete search history.

(56) References Cited

U.S. PATENT DOCUMENTS

| | | | |
|---|---|---|---|
| 4,298,601 A | 11/1981 | Howard | |
| 4,663,166 A | 5/1987 | Veech | |
| 4,970,143 A | 11/1990 | Gidoux et al. | |
| 5,049,388 A | 9/1991 | Knight et al. | |
| 5,098,409 A | 3/1992 | Stock | |
| 5,100,677 A | 3/1992 | Veech | |
| 5,141,674 A | 8/1992 | Leigh | |
| 5,257,985 A | 11/1993 | Puhl | |
| 5,700,828 A | 12/1997 | Federowicz et al. | |
| 5,719,119 A | 2/1998 | Veech | |
| 5,814,663 A | 9/1998 | Cook et al. | |
| 5,853,388 A | 12/1998 | Semel | |
| 6,232,345 B1 | 5/2001 | Hiraide et al. | |
| 6,316,038 B1 | 11/2001 | Veech | |
| 6,323,237 B1 | 11/2001 | Veech | |
| 6,329,343 B1 | 12/2001 | Leung et al. | |
| 6,353,015 B1 | 3/2002 | Oxenkrug et al. | |
| 6,890,896 B1 | 5/2005 | Shashoua | |
| 7,083,572 B2 | 8/2006 | Unger et al. | |
| 7,097,827 B2 | 8/2006 | Platz et al. | |
| 2001/0014696 A1 | 8/2001 | Veech | |
| 2001/0041736 A1 | 11/2001 | Veech | |
| 2001/0051652 A1 | 12/2001 | Nishino et al. | |
| 2002/0091080 A1 | 7/2002 | Fruebis et al. | |
| 2002/0168430 A1 | 11/2002 | Heeg et al. | |
| 2003/0143530 A1 | 7/2003 | Klepp et al. | |
| 2004/0171671 A1 | 9/2004 | Veech | |
| 2004/0223963 A1 | 11/2004 | Cheung et al. | |
| 2004/0235960 A1 | 11/2004 | Burns et al. | |
| 2005/0129783 A1 | 6/2005 | McCleary et al. | |
| 2006/0280721 A1 | 12/2006 | Veech et al. | |
| 2007/0299135 A1 | 12/2007 | Martin et al. | |
| 2011/0111049 A1 | 5/2011 | Andrews et al. | |

FOREIGN PATENT DOCUMENTS

| | | |
|---|---|---|
| WO | WO 91/02535 | 3/1991 |
| WO | WO 98/41201 | 9/1998 |
| WO | WO 2004/047871 | 6/2004 |
| WO | WO 2004/096118 A2 | 11/2004 |
| WO | WO 2004/108740 A2 | 12/2004 |

(Continued)

OTHER PUBLICATIONS

"Novel Approaches to Treatment of Shock," *Fluid Resuscitation: State of the Science for Treating Combat Casualties and Civilian Injuries*, 1999, Committee on Fluid Resuscitation for Combat Casualties, Institute of Medicine.

Andrews et al., "Low-temperature carbon utilization is regulated by novel gene activity in the heart of a hibernating mammal," *Proc. Natl. Acad. Sci. USA*, 1998, 95(14):8392-8397.

Andrews, "Advances in molecular biology of hibernation in mammals," *BioEssays*, 2007, 29:431-440.

(Continued)

*Primary Examiner* — Shobha Kantamneni

(74) *Attorney, Agent, or Firm* — Fish & Richardson P.C.

(57) ABSTRACT

The invention provides for ischemia/reperfusion protection compositions having one or more ketone bodies and melatonin. The invention also provides for methods of using such compositions to reduce or prevent ischemia/reperfusion injury due to blood loss, stroke or cardiopulmonary arrest or surgery.

16 Claims, 32 Drawing Sheets

(56) References Cited

FOREIGN PATENT DOCUMENTS

| WO | WO 2005/107724 | 11/2005 |
|---|---|---|
| WO | WO 2005/107875 | 11/2005 |
| WO | WO 2006/012490 | 2/2006 |
| WO | WO 2006/020137 | 2/2006 |
| WO | WO 2006/020179 | 2/2006 |
| WO | WO 2006/034361 | 3/2006 |
| WO | WO 2006/098767 | 9/2006 |

OTHER PUBLICATIONS

Andrews et al., "Adaptive mechanisms regulate preferred utilization of ketones in the heart and brain of a hibernating mammal during arousal from torpor," *Am J Physiol Regul Integr Comp Physiol.*, 2009, 296: R383-R393, First published Dec. 3, 2008.

Bauer et al., "Expression of a chimeric retroviral-lipase mRNA confers enhanced lipolysis in a hibernating mammal," *Am. J. Physiol. Regul. Integr. Comp. Physiol.*, 2001, 281(4):R1186-R1192.

Beilman et al., "Near-infrared spectroscopy measurement of regional tissue oxyhemoglobin saturation during hemorrhagic shock," *Shock*, 1999, 12(3):196-200.

Broer et al., "Characterization of the monocarboxylate transporter 1 expressed in *Xenopus laevis* oocytes by changes in cytosolic pH," *Biochem. J.*, 1998, 333(Pt 1):167-174.

Buck et al., "Coordinate expression of the PDK4 gene: a means of regulating fuel selection in a hibernating mammal," *Physiol. Genomics*, 2002, 8(1):5-13.

Carey et al., "Mammalian hibernation: cellular and molecular responses to depressed metabolism and low temperature," *Physiol. Rev.*, 2003, 83(4):1153-1181.

Carpenter and Halestrap, "The kinetics, substrate and inhibitor specificity of the lactate transporter of Ehrlich-Lettre tumour cells studied with the intracellular pH indicator BCECF," *Biochem. J.*, 1994, 304(Pt 3):751-760.

Chen et al., "Melatonin attenuates the postischemic increase in blood-brain barrier permeability and decreases hemorrhagic transformation of tissue-plasminogen activator therapy following ischemic stroke in mice," *J. Pineal Res.*, 2006, 40:242-250.

Chen et al., "Melatonin decreases neurovascular oxidative/nitrosative damage and protects against early increases in the blood-brain barrier permeability after transient focal cerebral ischemia in mice," *J. Pineal Res.*, 2006, 41:175-182.

Clinkenbeard et al., "Molecular and catalytic properties of cytosolic acetoacetyl coenzyme A thiolase from avian liver," *J. Biol. Chem.*, 1973, 248(7):2275-2284.

Cohn et al., "Tissue oxygen saturation predicts the development of organ dysfunction during traumatic shock resuscitation," *J. Trauma*, 2007, 62(1):44-54.

D'Alecy et al., "β-hydroxybutyrate and response to hypoxia in the ground squirrel, Spermophilus tndecimlmeatus," *Comp. Biochem. Physiol. B*, 1990, 96(1):189-193.

Dirnagl et al., "Pathobiology of ischaemic stroke: an integrated view," *Trends Neurosci.*, 1999, 22(9):391-397.

Eastridge et al., "Hypotension begins at 110 mm Hg: redefining "hypotension" with data," *J. Trauma*, 2007, 63:291-299.

Editorial Note, "Melatonin as an antioxidant: physiology versus pharmacology," *J. Pineal Res.*, 2005, 39:215-216.

Eiger et al., "Hypoxic tolerance enhanced by β-hydroxybutyrate-glucagon in the mouse," *Stroke*, 1980, 11(5):513-517.

Englehart and Schreiber, "Measurement of acid-base resuscitation endpoints: lactate, base deficit, bicarbonate or what," *Curr. Opin. Crit. Care*, 2006, 12:569-574.

Forder et al., "Dissociation of mitochondrial and contractile function after global hypothermic ischemia: effects of -hydroxybutyrate," *Circulation*, 1990, 82:Abstract 3006.

Gerhart et al., "Expression of monocarboxylate transporter MCT1 by brain endothelium and glia in adult and suckling rats," *Am. J. Physiol.*, 1997, 273(1 Pt 1):E207-E213.

Gerhart et al., "Expression of the monocarboxylate transporter MCT2 by rat brain glia," *Glia*, 1998, 22(3):272-281.

Green et al., "Wild type and mutant human heart (R)-3-hydroxybutyrate dehydrogenase expressed in insect cells," *Biochemistry*, 1996, 35(25):8158-8165.

Hall et al., "Ketone body kinetics in humans: the effects of insulin-dependent diabetes, obesity, and starvation," *J. Lipid Res.*, 1984, 25(11):1184-1194.

Henry et al., "Brain energy metabolism and neurotransmission at near-freezing temperatures: An in vivo 1H MRS study of a hibernating mammal," *J. Neurochem.*, 2007, 101(6):1505-1515.

Honda et al., "Down-regulation of cholesterol biosynthesis in sitosterolemia: diminished activities of acetoacetyl-CoA thiolase, 3-hydroxy-3-methylglutaryl-CoA synthase, reductase, squalene synthase, and 7-dehydrocholesterol delta7-reductase in liver and mononuclear leukocytes," *J. Lipid Res.*, 1998, 39(1):44-50.

Jackson and Halestrap, "The kinetics, substrate, and inhibitor specificity of the monocarboxylate (lactate) transporter of rat liver cells determined using the fluorescent intracellular pH indicator, 2',7'-bis(carboxyethyl)-5(6)-carboxyfluorescein," *J. Biol. Chem.*, 1996, 271(2):861-868.

Kabine et al., "Hibernation impact on the catalytic activities of the mitochondrial D-3-hydroxybutyrate dehydrogenase in liver and brain tissues of jerboa (*Jaculus orientalis*)," *BMC Biochem.*, 2003, 4(1):11.

Kirsch and D'Alecy, "Effect of altered availability of energy-yielding substrates upon survival from hypoxia in mice," *Stroke*, 1979, 10(3):288-291.

Kirsch and D'Alecy, "Hypoxia induced preferential ketone utilization by rat brain slices," *Stroke*, 1984, 15(2):319-323.

Klein, "Hibernation strategies to improve recovery from hemorrhagic shock," 2007, thesis submitted to the faculty of the graduate school of the University of Minnesota.

Klein et al., Small-volume d-β-hydroxybutyrate solution infusion increases survivability of lethal hemorrhagic shock in rats, Shock, 2010, 34(6):565-572.

Koehler-Stec et al., "Monocarboxylate transporter expression in mouse brain," *Am. J. Physiol.*, 1998, 275(3 Pt 1):E516-E524.

Krilowicz, "Ketone body metabolism in a ground squirrel during hibernation and fasting," *Am. J. Physiol.*, 1985, 249(4 Pt 2):R462-R470.

Lavau et al., "Ketone metabolism in brain slices from rats with diet induced hyperketonemia," *J. Nutr.*, 1978, 108(4):621-639.

Leino et al., "Diet-induced ketosis increases monocarboxylate transporter (MCT1) levels in rat brain," *Neurochem. Int.*, 2001, 38(6):519-527.

Leino et al., "Monocarboxylate transporter (MCT1) abundance in brains of suckling and adult rats: a quantitative electron microscopic immunogold study," *Brain Res. Dev. Brain Res.*, 1999, 113(1-2):47-54.

Lipski et al., "Neuroprotective potential of ceftriaxone in in vitro models of stroke," *Neuroscience*, 2007, 146(2):617-629.

Maldonado et al., "The potential of melatonin in reducing morbidity-mortality after craniocerebral trauma," *J. Pineal Res.*, 2007, 42:1-11.

Masuda et al., "D-β-Hydroxybutyrate is Neuroprotective Against Hypoxia in Serum-free Hippocampal Primary Cultures," *J. Neurosci. Res.*, 2005, 80:501-509.

Mathes et al., "Melatonin pretreatment improves liver function and hepatic perfusion after hemorrhagic shock," *Shock*, 2008, 29(1):112-118.

Mattson and Drewes, "Detection of Endothelial Proteins by Western Blotting in Methods in Molecular Biology," *The Blood Brain Barrier: Biology and Research Protocols*, S. Nag, (ed.), 2003, pp. 479-487.

Maus et al., "Pyruvate and lactate protect striatal neurons against N-methyl-D-aspartate-induced neurotoxicity," *Eur. J. Neurosci.*, 1999, 11(9):3215-3224.

Middleton, "The oxoacyl-coenzyme A thiolases of animal tissues," *Biochem. J.*, 1973, 132(4):717-730.

Mulier et al., "Hibernation-based therapy in a porcine model of hemorrhagic shock results in improved survival," Presented at 2010 Society of Critical Care Medicine's 39th Critical Care Congress, Miami Beach FL, Jan. 2010.

(56) References Cited

OTHER PUBLICATIONS

Mulier et al., "Ringer's ethyl pyruvate in hemorrhagic shock and resuscitation does not improve early hemodynamics or tissue energetics," *Shock*, 2005, 23(3):248-252.

Myers et al., "Noninvasive method for measuring local hemoglobin oxygen saturation in tissue using wide gap second derivative near-infrared spectroscopy," *J. Biomed. Opt.*, 2005, 10(3):1-18.

Nehlig and Pereira De Vasconcelos, "Glucose and ketone body utilization by the brain of neonatal rats," *Progress Neurobiol.*, 1993, 40(2):163-221.

Page et al., "Activities of enzymes of ketone-body utilization in brain and other tissues of suckling rats," *Biochem. J.*, 1971, 121(1):49-53.

Paller et al., "Free radical scavengers in mercuric chloride-induced acute renal failure in the rat," *J. Lab. Clin. Med.*, 1985, 105(4):459-463.

Pierre et al., "MCT2 is a major neuronal monocarboxylate transporter in the adult mouse brain," *J. Cereb. Blood Flow Metab.*, 2002, 22(5):586-595.

Pull and McIlwain, "3-Hydroxybutyrate dehydrogenase of rat brain on dietary change and during maturation," *J. Neurochem.*, 1971, 18(6):1163-1165.

Puyana and Pinsky, "Searching for non-invasive markers of tissue hypoxia," *Crit. Care*, 2007, 11:116-117.

Reiter and Tan, "Melatonin: a novel protective agent against oxidative injury of the ischemic/reperfused heart," *Cardiovascular Res.*, 2003, 58:10-19.

Reiter et al., "Free radical-mediated molecular damage; mechanisms for the protective actions of melatonin in the central nervous system," Neuroprotective Agents, 5th Int'l Conf., *Annals NY Acad. Sci.*, 2001, 939:200.

Rising and D'Alecy, "Hypoxia-induced increases in hypoxic tolerance augmented by $\beta$-hydroxybutyrate in mice," *Stroke*, 1989, 20(9):1219-1225.

Robinson and Williamson, "Physiological roles of ketone bodies as substrates and signals in mammalian tissues," *Physiol. Rev.*, 1980, 60(1):143-187.

Rothstein et al., "$\beta$-lactam antibiotics offer neuroprotection by increasing glutamate transporter expression," *Nature*, 2005, 433(7021):73-77.

Russeth et al., "Identification of proteins from non-model organisms using mass spectometry: Application to a hibernating mammal," *J. Proteome Res.*, 2006, 5(4):829-839.

Schmelzer et al., "A comparison of central venous and arterial base deficit as a predictor of survival in acute trauma," *Am. J. Emerg. Med.*, 2008, 26:119-123.

Seifman et al., "Endogenous melatonin increases in cerebrospinal fluid of patients after severe traumatic brain injury and correlates with oxidative stress and metabolic disarray," *Journal of Cerebral Blood Flow & Metabolism*, 2008, 28:684-696.

Sinha et al., "Effect of melatonin on ischemia reperfusion injury induced by middle cerebral artery occlusion in rats," *Eur. J. Pharmacol.*, 2001, 428:185-192.

Skarda et al., "Comparison of prolonged hypotensive and normotensive resuscitation strategies in a porcine model of hemorrhagic shock," *J. Am. Coll. Surg.*, 2006, 203(3S):S32-S33.

Skarda et al., "Increased poly(ADP-ribose) polymerase activity during porcine hemorrhagic shock is transient and predictive of mortality," *Resuscitation*, 2007, 75(1):135-144.

Smith et al., "KTX 0101: a powerful metabolic approach to cytoprotection in major surgery and neurological disorders," *CNS Drug Rev.*, 2005, 11(2):113-140.

Squire et al., "Pancreatic triacylglycerol lipase in a hibernating mammal. II. Cold-adapted function and differential expression," *Physiol. Genomics*, 2003, 16(1):131-140.

Srere et al., "Central role for differential gene expression in mammalian hibernation," *Proc. Natl. Acad. Sci. USA*, 1992, 89(15):7119-7123.

Suzuki et al., "Effect of $\beta$-hydroxybutyrate, a cerebral function improving agent, on cerebral hypoxia, anoxia and ischemia in mice and rats," *Jpn. J. Pharmacol.*, 2001, 87(2):143-150.

Suzuki et al., "$\beta$-hydroxybutyrate, a cerebral function improving agent, protects rat brain against ischemic damage caused by permanent and transient focal cerebral ischemia," *Jpn. J. Pharmacol.*, 2002, 89(1):36-43.

Tan et al., "Physiological ischemia/reperfusion phenomena and their relation to endogenous melatonin production," *Endocrine*, 2005, 27:149-157.

Taylor et al., "Phosphomonoesters predict early mortality in porcine hemorrhagic shock," *J. Trauma*, 2004, 56(2):251-258.

Taylor et al., "Tissue Energetics As Measured by Nuclear Magnetic Resonance Spectroscopy During Hemorrhagic Shock," *Shock*, 2004, 21(1):58-64.

Taylor et al., "Use of near-infrared spectroscopy in early determination of irreversible hemorrhagic shock," *J. Trauma*, 2005, 58(6):1119-1125.

Tildon et al., "Coenzyme A transferase activity in rat brain," *Biochem. Biophys. Res. Commun.*, 1971, 43(1):225-231.

Tisherman, "Suspended animation for resuscitation from exsanguinating hemorrhage," *Crit Care Med.*, 2004, 32(2) (Suppl.):S46-S50.

Van Der Auwera et al., "A ketogenic diet reduces amyloid $\beta$ 40 and 42 in a mouse model of Alzheimer's disease," *Nutrition and Metabolism*, 2005, 2:28-35.

Vanitallie and Nufert, "Ketones: metabolism's ugly duckling," *Nutr. Rev.*, 2003, 61(10):327-341.

Veech et al., "Ketone bodies, potential therapeutic uses," *IUBMB Life*, 2001, 51(4):241-247.

Wichmann et al., "Melatonin adminstration attenuates depressed immune functions after trauma-hemorrhage," *J. Surgical Res.*, 1996, 63:256-262.

Williamson et al., "Activities of enzymes involved in acetoacetate utilization in adult mammalian tissues," *Biochem J.*, 1971, 121(1):41-47.

Zenker et al., "Thresholded area over the curve of spectrometric tissue oxygen saturation as an indicator of volume resuscitability in porcine hemorrhagic shock," *J. Trauma*, 2007, 63:573-580.

Zhang et al., "Developmental regulation of D-beta-hydroxybutyrate dehydrogenase in rat liver and brain," *FEBS Lett.*, 1989, 256(1-2):71-74.

Authorized Officer Lee W. Young, PCT/US08/60100, International Search Report and Written Opinion of the International Searching Authority, mailed Jul. 14, 2008, 6 pages.

"Cool Hibernators Scientist Becomes Surgeon to Probe Squirrel for Medical Solutions" [online] ABCNEWS.com, [retrieved on Oct. 14, 2003]. Retrieved from the Internet: <URL: http://abcnews.go.com/sections/scitech/US/squirrelsurgery031013.html>, 3 pages.

Flamm et al., "Free Radicals in cerebral ischemia," *Stroke*, 1978, 9:455-477.

Iso et al., "Linoleic acid, other fatty acids, and the risk of stroke," *Stroke*, 2002, 23:2086-2093.

King et al., "Free fatty acids, but not ketone bodies, protect diabetic rat hearts during low-flow ischemia," *Am. J. Physiol. Heart Circ. Physiol.*, 2001, 280:H1173-H1181.

Oliver et al., "Linoleic acid, antioxicants and coronary heart disease," *Cardiovascular Dysfunction*, 1990, 18:1049-1051.

Schmickle, "Feeling like you want to hibernate? Scientists say its in your genes," Star Tribune, 2003, [retrieved on Oct. 14, 2003]. Retrieved from the Internet: <URL: http://www.startribune.com/stories/462/4150245.html>, 4 pages.

International Preliminary Report on Patentability for PCT/US2008/060100 mailed Oct. 22, 2009, 7 pages.

Supplementary European Search Report, EP 08 74 5661, completed Aug. 31, 2011, 8 pages.

ISCHEMIA/REPERFUSION PROTECTION COMPOSITIONS AND METHODS OF USING

CROSS-REFERENCE TO RELATED APPLICATIONS

This application is a National Stage application under 35 U.S.C. §371 and claims benefit under 35 U.S.C. §119(a) of International Application No. PCT/US2008/060100 having an International Filing Date of Apr. 11, 2008, which claims priority under 35 U.S.C. §119(e) to U.S. Application Nos. 60/911,460 filed Apr. 12, 2007 and 61/026,321 filed Feb. 5, 2008, the disclosures of which are incorporated herein in their entirety.

FEDERALLY SPONSORED RESEARCH OR DEVELOPMENT

The U.S. Government has certain rights in this invention pursuant to Grant Nos. W911NF-05-1-0432 and W911NF-06-1-0088 awarded by the Defense Advanced Research Projects Agency (DARPA).

TECHNICAL FIELD

This invention relates to ischemia damage and reperfusion injury, and more particularly to compositions and methods for treating or preventing injury and damage due to ischemia and/or reperfusion. Ischemia and/or reperfusion injury can result from, for example, hemorrhagic shock.

BACKGROUND

Ischemia generally is a restriction in blood supply, with resultant damage or dysfunction of tissue. Ischemia refers to the absolute or relative shortage of blood supply to an organ. Relative shortage of blood supply means a mismatch of blood supply (oxygen delivery) and the need for adequate oxygenation of tissue.

Reperfusion injury refers to the damage caused to tissue when blood supply returns to the tissue after a period of ischemia. The absence of oxygen and nutrients from blood creates a condition in which the restoration of circulation results in inflammation and oxidative or peroxidative damage.

SUMMARY

One or more ketone bodies and melatonin can be administered to an individual to protect the individual from ischemic damage and/or reperfusion injury.

In one aspect, the invention provides an ischemia/reperfusion protection composition. An ischemia/reperfusion protection composition as disclosed herein comprises or consists essentially of one or more ketone bodies and melatonin. The one or more ketone bodies can be, for example, D-beta-hydroxybutyrate or a pharmaceutically acceptable salt thereof (e.g., Na-D-beta hydroxybutyrate), acetoacetate or a pharmaceutically acceptable salt thereof, or D-beta hydroxybutyrate and acetoacetate in combination. Melatonin can be, for example, 5-methoxy-N-acetyltryptamine. In some embodiments, the composition is substantially free of inorganic anions.

In some embodiments, an ischemia/reperfusion protection composition is a liquid composition. When formulated as a liquid, an ischemia/reperfusion protection composition can have from about 0.1 M to about 8 M of ketone bodies and from about 4 μM to about 150 mM of melatonin. In one particular embodiment, an ischemia/reperfusion protection composition can have about 4 M Na-D-beta-hydroxybutyrate and about 43 mM melatonin. In some embodiments, an ischemia/reperfusion protection composition is substantially free of $Cl^-$. In certain embodiments of a liquid composition, the solvent is water. In some embodiments, a liquid composition includes a solubilizer (e.g., DMSO) and/or a stabilizer.

In other embodiments, an ischemia/reperfusion protection composition is a dry powder composition. When formulated as a dry powder, an ischemia/reperfusion protection composition can have a mole to mole ratio of ketone bodies to melatonin of about 100 to 1.

Such ischemia/reperfusion protection compositions can further include one or more antibiotics, one or more free fatty acids, one or more analgesics, one or more hormones, one or more metabolites, one or more metabolic pathway molecules, and/or one or more compounds that alter cellular metabolism (e.g., polypeptides, antisense or siRNA molecules, drugs, or small molecules).

In one aspect, the invention provides an article of manufacture that includes an ischemia/reperfusion protection composition. In one embodiment, the article of manufacture can be an IV bag containing an ischemia/reperfusion protection composition (e.g., a liquid formulation or a dry powder formulation). In another embodiment, an article of manufacture can include a first and a second vessel, wherein the first vessel can contain an ischemia/reperfusion protection composition and the second vessel can contain a solvent. In such an embodiment, the article of manufacture can be configured such that the solvent from the second vessel can be controllably placed into contact with the composition in the first vessel. In another embodiment, an article of manufacture includes a syringe barrel that contains an ischemia/reperfusion protection composition. In yet another embodiment, an article of manufacture can include packaging material and an ischemia/reperfusion protection composition, wherein the packaging material can include a label or package insert having instructions for treating an individual who is experiencing or has experienced blood loss, who is experiencing or has experienced a stroke, or who is going to undergo or is undergoing a medical procedure (e.g., surgery).

In another aspect, the invention provides methods for treating an individual who is experiencing or has experienced blood loss. Such methods comprise administering one or more ketone bodies and melatonin to the individual. In some embodiments, the one or more ketone bodies and melatonin are administered together in a single composition. In certain embodiments, the individual in need of treatment has StO2 levels that are less than 75%. Typically, the administering step results in the individuals StO2 levels returning to greater than 75%, which is indicative of the individual having been treated. In certain embodiments, the individual in need of treatment has lactate levels that are greater than 2.1 mg/dl. Typically, the administering step results in the individuals lactate levels returning to less than 2.1 mg/dl, which is indicative of the individual having been treated. Generally, the administering step prevents the base deficit of the individual from reaching 6 mEq/L.

In certain embodiments, the individual is experiencing or has experienced a major hemorrhagic event (e.g., the individual has lost a blood volume of at least about 10%, at least about 20%, at least about 30%, at least about 40%, at least about 50%, or at least about 60%). In some embodiments, the blood loss in the individual results in a systolic blood pressure of about 70 mm Hg (e.g., 65 mm Hg, 60 mm Hg) or less. In certain embodiments, the one or more ketone bodies are administered to the individual in an amount sufficient to achieve a concentration in the blood of about 3 mM to about 15 mM, and the melatonin is administered to the individual in an amount sufficient to achieve a concentration in the blood of about 20 µM to about 150 µM. In certain embodiments, the one or more ketone bodies and melatonin are administered at a volume of about 0.3 to about 2 milliliters (mls) per kilogram (kg) of weight of the individual. In certain embodiments, the one or more ketone bodies and melatonin are administered at a volume of about 0.3 to about 2 mls per kg of weight of the individual per hour. In certain embodiments, the one or more ketone bodies and melatonin are administered at a volume of about 0.3 to 2 mls per kg of weight of the individual followed by administration of the one or more ketone bodies and melatonin at a volume of about 0.3 to 2 mls per kg body weight of the individual per hour. Representative routes of administration of the one or more ketone bodies and melatonin are intravenously and intraosseously.

In another aspect, the invention provides a method for treating an individual whose StO2 levels are less than 75% and/or who has a base deficit level of greater than 6 mEq/L, comprising identifying such an individual whose StO2 levels are less than 75% or whose base deficit level of greater than 6 mEq/L; and administering one or more ketone bodies and melatonin to the individual.

In still another aspect, the invention provides methods of protecting an individual from ischemic damage or reperfusion injury. Such methods generally include administering one or more ketone bodies and melatonin to the individual. Representative individuals include those who have had a stroke or are at risk of having a stroke, those who are going to undergo surgery (e.g., neurosurgery). In some embodiments, the one or more ketone bodies and the melatonin are administered in an amount of 1 ml per kg of weight of the individual. In certain embodiments, such administration can be followed by a slow infusion of one or more ketone bodies and melatonin.

In yet another aspect, the invention provides methods of treating an organ prior to harvesting the organ from an organ donor. Such methods generally include administering one or more ketone bodies and melatonin to the organ donor (e.g., intravenously). By way of example, the one or more ketone bodies and melatonin can be administered to an organ donor in an amount of at least about 1 ml per kg of weight of the organ donor. In certain instances, the organ donor is in a persistent vegetative state.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references or reference material mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION

Figure 1:
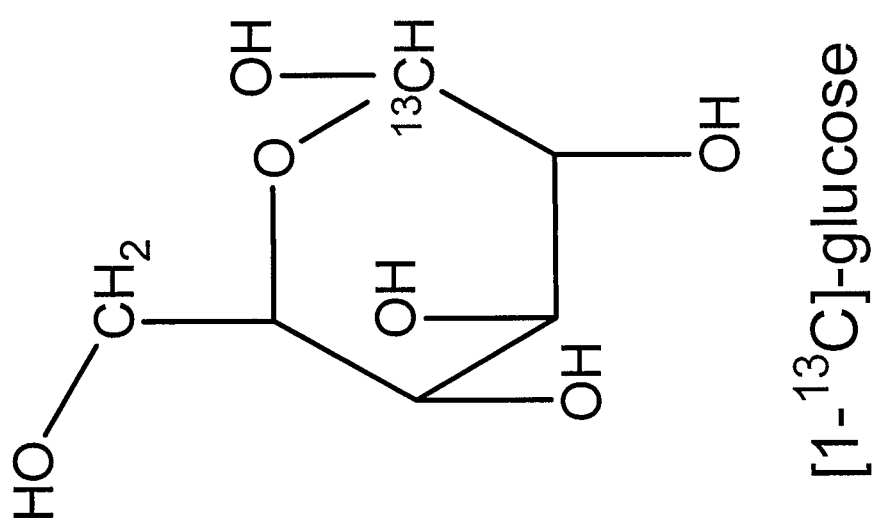
FIG. 1 shows the structure of [1-$^{13}$C] glucose.

One or more ketone bodies and melatonin can be administered to an individual to protect the individual from ischemic damage and/or reperfusion injury. One or more ketone bodies and melatonin can be administered to an individual who is experiencing or has experienced blood loss, is having or has had a stroke or a cardiopulmonary arrest, or is about to undergo or is undergoing a procedure such as surgery. In addition, one or more ketone bodies and melatonin can be administered to an organ donor before harvest so as to thoroughly perfuse the tissue or organ prior to harvest.

Ischemia/Reperfusion Protection Compositions

This disclosure provides for compositions that include one or more ketone bodies and melatonin. These compositions are useful ischemia/reperfusion protection fluids that can protect tissues, organs and, hence, individuals from significant trauma. The compositions disclosed herein can include one or more ketone bodies and melatonin, and can include other constituents such as, for example, therapeutic compounds, some of which are described below. The compositions disclosed herein can "consist essentially of" one or more ketone bodies and melatonin, meaning that such compositions are predominantly one or more ketone bodies and melatonin, but may contain other components present in the composition that do not substantially or materially diminish the ischemic/reperfusion protection characteristics of the composition.

"Ketone bodies" as used herein refer to beta-hydroxybutyrate or acetoacetate (or physiologically acceptable salts of beta-hydroxybutyrate or acetoacetate). Ketone bodies are natural products produced by the breakdown of fatty acids and are used by tissues as an energy source. Acetoacetate is formed from acetyl CoA, and beta-hydroxybutyrate is formed by the reversible reduction of acetoacetate. Physiologically, the ratio of hydroxybutyrate to acetoacetate depends upon the NADH/NAD+ ratio inside the cell. As used herein with respect to ischemia/reperfusion protection, "ketone bodies" refers to beta-hydroxybutyric acid or a pharmaceutically acceptable salt thereof or acetoacetic acid or a pharmaceutically acceptable salt thereof, or any combination thereof. The term "pharmaceutically acceptable salt" refers to salts which possess toxicity profiles within a range that affords utility in pharmaceutical applications. Unless clearly indicated otherwise, reference in the specification to beta-hydroxybutyrate or acetoacetate should be understood as encompassing salt forms of the compound, whether or not this is explicitly stated.

Suitable pharmaceutically acceptable acid-addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4 hydroxybenzoic, phenylacetic, mandelic, embonic (pamoic), methanesulfonic, ethanesulfonic, benzenesulfonic, pantothenic, trifluoromethanesulfonic, 2 hydroxyethanesulfonic, p toluenesulfonic, sulfanilic, cyclohexylaminosulfonic, stearic, alginic, β hydroxybutyric, salicylic, galactaric and galacturonic acid.

Suitable pharmaceutically acceptable base-addition salts include, for example, metallic salts including alkali metal, alkaline earth metal and transition metal salts such as, for example, calcium, magnesium, potassium, sodium and zinc salts. Pharmaceutically acceptable base-addition salts also include organic salts made from basic amines such as, for example, N,N' dibenzylethylenediamine, chloroprocaine, choline, diethanolamine, ethylenediamine, meglumine (N methylglucamine) and procaine.

All of these salts may be prepared by conventional means from beta-hydroxybutyrate or acetoacetate by reacting, for example, the appropriate acid or base with beta-hydroxybutyrate or acetoacetate. Preferably, the salts are in crystalline form, and preferably prepared by crystallization of the salt from a suitable solvent. The person skilled in the art will know how to prepare and select suitable salt forms for example, as described in *Handbook of Pharmaceutical Salts: Properties, Selection, and Use* By P. H. Stahl and C. G. Wermuth (Wiley-VCH 2002).

The salt of beta-hydroxybutyric acid and/or acetoacetic acid is generally preferred in an ischemia/reperfusion protection composition, as the composition will be closer to a physiologically acceptable pH than when the acid is used. A suitable salt of beta-hydroxybutyric acid for use in an ischemia/reperfusion protection composition is the sodium salt of D-beta-hydroxybutyrate (i.e., Na-D-beta hydroxybutyrate). D-beta-hydroxybutyric acid and acetoacetic acid (or pharmaceutically acceptable salts thereof) can be obtained commercially from a number of companies such as, for example, Sigma Chemical Co. (St. Louis, Mo.). It is noted that the 'D' stereoisomer of beta-hydroxybutyrate, sometimes referred to as the 'R' stereoisomer, is preferred in an ischemia/reperfusion protection composition described herein as opposed to the 'L' stereoisomer.

Melatonin (5-methoxy-N-acetyltryptamine) is a hormone that is naturally synthesized from the amino acid tryptophan via synthesis from serotonin, and is well known for its involvement in the circadian rhythm (sleep-wake patterns). Melatonin acts as a broad-spectrum antioxidant and exhibits receptor-independent free radical scavenging activity. The free radical scavenging capacity of melatonin extends to its secondary, tertiary and quaternary metabolites, such that the interaction of melatonin with reactive oxygen and nitrogen species is a prolonged and cascade-type process that involves many of its metabolites. Therefore, metabolites, immediate precursors, or analogs of melatonin (or combinations thereof) can be used in an ischemia/reperfusion protection composition as described herein. Representative metabolites of melatonin include, for example, 6-hydroxy-melatonin (6-HMEL), 6-sulphatoxy-melatonin (aMT6s), $N^1$-acetyl-$N^2$-formyl-5-methoxy kynuramine (AFMK), $N^1$-acetyl-5-methoxy kynuramine (AMK), and 3-hydroxymelatonin (3-HMEL); representative immediate precursors of melatonin include, for example, e.g., N-acetylserotonin, 5-hydroxytryptamine, 5-hydroxytryptophan, or L-tryptophan; and representative analogs of melatonin include, for example, 2-chloromelatonin, 6-fluoromelatonin, 6-chloromelatonin, 6-hydroxymelatonin, N-isobutanoyl 5-methoxytryptamine, N-valeroyl 5-methoxytryptamine, 6-methoxymelatonin, 5-methyl N-acetyltryptamine, 5-benzoyl N-acetyltryptamine, O-acetyl 5-methoxytryptamine, N-acetyltryptamine, N-acetyl 5-hydroxytryptamine, and 5-methoxytryptamine. Although not bound by any particular mechanism, melatonin, melatonin metabolites, precursors or analogs, or a functionally-similar small molecule may exert their effects via a receptor-mediated route (e.g., via melatonin receptor 1A (MTNR1A) or melatonin receptor 1B (MTNR1B)), thereby contributing to the ischemia/reperfusion protection reported herein. As indicated herein, reference in the specification to melatonin or melatonin metabolites, precursors or analogs should be understood to encompass salt forms, unless stated otherwise.

In addition to or instead of melatonin or melatonin metabolites, precursors or analogs, an ischemia/reperfusion protection composition can include one or more other antioxidants. Representative antioxidants include, without limitation, resveratrol, vitamin A, ascorbic acid (vitamin C), alpha-tocopherol (vitamin E), glutathione, beta-carotene, lycopene and/or 4-hydroxy-2,2,6,6-tetramethylpiperidine-N-oxyl (TEMPOL™). Further, since melatonin is a tryptophan-derived antioxidant, derivatives of other amino acids that have antioxidant activity (e.g., cysteine, e.g., (R)-2-acetamido-3-mercaptopropanoic acid (N-acetyl-cysteine) or a synthetic cysteine derivative, 2-[(2-methyl-2-sulfanylpropanoyl)amino]-3-sulfanylpropanoic acid (Bucillamine)) also can be suitable for use in an ischemia/reperfusion protection composition.

An ischemia/reperfusion protection composition described herein can be formulated, for example, as a liquid that is ready for use or as a dry powder that requires dissolution or re-suspension prior to use. When formulated as a dry powder, an ischemia/reperfusion protection composition can have anywhere from less than one mole up to $1 \times 10^7$ moles or more of ketone bodies for every mole of melatonin or a melatonin metabolite, precursor or analog (e.g., (0.67-10,000,000):1). A ratio of ketone bodies to melatonin of about 100 to about 1 was exemplified herein, but an ischemia/reperfusion protection composition can contain more or less ketone bodies or more or less melatonin (or metabolite, precursor or analog). Representative mole to mole ratios of ketone bodies to melatonin or melatonin metabolite, precursor or analog in an ischemia/reperfusion protection composition can include, for example, a ratio of about 1:1, 5:1, 10:1, 25:1, 50:1, 100:1, 200:1, 500:1, 800:1, 1000:1, 2000:1, 4000:1, 6000:1, 8000:1, 10,000:1, 50,000:1, 75,000:1, 100,000:1, 250,000:1, 500,000:1, 750,000:1, $1 \times 10^6$:1, $1.13 \times 10^6$:1, $1.27 \times 10^6$:1, $1.35 \times 10^6$:1, $1.44 \times 10^6$:1, $1.5 \times 10^6$:1, $1.62 \times 10^6$:1, $1.76 \times 10^6$:1 $1.89 \times 10^6$:1 $1.97 \times 10^6$:1, $2.11 \times 10^6$:1, $2.33 \times 10^6$:1, $2.5 \times 10^6$:1, $3.5 \times 10^6$:1, $4.2 \times 10^6$:1, $5.4 \times 10^6$:1, $6.7 \times 10^6$:1, $7.3 \times 10^6$:1, $8.8 \times 10^6$:1, $9.1 \times 10^6$:1, or $1 \times 10^7$:1). Those of skill would understand that these ratios are simply meant to be exemplary.

When formulated as a liquid, the composition can be from about 0.1 M to about 8 M ketone bodies (e.g., about 0.4 M to 0.5 M, 0.4 M to 0.6 M, 0.4 M to 0.8 M, 0.6 M to 0.8 M, 0.5 M to 0.9 M, 0.5 M to 1 M, 0.8 M to 1.3 M, 1 M to 2 M, 0.5 M to 8 M, 1 M to 8 M, 2 M to 8 M, 3 M to 8 M, 0.1 M to 7.5 M, 0.1 M to 7 M, 0.1 M to 6 M, 0.1 M to 5 M, 0.5 M to 7.5 M, 1 M to 7 M, 2 M to 6 M, 3 M to 5 M, 3.5 M to 4.5 M, or about 3 M, 4 M, or 5 M ketone bodies) and from about 4 nM to about 150 mM melatonin or melatonin metabolite, precursor or analog (e.g., about 4 nM to 50 nM, 4 nM to 100 nM, 4 nM to 200 nM, 4 nM to 0.4 µM, 50 nM to 100 nM, 100 nM to 0.4 µM, 0.4 µM to 8 µM, 0.4 µM to 40 µM, 0.4 µM to 100 µM, 0.4 µM to 500 µM, 0.4 µM to 1 mM, 0.4 µM to 50 mM, 4 µM to 50 µM, 4 µM to 200 µM, 4 µM to 500 µM, 4 µM to 1 mM, 4 µM to 50 mM, 4 µM to 100 mM, 8 µM to 50 µM, 8 µM to 250 µM, 20 µM to 2 mM, 200 µM to 500 µM, 500 µM to 2 mM, 2 mM to 4 mM, 2 mM to 50 mM, 4 mM to 6 mM, 4 mM to 7 mM, 4 mM to 9 mM, 4 mM to 125 mM, 4 mM to 100 mM, 4 mM to 75 mM, 4 mM to 50 mM, 5 mM to 10 mM, 5 mM to 11 mM, 6 mM to 9 mM, 8 mM to 15 mM, 10 mM to 25 mM, 10 mM to 150 mM, 20 mM to 150 mM, 25 mM to 150 mM, 30 mM to 150 mM, 35 mM to 150 mM, 40 mM to 150 mM, 10 mM to 130 mM, 12.5 mM to 120 mM, 15 mM to 110 mM, 20 mM to 100 mM, 25 mM to 80 mM, 30 mM to 50 mM, 40 mM to 45 mM, 0.5 µM to 125 mM, 1 µM to 100 mM, 150 µM to 150 mM, 200 µM to 2 mM, 500 µM to 100 mM, 800 µM to 150 mM, or 750 µM to 125 mM melatonin or melatonin metabolite, precursor or analog). The concentration of each component must be below the saturation point of the solvent such that precipitation does not occur, although the concentration of each component can be relatively high as the toxicity of ketone bodies and melatonin is low. The final concentration of each component in an ischemia/reperfusion protection composition will depend upon several factors including the desired concentration of each component in the blood and the volume to be administered.

Any number of solvents can be used in a liquid ischemia/reperfusion protection composition or to dissolve or re-suspend a dry powder formulation of an ischemia/reperfusion protection composition. Since ketone bodies are readily water soluble, sterile distilled water can be used as the primary solvent. Since melatonin is more hydrophobic, a solubilizer (e.g., less than 50%, less than 40%, less than 30%, less than 25%, less than 24%, less than 23%, less than 22%, less than 21%, less than 15%, less than 10%, less than 8%, less than 6%, less than 5%, less than 4%, less than 3%, less than 2%, or less than 1% of the final volume) such as dimethyl sulfoxide (DMSO) or another non-polar solvent can be used to dissolve the melatonin. In addition to serving as a solubilizer, DMSO also can act as a hydroxyl radical scavenger (Paller et al., 1985, *J. Lab. Clin. Med.*, 105(4):459-63). Ethanol (EtOH) also can be used as a solubilizer for the melatonin, but requires higher concentrations and, therefore, may be less desirable although, under certain circumstances, may still be useful. Additional solvents that can be used include, for example, methylsulfonylmethane (MSM or dimethylsulfone) and dimethylformamide (DMF).

An ischemia/reperfusion protection composition that is stored for any amount of time as a liquid also may include one or more stabilizers such as organic sugars, sugar alcohols or saccharides, amino acids, and low molecular weight polypeptides or proteins (e.g., serum albumin or immunoglobulins) to prevent degradation of the active components and to prolong the shelf-life of a liquid composition. For example, CAPTISOL® (Cyclex, Inc., Lenexa, Kans.) is a representative compound (i.e., a modified cyclodextrin) that can be used to improve the solubility, stability and bioavailability of pharmaceutical compositions. In addition, either or both the ketone bodies or the melatonin (or melatonin metabolites, precursors or analogs) can be covalently attached to oligomers such as short, amphiphilic oligomers that enable oral administration or improve the pharmacokinetic or pharmacodynamic profile of the ketone bodies and/or the melatonin (or melatonin metabolites, precursors or analogs). The oligomers can include water-soluble polyethylene glycol (PEG) and/or lipid-soluble alkyls (short chain fatty acid polymers). See, for example, WO 2004/047871.

Generally, the ischemia/reperfusion protection compositions described herein are substantially free of inorganic anions. Inorganic anions include, for example, fluoride, chloride, bromide, nitrite, nitrate, ortho-phosphate, and sulfate. Typically, "substantially free" refers to an amount of inorganic anions that is less than about 10 mM (e.g., less than about 5 mM, 1 mM, 0.5 mM, 0.1 mM, 0.05 mM, 0.01 mM or 0.001 mM).

If necessary, depending upon whether an acid or salt is used, the pH of the liquid composition may require adjustment prior to use. If so, an appropriate acid (e.g., HCl) or salt (e.g., NaOH) can be used to adjust the pH to a physiologically acceptable range (e.g., a pH of from about 7.2 to about 7.6; e.g., a pH of about 7.4). In these instances, the amount of acid or salt added to reach an acceptable pH is considered to be sufficiently small that the composition is still considered to be substantially free of inorganic anions. In addition to or alternatively to adjusting the pH of a composition, a liquid ischemia/reperfusion protection composition may be filtered, for example, to sterilize the composition and/or to remove any non-solubilized crystals in the composition prior to use.

Although an ischemia/reperfusion protection composition simply containing one or more ketone bodies and melatonin or melatonin metabolites, precursors or analogs functions well, an ischemia/reperfusion protection composition also can contain one or more therapeutic compounds. Therapeutic compounds include, but are not limited to antibiotics or antibacterials (e.g., cephalosporins (e.g., Ceftriaxone), tetracyclines (e.g., minocycline) or other beta-lactams, particularly those that exhibit neuroprotective effects, as well as diaminodiphenyl sulfone (Dapsone) or D-Penicillamine), analgesics, free fatty acids, hormones, metabolites, and metabolic pathway molecules. In addition, therapeutic compounds include compounds that alter cellular metabolism such as, without limitation, polypeptides, antisense or siRNA molecules, drugs, and small molecules directed toward one or more appropriate targets. An ischemia/reperfusion protection composition also can include one or more components that can act as metabolic substrates such as, without limitation, glucose, acetate or pyruvate.

Methods of Using Ischemia/Reperfusion Protection Compositions

Ketone bodies and melatonin or melatonin metabolites, precursors or analogs can be used to treat tissues, organs, or an individual that is experiencing, is at risk of experiencing or has experienced ischemic damage/reperfusion injury. Ischemic damage/reperfusion injury can result from a number of different traumas. For example, ischemic damage/reperfusion injury can occur in an individual who is experiencing or has experienced blood loss, an individual who has had or is at risk of having a stroke, or an individual who is going to undergo or is undergoing surgery.

Ischemic injury can occur in tissues and organs when an individual loses blood and the tissues and organs are not sufficiently oxygenated, and reperfusion injury can occur when blood flow resumes or the individual is subsequently transfused with blood and the tissues and organs are reoxygenated. Blood loss as referred to herein can be caused by, for example, a major hemorrhagic event (e.g., a sudden or rapid loss of a significant amount of blood). Major hemorrhagic events include, without limitation, loss of a limb, long bone fractures, laceration of an artery, or a gunshot or artillery wound. Major hemorrhagic events also include blunt trauma events that may, for example, result in internal bleeding. Motor vehicle accidents are leading causes of major hemorrhagic events. Additional causes of major hemorrhagic events include, without limitation, gastrointestinal, obstetric and gynecological bleeding.

Major hemorrhagic events also include hemorrhagic shock. Principle contributors to shock in acute trauma patients include, without limitation, impaired oxygen uptake such as loss of airway patentcy, diminished respiration, aspiration, and pulmonary injury; decreased cardiac output such as hemothorax or pneumothorax, cardiac tamponade, hypovolemia, preexisting cardiac ischemia, or cardiac injury; loss of vasomotor tone such as exogenous vasodilators (e.g., drugs and alcohol), iatrogenic vasodilators (e.g., anesthetic and sedative agents, closed head injury, spinal cord injury, anaphylaxis); decreased oxygen carrying capacity such as anemia or cyanide poisoning; microvascular failure such as reperfusion injury, "no reflo" phenomenon, or failure of cellular metabolism (e.g., sepsis).

An ischemia/reperfusion protection composition as described herein can be administered in instances in which an individual has lost a blood volume of at least about 10% (e.g., at least about 20%, at least about 30%, at least about 40%, at least about 50%, at least about 60% or more). It is noted that the volume of blood in an adult is considered to be approximately 7%-9% of their total body weight. A systolic blood pressure of about 90 mm Hg or less (e.g., about 85 mm Hg or less, about 80 mm Hg or less, about 75 mm Hg or less, about 70 mm Hg or less, 65 mm Hg or less, about 60 mm Hg or less, about 55 mm Hg or less, or about 50 mm Hg or less), StO2 levels below 75% (e.g., below 70%, below 65%, below 60%, below 55%, or below 50%), and base deficit levels of greater than 6 mEq/L (e.g., greater than 6.5 mEq/L or greater than 7 mEq/L) are indicative of significant blood loss.

During blood loss, an individual's heart rate can increase, blood pressure can decrease, urine output can decrease, lactate levels can increase, tissue hemoglobin oxygen saturation ($StO_2$) levels can decrease, cardiac output can decrease, tissue pH can decrease, and mitochondrial function can decrease (e.g., as measured by NADH levels). Individual's recovering from such blood loss generally will exhibit a reversal of such symptoms; the heart rate can decrease, blood pressure can increase, urine output can increase, lactate levels can decrease, StO2 levels can increase, cardiac output can increase, tissue pH can increase, and mitochondrial function can increase. Generally, by way of example, a generally healthy individual (e.g., one who is not suffering from hemorrhagic shock) typically will have a heart rate of less than 100 beats/minute, blood pressure of greater than 100 mm Hg systolic, urine output of greater than 30 cc/hour (or 1 cc/kg/ hour for children), lactate levels of less than 2.1 mg/deciliter (dl), StO2 levels of greater than 75%, and cardiac index of 2.5-4.5 liters/min/m$^2$ (body surface area), blood pH of 7.35- 7.45, while an individual suffering from hemorrhagic shock (e.g., 10% blood loss or more) may have a heart rate of greater than 100 beats/minute, blood pressure of less than 100 mm Hg systolic, urine output of less than 300 cc/hour, lactate levels of greater than 2.1 mg/dl, StO2 levels of less than 75%, cardiac index of less than 2.5 liters/min/m$^2$, and blood pH of less than 7.35. Often, the severity of the change in the biophysical parameter is directly related to the amount of blood lost and, therefore, such biophysical parameters can be monitored in individuals who are experiencing blood loss or are recovering from such blood loss. Administering the ischemia/ reperfusion protection composition described herein can significantly temper the individuals' response to the blood loss (as gauged by one or more of the biophysical parameters described herein compared to an individual who undergoes a similar amount of blood loss but is not administered the composition) and/or increase the rate at which the biophysical parameter returns to "normal" (i.e., levels observed in generally healthy individuals).

Ischemic damage/reperfusion injury can result from, without limitation, stroke (e.g., occlusion stroke), cardiac arrest, myocardial infarction, heart attack, decreased arterial blood flow, or renal failure. Ischemic damage/reperfusion injury also can result from surgery in which the bloodflow and/or oxygen flow is or may be disrupted. Certain surgical procedures such as neurosurgery or cardiac surgery have a higher risk for ischemic damage/reperfusion injury, and even using mechanical means (e.g., a heart-lung machine) during surgery may not entirely prevent ischemic damage/reperfusion injury. The ischemia/reperfusion protection compositions described herein can be administered to individuals to significantly reduce or prevent ischemic damage/reperfusion injury that tissues and organs might experience during or following such medical emergencies (e.g., severe hypothermia or hypoxia) or procedures (e.g., surgeries).

As discussed herein, one or more ketone bodies and melatonin or melatonin metabolites, precursors or analogs can be solubilized and administered intravenously to introduce the components directly into the bloodstream. Other routes of administration, however, also are suitable and include, for example, intraosseous, intraperitoneal, oral, buccal, inhalation, or rectal administration (via, for example, a suppository). The particular formulation of an ischemia/reperfusion protection composition will be appropriate for the intended route of administration, and formulations for administration are well known in the art. See, for example, *Remington: The Science and Practice of Pharmacy*, 2005, 21$^{st}$ Ed., Lippincott Williams & Wilkins. Depending upon the particular formulation, an ischemia/reperfusion protection composition can include one or more of the following components: a sterile diluent such as water, saline solution (e.g., phosphate buffered saline (PBS)), fixed oils, a polyol (for example, glycerol, propylene glycol, and liquid polyetheylene glycol, and the like), glycerine, or other synthetic solvents; antibacterial and antifungal agents such as parabens, chlorobutanol, phenol, ascorbic acid, thimerosal, and the like; chelating agents such as ethylenediaminetetraacetic acid; buffers such as acetates, citrates or phosphates and agents for the adjustment of tonicity such as sodium chloride or dextrose.

Oral compositions generally include an inert diluent or an edible carrier, and can be liquid, or can be enclosed in gelatin capsules or compressed into tablets. Tablets, pills, capsules and the like can contain any of the following ingredients: a binder such as microcrystalline cellulose, gum tragacanth or gelatin; an excipient such as starch or lactose; a disintegrating agent such as alginic acid, Primogel, or corn starch; a lubricant such as magnesium stearate, sodium benzoate, sodium acetate, fumaric acid or Sterotes; a glidant such as colloidal silicon dioxide; a sweetening agent such as sucrose or saccharin; or a flavoring agent such as peppermint, methyl salicylate, or orange flavoring. An oral formulation of an ischemia/reperfusion protection composition can include an effervescent component, which can act as a penetration enhancer to increase absorption of one or more of the ingredients. An effervescent tablet, for example, when added to water, generates carbon dioxide gas due to a reaction between an acid and a base. The acid often is citric acid (hydrated or anhydrous), but also can be tartaric, fumaric, adipic, or malic acid. The base can be a water-soluble alkaline carbonate such as sodium bicarbonate, or an alkaline or alkaline earth metal carbonate such as potassium or calcium carbonate or bicarbonate, sodium carbonate, or sodium glycine carbonate.

In addition, an ischemia/reperfusion protection composition can be appropriately encapsulated (e.g., in a liposome) and delivered in an aerosolized or nebulized form. See, for example, U.S. Pat. Nos. 5,049,388, 5,141,674, 7,083,572 and 7,097,827. Nebulization shears the particles to sizes readily discharged from the nozzle of the nebulizer, which allows for inhalation of the sheared particles and subsequent release of the encapsulated material into the epithelium of the respiratory tract, the lungs and the blood stream. In certain instances, both the ketone bodies and the melatonin or melatonin metabilites, precursors or analogs can be encapsulated together; in other instances, the ketone bodies and the melatonin or melatonin metabilites, precursors or analogs can be encapsulated separately and mixed during aerosolization or nebulization. Liposomes up to several microns in diameter can be sheared to diameters of less than 500 nm, and may be considerably smaller depending upon the nebulizer and other factors.

An ischemia/reperfusion protection composition can be administered as a bolus, for example, by a first-responder (e.g., an armed services medic, an Emergency Medical Technician (EMT) or any other trained medical personnel) to an individual experiencing a major hemorrhagic event or a stroke or cardiopulmonary arrest. Alternately or in addition to a bolus administration, an ischemia/reperfusion protection composition can be administered as a slow-drip or infusion over a period of time. For example, a slow-drip or infusion can be administered at the scene of trauma, during transport to a medical facility, and/or once the individual reaches a medical facility. Physiologically, the period immediately after injury or trauma is critical and is sometimes referred to as the "golden hour," but administration of an ischemia/reperfusion protection composition to an individual can be continued for up to 72 hours or longer (e.g., up to 1 hour, 2 hours, 4 hours, 6 hours, 8 hours, 12 hours, 18 hours, 24 hours, 36 hours, 48 hours, 60 hours, 90 hours, or more). As an alternative to a slow-drip or infusion, a bolus of an ischemia/reperfusion protection composition can be administered multiple times over, for example, a 24, 48 or 72 hour period of time.

Generally, an individual who has experienced a major hemorrhagic event will receive a blood transfusion upon reaching a medical facility, which, depending upon the circumstances, may take only a few minutes following the injury or may take up to several hours or more. In some instances, an ischemia/reperfusion protection composition can be administered to an individual as soon as a potential ischemia or reperfusion injury is recognized, which may be after a blood transfusion has already begun. Those of skill would realize that an ischemia/reperfusion protection composition could be administered coincidentally with a blood transfusion or plasma replacement and, in some instances, an ischemia/reperfusion protection composition can be combined directly with the blood or plasma and administered to an individual.

Using, for example, a concentration of about 4 M ketone bodies and about 43 mM melatonin, a volume of about 0.3 to about 2 milliliters (mls; e.g., about 0.3 to 0.4 mls, 0.3 to 0.7 mls, 0.5 to 1.5 mls, 0.5 to 1.0 mls, 0.6 to 0.7 mls, 0.75 to 2 mls, 1.0 to 2.0 mls, 1.5 to 2.0 mls, or about 0.5, 0.1 or 1.5 mls) per kilogram (kg) of weight of an individual is effective in protecting individuals from ischemic damage/reperfusion injury due to severe blood loss. This small volume is significantly beneficial for emergency medical care in the field or under other circumstances in which supplies or space may be limited. Under other circumstances such as in a hospital or trauma center, however, a larger volume of an ischemia/reperfusion protection composition (e.g., 100 ml or more per kg) can be administered to an individual and the concentrations of each component adjusted appropriately.

It is generally desired, although not required, that the ketone bodies be administered to an individual in an amount sufficient to achieve a concentration in the blood at some point following administration of about 3 mM up to about 12 or 15 mM (e.g., about 3 mM to 10 mM, 3 mM to 7.5 mM, 3 mM to 5 mM, 3.5 mM to 10 mM, 4 mM to 10 mM, 6 mM to 10 mM, or about 4 mM, 5 mM, 6 mM, 7 mM, 8 mM, or 9 mM) and that the melatonin or melatonin metabolites, precursors or analogs be administered to an individual in an amount sufficient to achieve a concentration in the blood at some point following administration of about 30 µM to about 150 µM (e.g., about 30 µM to 125 µM, 30 µM to 100 µM, 30 µM to 80 µM, 30 µM to 60 µM, 30 µM to 50 µM, 30 µM to 40 µM, 35 µM to 150 µM, 40 µM to 150 µM, 50 µM to 150 µM, 60 µM to 150 µM, 70 µM to 150 µM, 80 µM to 150 µM, 100 µM to 150 µM, 35 µM to 125 µM, 40 µM to 100 µM, 50 µM to 75 µM, or 45 µM to 65 µM). In some instances, it is desirable to administer a much smaller amount of melatonin or melatonin metabolites, precursors or analogs (e.g., an amount sufficient to achieve a concentration in the blood of about $1 \times 10^{-10}$ mol/L, $2 \times 10^{-10}$ mol/L, $3 \times 10^{-10}$ mol/L, $4 \times 10^{-10}$ mol/L, $5 \times 10^{-10}$ mol/L, $6 \times 10^{-10}$ mol/L, or $7 \times 10^{-10}$ mol/L) to an individual. A medical practitioner can evaluate, on a case-by-case basis, whether and for how long to maintain the target concentrations, for example, by employing subsequent administrations or through the use of continuous infusion or other methods. The levels of ketone bodies and melatonin or melatonin metabolites, precursors or analogs in blood can be determined using methods routine in the art.

Ischemic damage/reperfusion injury also can occur in organs intended for transplant. One or more ketone bodies and melatonin or melatonin metabolites, precursors or analogs can be administered to an organ donor prior to organ harvest. The organ donor can be in a persistent vegetative state, or can be alive and healthy and a suitable match for the recipient. An organ donor can be intravenously administered the ketone bodies and melatonin or melatonin metabolites, precursors or analogs prior to the organ(s) being harvested so as to thoroughly perfuse the organ(s), thereby preventing or reducing ischemic damage of those tissues or organs during subsequent transport and transplant into a recipient. One or more ketone bodies and melatonin or melatonin metabolites, precursors or analogs can be administered to an organ donor to achieve a blood concentration as described above (e.g., 3-15 M ketone bodies and 30-150 µM melatonin) or can be administered to achieve an even higher concentration. In addition or alternatively to administering an ischemia/reperfusion protection composition to an individual, one or more harvested organs can be, for example, perfused with or soaked in (e.g., during transport) an ischemia/reperfusion protection composition.

A combination of one or more ketone bodies and melatonin or melatonin metabolites, precursors or analogs can be highly effective in protecting an individual from ischemic damage and/or reperfusion injury. For example, one or more ketone bodies and melatonin or melatonin metabolites, precursors or analogs can be administered to an individual who has experienced blood loss, has had a stroke or a cardiopulmonary arrest, is about to undergo or is undergoing a procedure such as surgery, or is an organ donor. A combination of one or more ketone bodies and melatonin or melatonin metabolites, precursors or analogs also can protect an individual who has lost one or more digits or an entire limb.

Articles of Manufacture

The ischemia/reperfusion protection compositions described herein or the components therein can be included in an article of manufacture. Articles of manufacture that include one or more ketone bodies and melatonin or melatonin metabolites, precursors or analogs can take any number of configurations, only a few of which are discussed herein. The following representative examples of articles of manufacture are not meant to be limiting.

In one embodiment of an article of manufacture, a liquid formulation of one or more ketone bodies and melatonin or melatonin metabolites, precursors or analogs are provided in an IV bag. See, for example, U.S. Pat. Nos. 5,098,409; 5,257,985; and 5,853,388. An ischemia/reperfusion protection composition provided in an IV bag can be provided sterile and ready for use, with an appropriate expiration date indicated on the bag. Alternatively, a dry powder composition of one or more ketone bodies and melatonin or melatonin metabolites, precursors or analogs can be provided in an IV bag ready for dissolution or re-suspension with an appropriate solvent.

In another embodiment, an article of manufacture can have at least a first and a second vessel, and sometimes a third and a fourth vessel. Depending upon the configuration, a first vessel can contain both the ketone bodies and the melatonin or melatonin metabolites, precursors or analogs, and a second vessel can contain a solvent. In an alternate configuration, the ketone bodies can be contained in a first vessel, melatonin or melatonin metabolites, precursors or analogs can be contained in a second vessel, while a third vessel can contain a solubilizer for the melatonin or melatonin metabolites, precursors or analogs and a fourth vessel can contain a solvent (e.g., an aqueous solvent) for dissolving or re-suspending the ketone bodies. In certain embodiments of an article of manufacture having more than one vessel, the liquid portions can be controllably placed into contact with the components or the composition portion. "Controllably placed into contact" refers to the ability of a user to actively determine when a liquid portion is combined with a dry powder portion, via structural features of the manufactured article that facilitate such controlled contacting. Such structural features could include, for example, breakable or puncturable seals or partitions.

In another embodiment, one or more ketone bodies and melatonin or melatonin metabolites, precursors or analogs can be provided within a syringe barrel. An ischemia/reperfusion protection composition in a syringe barrel can be provided already resuspended, provided in a dry powder form for resuspension prior to use, or provided in dry powder form with the syringe barrel also containing the solvent or solvents for resuspending the dry powder or its components. An article of manufacture for dispensing an ischemia/reperfusion protection composition can be an automated device that allows for administration of a desired dose (e.g., based on an individuals weight or approximate weight) of the protection composition.

In certain instances, a solution containing one or more ketone bodies and a solution containing melatonin or melatonin metabolites, precursors or analogs can be mixed prior to administration, such that an individual receives both components in a single composition. In other instances, one or more ketone bodies can be administered to an individual followed by or preceded by (separate) administration of melatonin or melatonin metabolites, precursors or analogs. Given that melatonin and ketone bodies may have different half-lives, in some embodiments, the two components may be initially administered together in a single composition followed by administration of one component (e.g., melatonin or melatonin metabolites, precursors or analogs) more frequently than administration of the other component (e.g., ketone bodies).

An article of manufacture generally includes packaging material in addition to ketone bodies and melatonin or melatonin metabolites, precursors or analogs. The packaging material can include a label or package insert that has instructions for treating an individual who is experiencing or has experienced blood loss, an individual who had a stroke or a cardiopulmonary arrest or is at risk of having a stroke or cardiopulmonary arrest, an individual who is about to undergo or is undergoing surgery, or an individual who is about to donate an organ or tissue.

It is advantageous to formulate ischemia/reperfusion protection compositions in dosage unit form for ease of administration and uniformity of dosage. Dosage unit form as used herein refers to physically discrete units suited as unitary dosages to be administered to an individual, with each unit containing a predetermined quantity of ischemia/reperfusion protection composition to produce the desired therapeutic effect. A dosage unit form of a composition of the invention generally is dependent, for example, upon the desired concentration of ketone bodies and melatonin or melatonin metabolites, precursors or analogs in the blood of an individual and the weight of an individual.

In accordance with the present invention, there may be employed conventional microbiology, biochemical, and biophysiological techniques within the skill of the art. Such techniques are explained fully in the literature. The invention will be further described in the following examples, which do not limit the scope of the invention described in the claims.

EXAMPLES

Example 1

Figure 2:
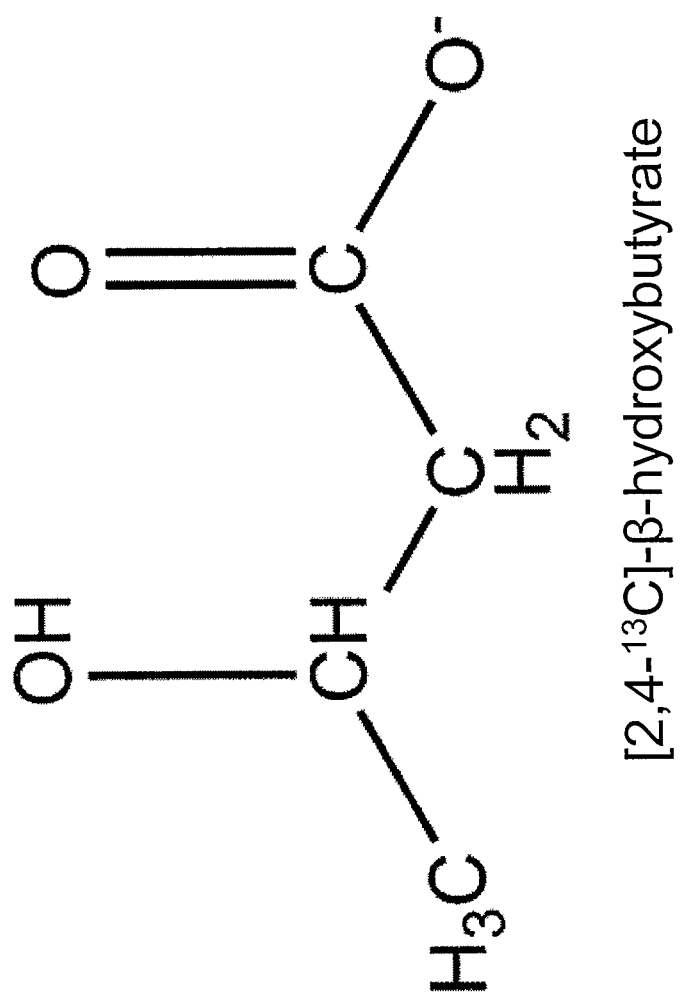
FIG. 2 shows the structure of [2,4-$^{13}$C] D-beta-hydroxybutyrate.

Metabolism of Glucose and D-Beta-Hydroxybutyrate in Brains and Hearts of Hibernating and Active Ground Squirrels Objective The transport and metabolism of D-β-hydroxybutyrate (BHB) in the brains of active and hibernating ground squirrels was measured by infusing [2,4-$^{13}C_2$]-BHB (FIG. 2) followed by detection of $^{13}$C-labeled BHB and metabolites in brain.

The overall strategy of these experiments was to measure incorporation of isotope from infused $^{13}$C-BHB into the brain pool of $^{13}$C-BHB and into the tricarboxylic acid (TCA) cycle-derived metabolites such as glutamate, glutamine and aspartate. The same experiments were performed in parallel using [1-$^{13}C_2$]-glucose (FIG. 1). A quantitative determination of BHB blood-brain transport and a rate of consumption (relative to glucose consumption) was determined in non-hibernating ground squirrels at euthermic temperatures and in hibernating ground squirrels at 4-6° C.

Animals

Ground squirrels were anesthetized (isoflurane) prior to placement in the magnet of the magnetic resonance (MR) instrument and were injected with $^{13}$C-BHB or [1-$^{13}C_2$]-glucose.

Analysis of Brain Metabolites in Tissue Extracts

At the completion of the $^{13}$C experiments, animals were sacrificed using funnel freezing of the brain with liquid nitrogen while still fully anesthetized. Frozen brains were chiseled out of the skull at −25° C. and pulverized under liquid nitrogen using a mortar. Perchloric acid brain extracts were analyzed using high-resolution NMR at 14 Tesla (600 MHz) at the University of Minnesota.

Results and Interpretation

It was noted that labeling rates in hibernating squirrels were very slow and required a minimum body temperature of approximately 12-16° C.

Figure 3:
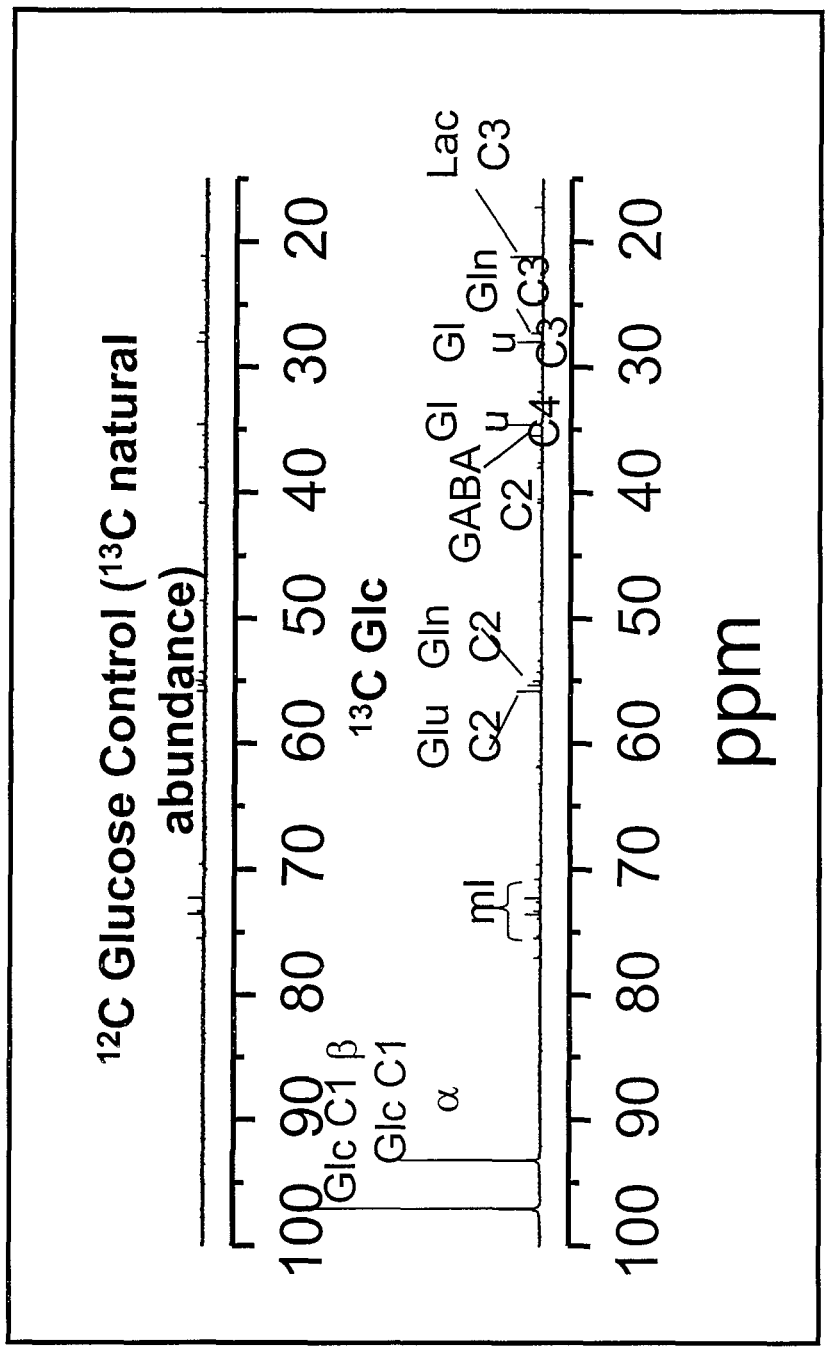
FIG. 3 is a graph showing the baseline levels of $^{13}$C-glucose in the brain.

To test the hypothesis that ketone bodies are preferentially utilized during hibernation, high-field NMR was performed on brain extracts from hibernating ground squirrels that had been injected with either 1 ml of 1 M $^{13}$C-labeled racemically pure D-beta-hydroxybutyrate ($^{13}$C-D-BHB) or 1 ml of 1 M $^{13}$C-glucose. FIG. 3 shows relative levels of glucose uptake into the brain. The results demonstrated that D-beta-hydroxybutyrate is a better substrate than glucose, and does not result in the generation of a significant amount of lactate.

Figure 4:
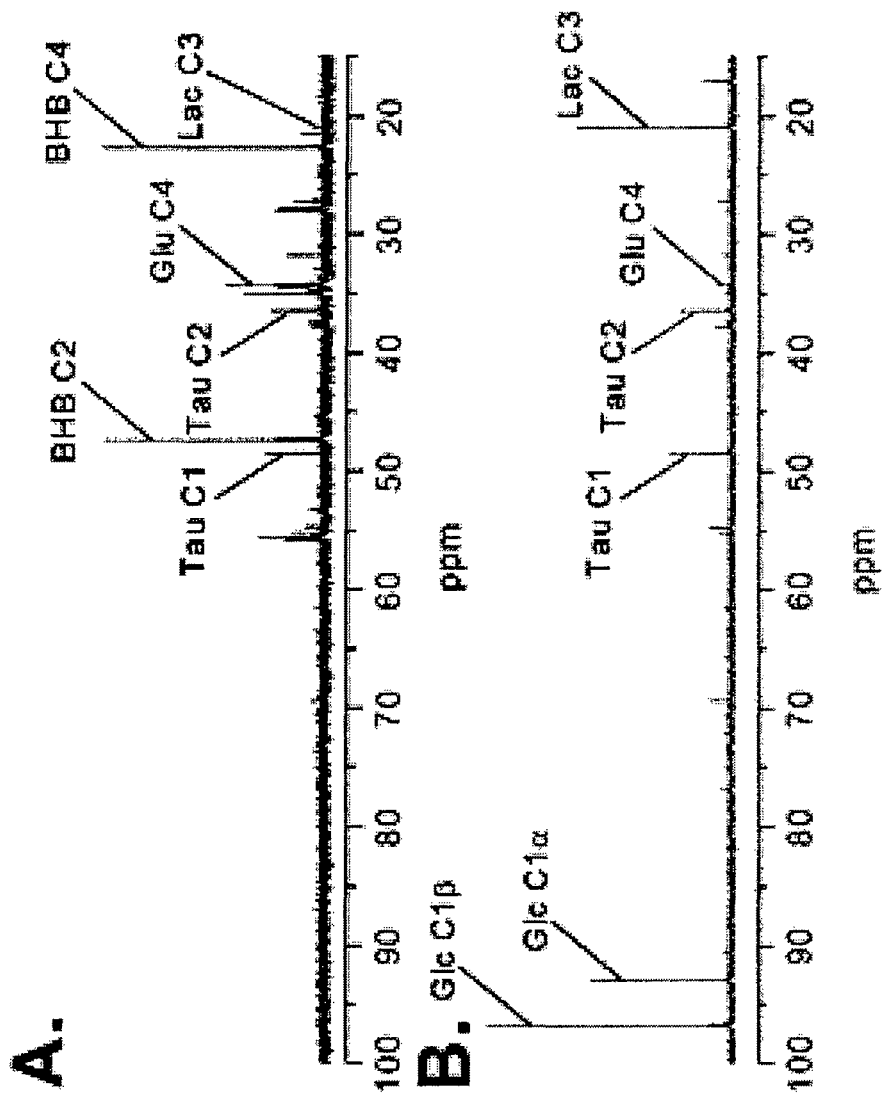
FIG. 4 is a labeled spectrum of selected metabolites from hibernating ground squirrels assayed on a 14.1 Tesla UNITY INOVA spectrophotometer (Varian; Palo Alto, Calif.). Panel A shows the results following IP injection of 1 ml of 1 M $^{13}$C BHB in a February hibernator (Tb=16.8° C. at time of sacrifice). Panel B shows the results following IP injection of 1 ml of 1 M $^{13}$C Glucose in a December hibernator (Tb=35.3° C. at time of sacrifice). Data in both panels were normalized to the two naturally labeled $^{13}$C-taurine peaks, which did not change with infusion of label and can be used to determine the concentration of the other respective metabolites. The abbreviations reflect the designated metabolites and the specific carbon labeled: Tau C1, taurine C1; BHB C2, beta hydroxybutyrate C2; Tau C2, taurine C2; Glu C4, glutamate C4; BHB C4, beta hyroxybutyrate C4; Lac C3, lactate C3; Glc C1-α, glucose C1 alpha; Glc C1β, glucose C1 beta.

FIG. 4 shows that $^{13}$C-D-BHB and $^{13}$C-glucose was efficiently transported into the heart during hibernation, but that there was a difference in how effectively each fuel source was utilized and incorporated into metabolites. In BHB-injected animals, metabolic intermediates derived from the TCA cycle were produced at low body temperature (Tb). FIG. 4A shows the levels of glutamate (labeled at carbon #4; Glutamate C4) in the heart were very high with many multiplets, indicating utilization of the glutamate substrate as well as production of glutamate and glutamine C3 and C2.

In animals that were administered glucose, the majority of $^{13}$C-glucose entered the heart but was not metabolized at the same high level as was D-BHB (FIG. 4B). Levels of TCA-cycle intermediates such as Glutamate C4 and others were not readily observed and the amounts that were formed were very small with no multiplets, even when the ground squirrel had a normothermic Tb of 35.3° C. at the time of sacrifice (FIG. 4B). The most dramatic result seen following an injection of labeled glucose was a very large spike in lactate. These results indicate that glucose was not utilized as efficiently as BHB, with the vast majority of metabolized glucose converted into lactate rather than advancing through the TCA cycle.

Example 2

Expression of Ketone Body Transporters and Ketolytic Enzymes in Brain and Heart

Objective

Brains from both active and hibernating ground squirrels and control and ketonemic rats were analyzed for monocarboxylic acid transporters MCT1 and MCT2 and for glucose transporter 1 (GLUT1) by immunocytochemistry and Western blots. These experiments examined whether changes in location and expression of these transporters correlate with differences in the metabolic state of animals (active vs. hibernating; control vs. ketonemic).

Measurements of Brain MCT1 and MCT2 by Western Blot

Protein from the brain of hibernating and non-hibernating animals were analyzed by Western blot analysis to quantify whether the various forms of MCT are differentially expressed based on the season and the animal's state of activity. Active (N=5) and hibernating (N=5) ground squirrels were euthanized and their brains promptly removed. The brains were sub-divided into cerebrum and brainstem and frozen immediately in liquid nitrogen. Brain membrane proteins were obtained by tissue homogenization followed by centrifugation to collect a membrane pellet.

MCT1 is known to be found in endothelial cell membranes and is more highly expressed in animals experiencing ketonemia from a high fat diet. MCT1 is also prominent in choroid plexus epithelium and in glial limiting membranes. MCT2 was first described as a membrane transporter abundant in astrocyte foot processes and other glial cells, and recent evidence suggests that MCT2 may also be significantly expressed in neurons.

Chicken polyclonal antiserum raised against the carboxyl terminus of rat MCT1, which has been shown to cross-react with a protein from ground squirrels of the same size as rat MCT1, was used to measure changes in the amount of MCT1 in ground squirrels. Similarly, rabbit polyclonal antiserum raised against the carboxyl terminus of rat MCT2, which has been shown to cross-react with a protein from ground squirrels of the same size as rat MCT2, was used to measure changes in the amount of MCT2 in ground squirrels.

Immunocytochemistry to Determine Cellular Location of MCT1, MCT2 and GLUT1

Rats and ground squirrels were anesthetized with 5% halothane prior to cardiac puncture perfusion with formal-acetic fixative (4% formaldehyde, 2% acetic acid). The perfusion time was 12 min and tissues were stored at 4° C. in fixative overnight before they were processed. Tissue sections were blocked with phosphate buffered saline (PBS) containing 0.1% bovine serum albumin (BSA) and 1.5% normal goat serum. The primary antibody was diluted 1:1200 in 0.1% BSA and applied to the sections for 1 h at room temperature. Sections were then incubated 30 min with biotinylated goat anti-mouse IgG (5 µg/ml in blocking solution) and 30 min with avidin-biotin-peroxidase complex (ABC) reagent (both reagents from Vector Laboratories, Burlingame, Calif.). Color development was from 1 to 6 min in 0.6 g/ml 3,3'-diaminobenzidine (Sigma).

The same antibody preparations (MCT1 and MCT2) used to probe Western blots described above were used to determine cellular location within the brain. Of particular interest was the relative amount and distribution in active versus hibernating ground squirrels. The location of MCT1, MCT2 and GLUT1 was examined in the cerebral cortex, hippocampus and cerebellum of the active and hibernating ground squirrel brain. These experiments focused on these brain regions to identify whether or not these MCT isoforms and GLUT1 are preferentially expressed in endothelial cells, astrocytes and/or neurons. It is known that the hippocampus is particularly sensitive to hypoxia. Light microscopy was performed according to Gerhart et al. (1997, *Am. J. Physiol.*, 273:E207-213).

Results and Interpretation

Figure 5:
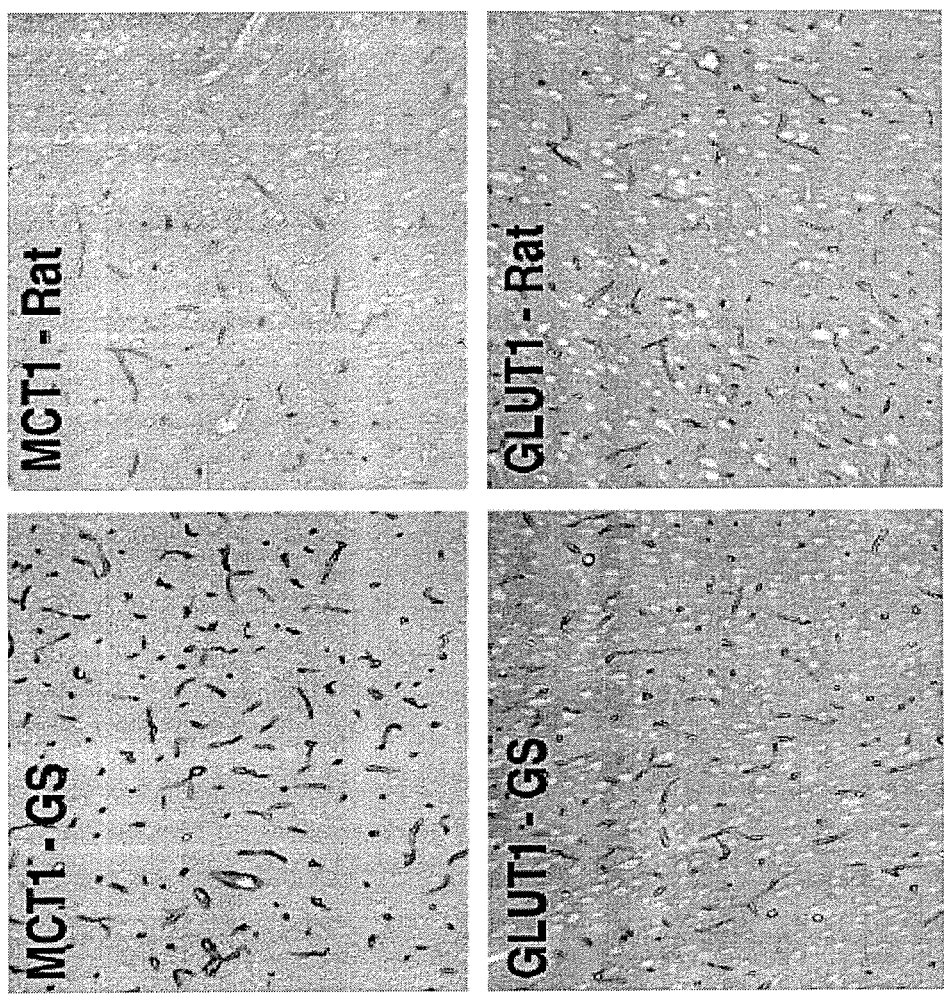
FIG. 5 shows the results of immunocytochemistry of monocarboxylate transporter 1 (MCT1) and glucose transporter (GLUT1) in rat and ground squirrel (GS) brains.
Figure 6:
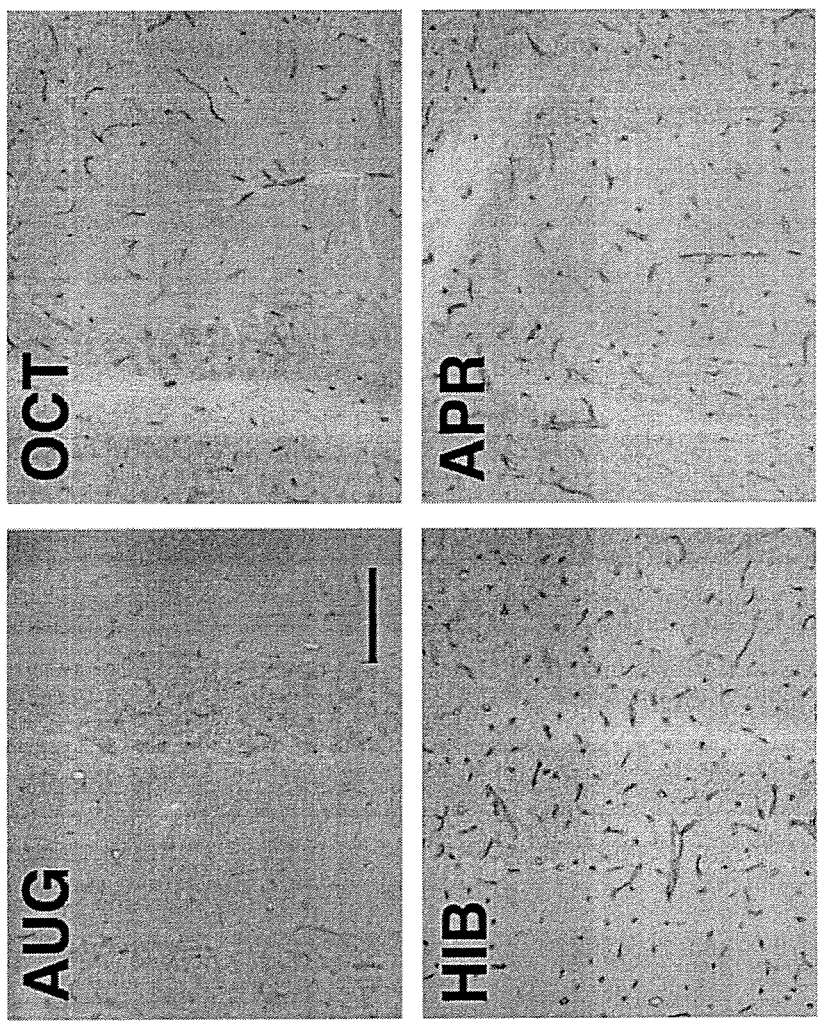
FIG. 6 shows the elevated levels of MCT1 at the blood brain barrier based on immunocytochemistry in hibernating ground squirrels.
Figure 7:
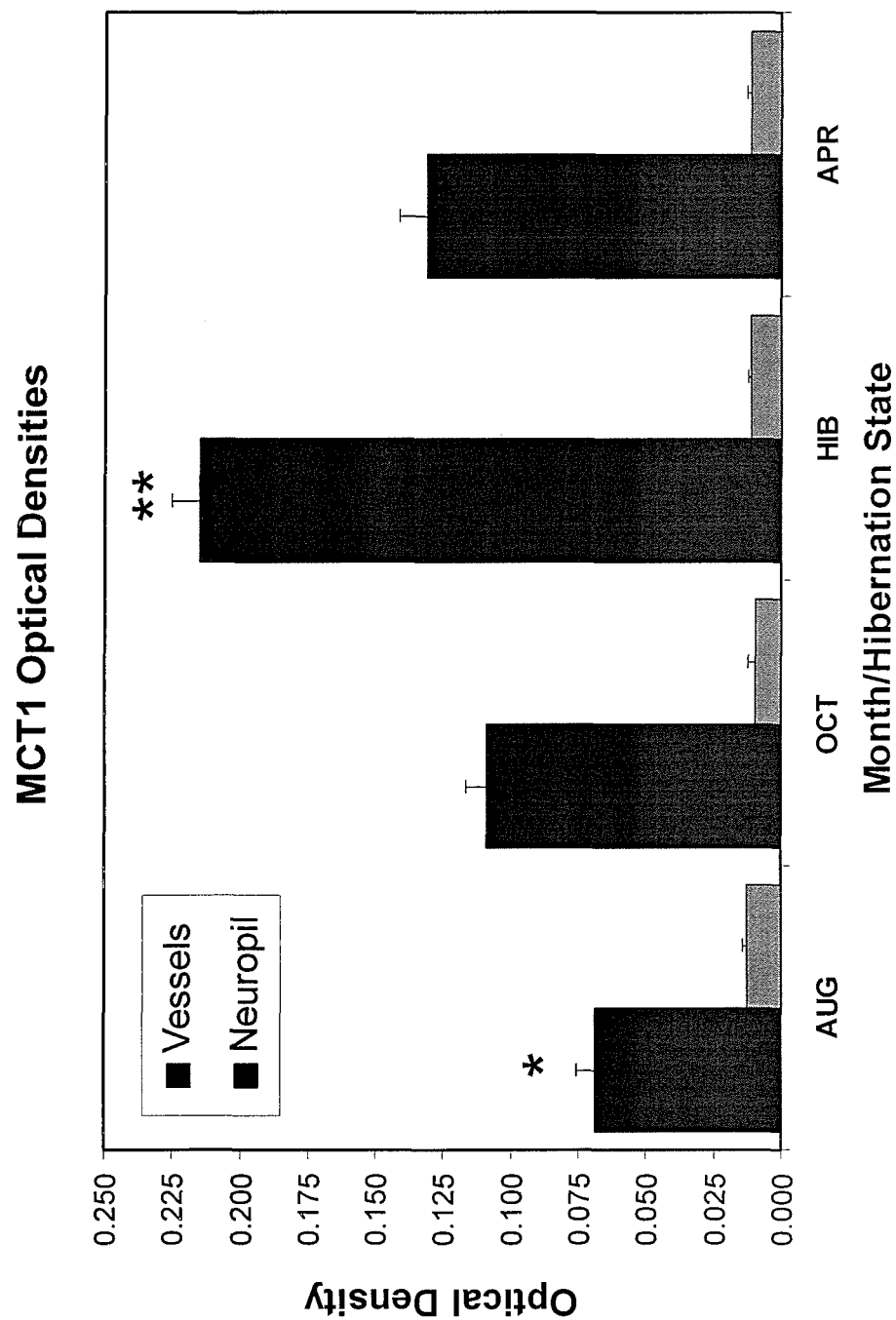
FIG. 7 shows elevated levels of MCT1 at the blood brain barrier based on optical density of MCT1 in blood vessels during hibernation (HIB) and in August (AUG), October (OCT), and April (APR).
Figure 8:
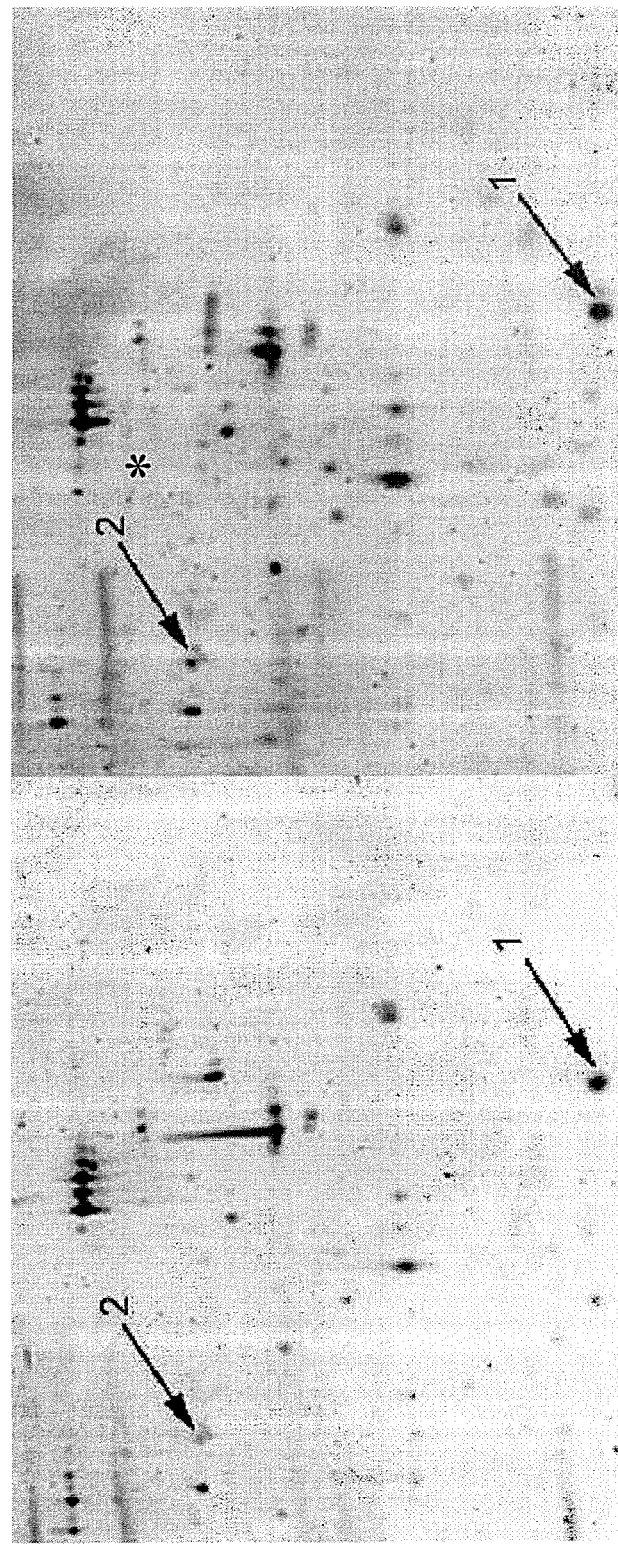
FIG. 8 shows 2-dimensional gels of polypeptides from active and hibernating ground squirrel hearts. 1, ventricular myosin light chain 1 (n.c., act, n=5; hib, n=4); 2, Succinyl CoA transferase (6-fold increase, *=p<0.005).

FIG. 5 shows the results of immunocytochemistry of MCT1 and glucose transporter (GLUT1) in rat and ground squirrel brains. FIG. 6 shows the seasonal variations of MCT1 expression in ground squirrel brains based on immunocytochemistry and indicates that elevated levels of MCT1 at the blood brain barrier during hibernation. FIG. 7 shows the elevated levels of MCT1 in vessels of hibernating animals based on the optical density of MCT1. FIG. 8 shows 2-dimensional gels from active and hibernating ground squirrel hearts. The 2-D protein gels show that succinyl CoA transferase (SCOT), the rate-limiting step in ketone body metabolism, is increased 6-fold in hibernating animals. Based on these results, levels of the ketone transporter, MCT1, increase in the brain during hibernation, and a similar increase is seen for SCOT in the heart of hibernating animals.

Example 3

Protection of Small Mammals from Significant Blood Loss

Objective

Rats infused with ketone bodies were subjected to 60% blood loss for at least 1 hour, followed by return of the shed blood. Endpoint measures of neuroprotection were quantitative analysis of neuronal survival and apoptosis in cortex, hippocampus and cerebellum as well as neurologic function exam scores. The objective was to determine the effectiveness of the D-form of beta-hydroxybutyrate (D-BHB) in conjunction with melatonin in protecting the brain from ischemia and providing protection from reperfusion injury after blood return.

The goal of the following experiments was to maintain 60% blood loss for at least three hours using a minimal amount of fluid in order to maintain viability. Sixty-percent blood loss was calculated by using the equation: Total blood volume=Animal body weight×0.06. A bolus volume of 1 ml ischemia/reperfusion protection composition per kilogram of animal body weight was given to animals after approximately 40% blood loss. Some animals only received a single 1 ml/kg bolus, while other animals received a slow infusion (100 µl/hr) to imitate an intravenous drip of solution after the bolus was given.

Animals

Male Sprague-Dawley rats (280-350 g) were obtained from Harland Teklad (Madison, Wis.) and allowed to acclimate for at least seven days before surgical preparation. All animals were fed a standard laboratory chow and provided water ad libitum until the day of experimentation. The care and handling of animals was approved by the Institutional Animal Care and Use Committee (IACUC) of the University of Minnesota.

Surgical Preparation

Animals were briefly anesthetized with isoflurane in breathing grade air followed by intramuscular injection of a ketamine/xylazine mixture (100/20 mg/kg) for anesthesia. The left femoral artery was aseptically isolated and cannulated with polyethylene (PE-50) tubing (0.023 ID, 0.038 OD) containing heparinized saline (10 Units/ml). The catheter was attached to a pressure transducer for continuous monitoring of mean arterial blood pressure (MABP) and heart rate (HR) (Powerlab, AD Intruments, Hastings, UK). The right femoral artery was similarly cannulated to facilitate blood withdrawal and sampling.

Once rats were fully anesthesized and stabilized for a 20 min period, blood loss was begun. At approximately 40% blood loss, 1 ml of 4M D-BHB or 4M NaCl/kg body weight was infused into the cannulated left femoral vein. After the bolus infusion, the 4M D-BHB or 4M NaCl was slowly infused into the animals at a rate of 100 µl/hr. Temperature was monitored with a rectal probe. Animals were maintained under anesthesia throughout the entire experiment using the ketamine/xylazine mixture. The experiment ensued after a 20 minute stabilization period while monitoring MABP, HR, and temperature. Animal death was recorded when blood pressure, respiration, and precordial movement ceased (see FIG. 9 for a timeline). Rats were sacrificed three days after the shed blood was returned.

Solutions

4M D-BHB: 0.5 g of D-beta-hydroxybuyrate was added up to 1 ml of distilled water. This solution was filter sterilized by passing it through a 0.2 micron filter (Acrodisc Syringe Filter, PALL).

4M NaCl: 0.233 g of sodium chloride was added up to 1 ml of distilled water. This solution was filter sterilized by passing through a 0.2 micron filter (Acrodisc Syringe Filter, PALL).

Melatonin/DMSO: 100 mg of melatonin was added to a 0.6 ml microcentrifuge tube. DMSO (>99% purity) was added up to 200 µl. The solution was vortexed and aliquoted into 6 µl amounts in 1.5 ml microcentrifuge tubes. Tubes were frozen (−20° C.) until use, and discarded after 1 week.

Infusion solution: One of the 6 µl melatonin/DMSO stock tubes was opened and 294 µl of 4M D-BHB or NaCl was added. Tubes were gently vortexed to ensure mixing. Infusion solution was prepared minutes before infusion into the animal. Remaining solution was discarded if not used.

Blood Serum Assays.

Blood samples taken via the right femoral artery during certain time points (see FIG. 9) were centrifuged at 3500 rpm for five mins. Serum collected at the time points was pipetted away from the tubes and aliquoted into twenty microliter volumes. These serum aliquots were frozen at −80° C. for permanent storage. Levels of β-hydroxybutyrate and glucose were obtained from serum samples by spectrophotometry (Multiskan) using Liquicolor test kits (Stanbio Laboratories). Samples were run in triplicate in order to reduce pipetting error.

Analysis of Ischemia-Induced Tissue Damage Resulting from Hemorrhagic Shock

Rat brains fixed by transcardial perfusion were embedded in paraffin, and coronal 10-μm-thick brain sections from the region of the anterior hippocampus were mounted on poly-L-lysine-coated glass slides. Three histological techniques were used to measure the areas of damaged tissue and to quantify, in selected microscope fields, the surviving and apoptotic neurons in specific brain regions.

Nissl (cresyl violet)—and hematoxylin and eosin (H&E)—stained sections were prepared in order to distinguish ischemia-damaged areas from undamaged areas of brain tissue sections. Neuronal injury in the CA1, CA2, CA3 hippocampal regions and in the dentate gyms was assessed quantitatively by cell counts. In addition, areas of general cytotoxic damage in cerebral cortex and thalamus relative to the total areas of these brain regions were measured in three sections taken from each brain (3.7, 4.0, and 4.3 mm from bregma). Photomicrographs of damaged areas were obtained using digital microscopy, and quantification was achieved using an image analysis software program (e.g., NIH Image) to identify damaged and normal brain areas. Student's t-test was used to evaluate the results statistically.

To quantify neuronal cell death, brain sections were processed for terminal deoxynucleotidyl transferase-mediated biotinylated UTP nick end labeling (TUNEL) staining with the in situ cell death detection kit (Boehringer Mannheim, Mannheim, Germany). TUNEL-positive neurons (i.e., cells undergoing apoptosis) were counted bilaterally in selected microscopic fields in the hippocampus, dentate gyms, cerebral cortex, and thalamus using NIH Image. Subsequently, the same sections were stained with 0.5% cresyl violet to evaluate surviving neurons.

Neurologic Defect Scoring System

The neurologic function of animals was evaluated at 1 and 3 days after blood return by the neurologic defect scoring system (Table 1).

TABLE 1

Neurologic defect scoring system for rats.

| Observed parameters | Characteristics | Scores for positive response |
|---|---|---|
| General | | |
| Consciousness | Responsive | 100 |
| Respiration | 60 < respiration < 120 | 100 |
| Cranial nerves | | |
| Olfactory | Orient to smell | 20 |
| Vision | Startle response to visual stimulus | 20 |
| Corneal reflex | Blink | 20 |
| Whisker movement | Spontaneous | 20 |
| Hearing | Startle response to loud noise | 20 |
| Motor | | |
| Four paws and tail | Spontaneous movement | 10 each, 50 total |
| Sensory | | |
| Four paws and tail | Reaction to pain | 10 each, 50 total |
| Coordination | | |
| Ledge traverse | | 25 |
| Righting reflex | | 25 |
| Placing test | | 25 |
| Stop at table edge | | 25 |
| Total | | 500 |

Statistical Analysis

Statistical analysis was performed using a two-tailed Student's t-test with $p<0.05$ considered statistically significant. For multi-group statistical analysis of parametric data, one-way ANOVA was conducted. Statistical values were represented as means±S.D.

Results and Interpretation

These experiments demonstrated that an ischemia/reperfusion protection composition that included BHB and melatonin maintained survival of animals experiencing 60% blood loss for approximately 3 hours, which was a significant improvement over the effects of NaCl. In addition, the ischemia/reperfusion protection composition of BHB and melatonin provided neural protection in rats, which resulted in improved outcomes after the shed blood was returned.

Figure 9:
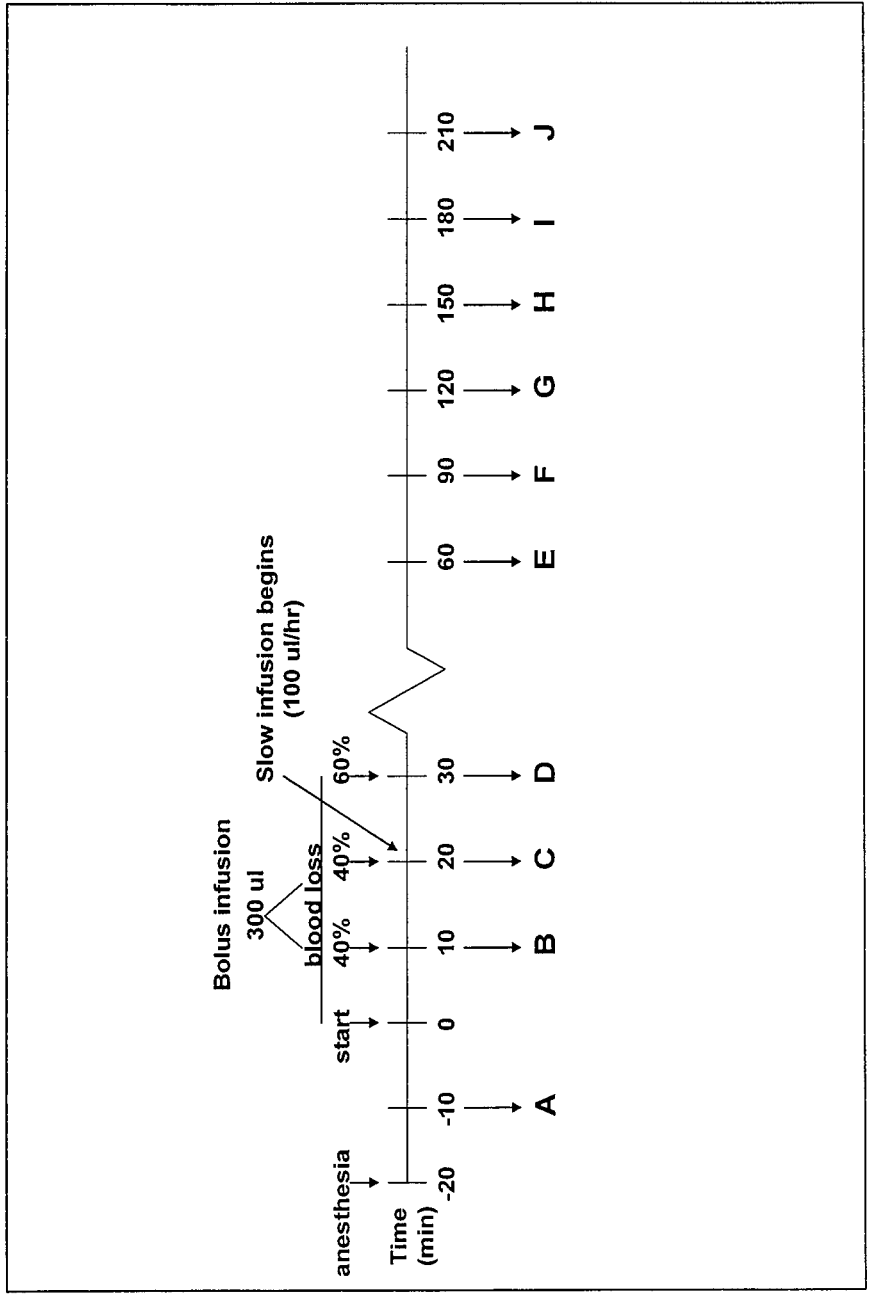
FIG. 9 shows a timeline of acute trauma experiments. Blood was taken at the lettered time points (A-J).

FIG. 9 shows the time-line for experiments to demonstrate that beta-hydroxybutyrate can be used to protect an individual from significant blood loss. Blood was taken before hypotension (A); ~40% blood loss (B); post solution infusion (C); 60% blood loss (D); 30 minutes post 60% blood loss (E); 60 minutes post 60% blood loss (F); 90 minutes post 60% blood loss (G); 120 minutes post 60% blood loss (H); 150 minutes post 60% blood loss (I); and 180 minutes post 60% blood loss (J).

Figure 10:
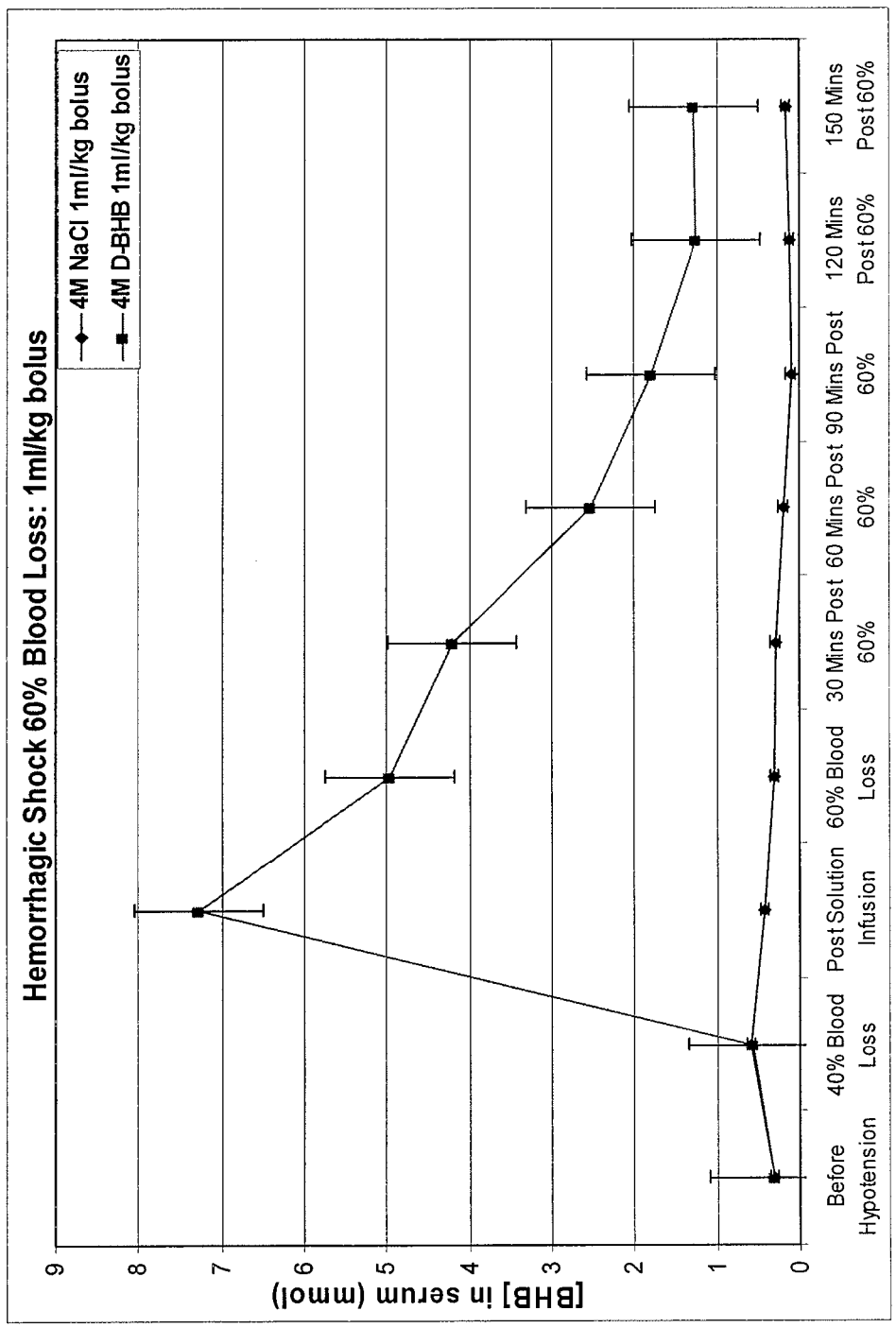
FIG. 10 shows a graph of serum levels of beta-hydroxybutyrate following administration of 1 ml of 4 M D-BHB or 4 M NaCl per kg rat. Samples were calculated in triplicate in order to minimize pipetting error and are given in mM concentrations. Error bars are standard errors of the mean.
Figure 11:
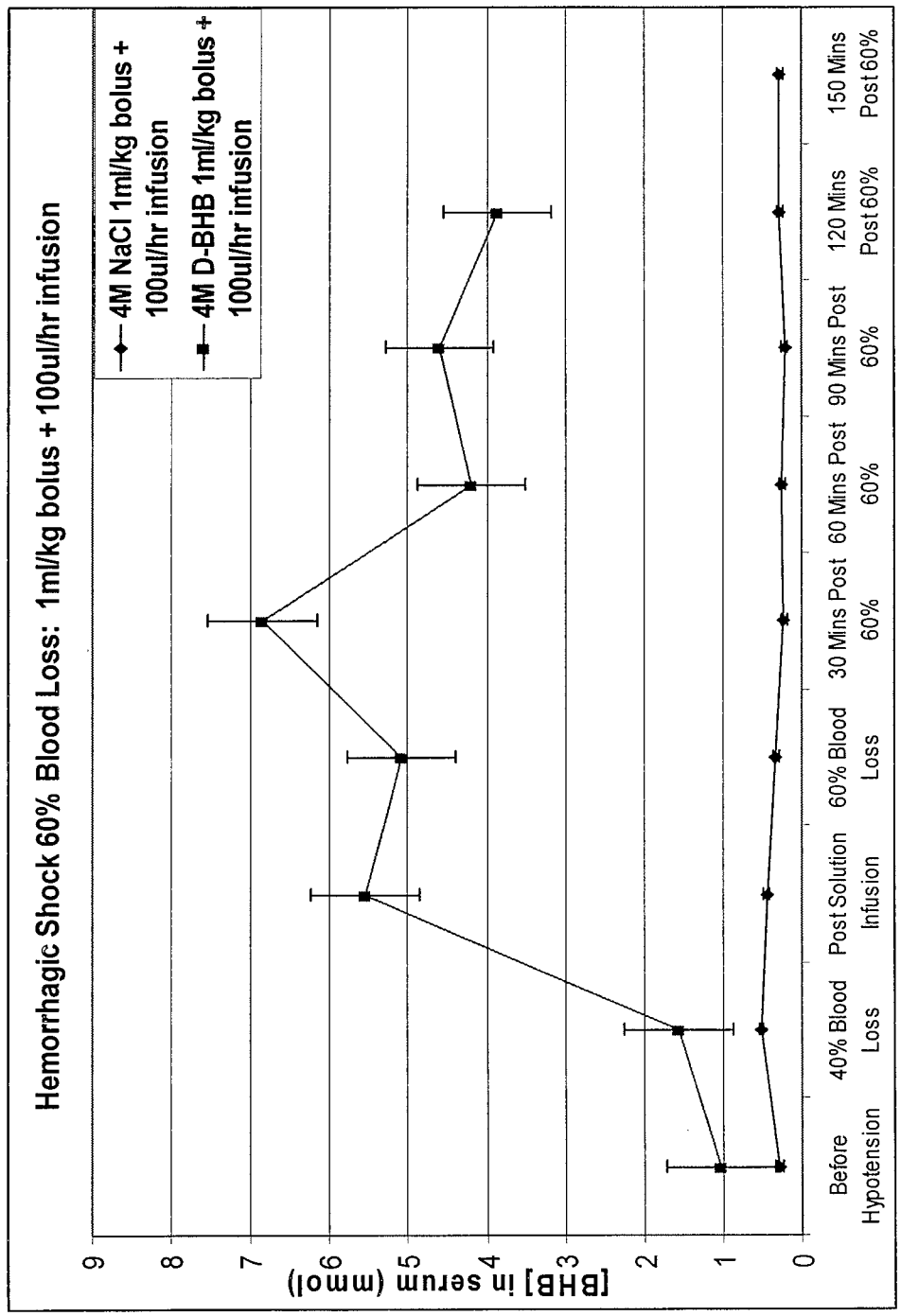
FIG. 11 shows a graph of serum levels of beta-hydroxybutyrate following administration of 1 ml/kg followed by 100 µl/hr infusion. Samples were calculated in triplicate in order to minimize pipetting error and are given in mM concentrations. Error bars are standard errors of the mean.

Serum was collected at the indicated time points and analyzed for the presence of D-BHB. Serum D-BHB levels were analyzed following a bolus administration of 1 ml/kg (FIG. 10) or following a bolus administration of 1 ml/kg and subsequent infusion of D-BHB at 100 μl/hr (FIG. 11).

Figure 12:
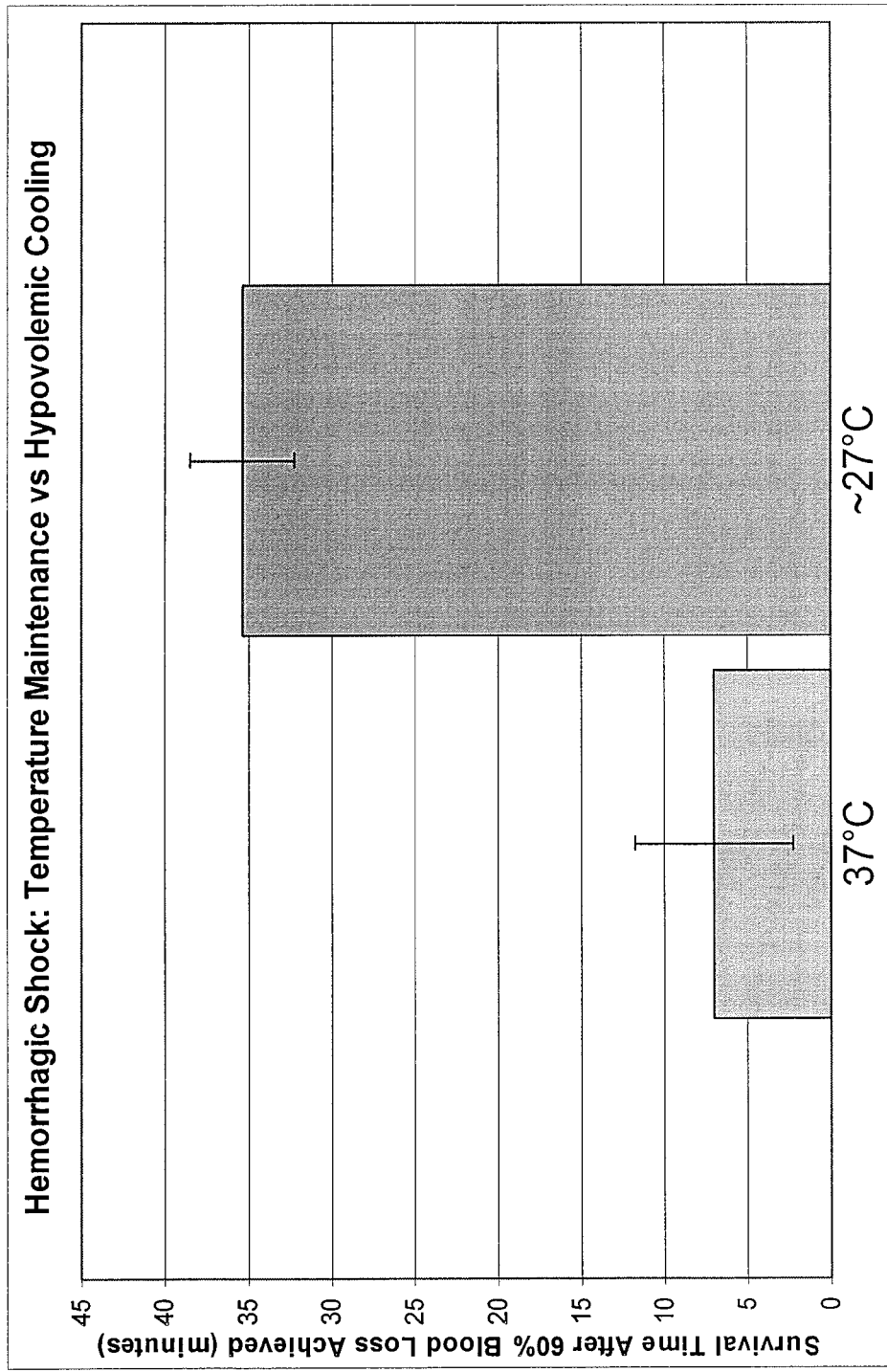
FIG. 12 is a graph showing the effect of temperature maintenance (left bar) vs. hypovolemic cooling (right bar) on survival following hemorrhagic shock. Error bars are standard error of the mean.

The effects of body temperature on animals that have experienced hemorrhagic shock were examined. Animals that experienced hemorrhagic shock and were artificially maintained at 37° C. via a feedback heating lamp mechanism (FIG. 12, left bar) expired significantly faster than animals allowed to drift to ambient temperature (FIG. 12, right bar). Animals that were allowed to drift toward ambient temperature survived on average, three times longer than animals with body temperatures of 37° C. (FIG. 12). It is noted that animals that were allowed to drift to ambient temperature never cooled below 27° C.

Figure 13:
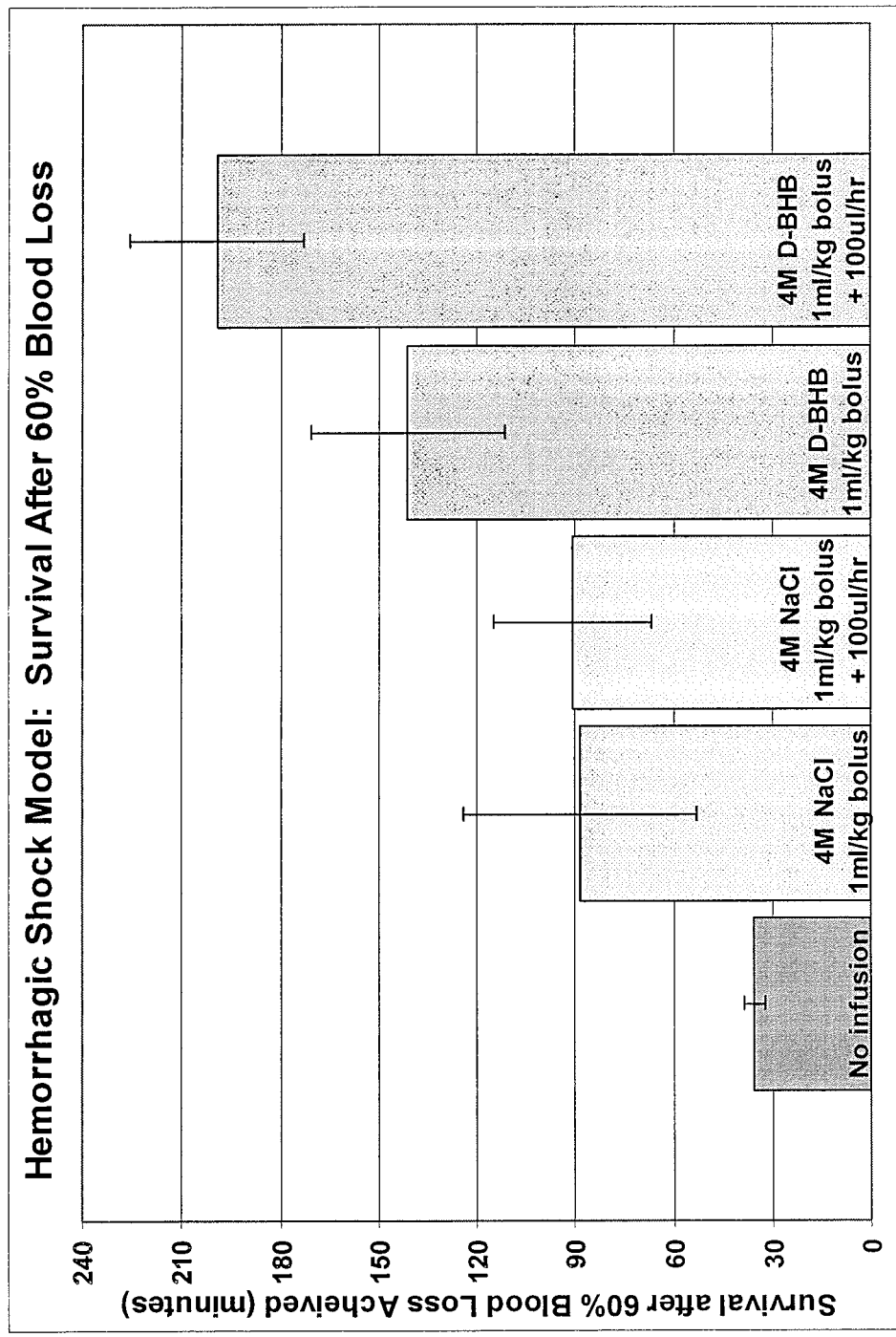
FIG. 13 shows the effects of various administration regimens on survival following hemorrhagic shock. Error bars are standard errors of the mean.

The effect of various compositions on the survival of animals that have experienced hemorrhagic shock was examined. Animals were administered a 1 ml/kg bolus of 4 M D-BHB or 4 M NaCl or a 100 μl bolus followed by 100 μl/hr infusion of 4M D-BHB or 4 M NaCl. Following 60% blood loss, animals were allowed to drift down to ambient temperature and were not artificially kept at 37° C. The shed blood was returned after 1 hr at 60% blood loss, and the rats were monitored for survival. Animals that received D-BHB survived longer than animals that received NaCl at the same osmolarity. Importantly, the animals given a bolus of D-BHB followed by an infusion of D-BHB lived significantly longer (p-value<0.016) than the animals given NaCl (FIG. 13).

Figure 14:
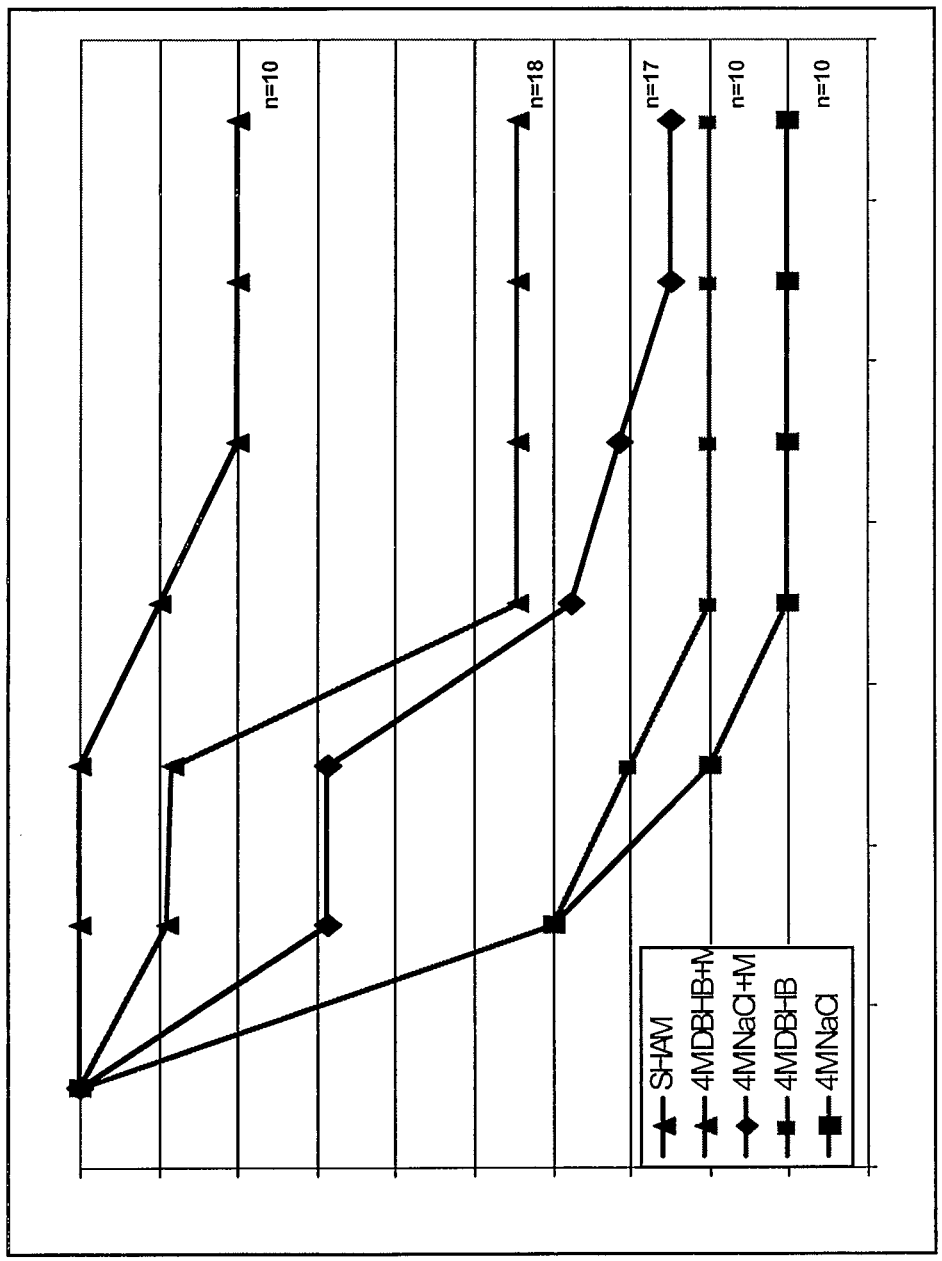
FIG. 14 shows Kaplan-Meyer survival plot of rats given the indicated treatment in conjunction with 60% blood loss for one hour. After one hour of 60% blood loss the shed blood was returned and the animals were monitored for survival. Sham animals were anesthetized and cannulated but no blood was removed.
Figure 15:
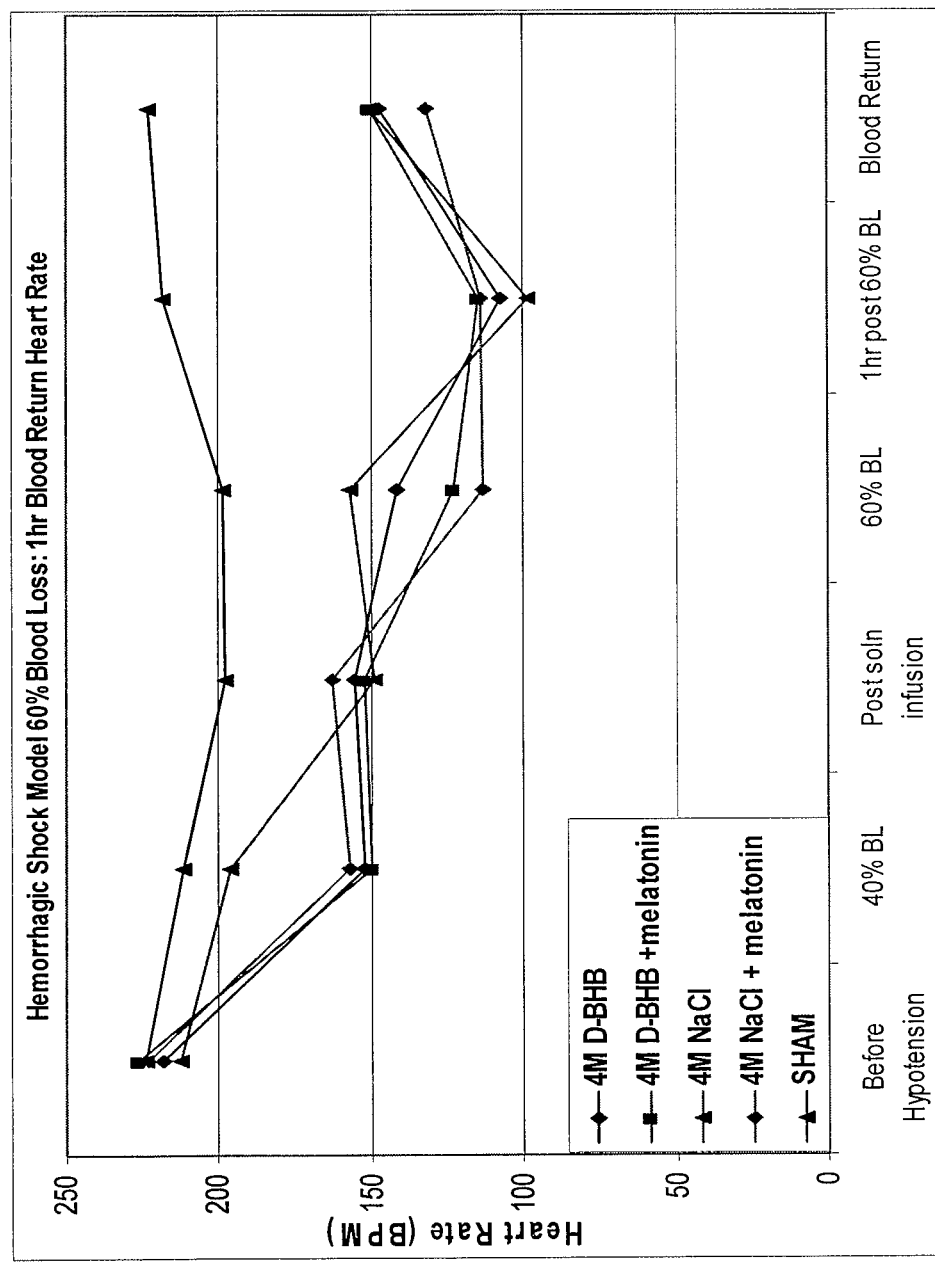
FIG. 15 is a graph showing the effect of the indicated treatment on heart rate.
Figure 16:
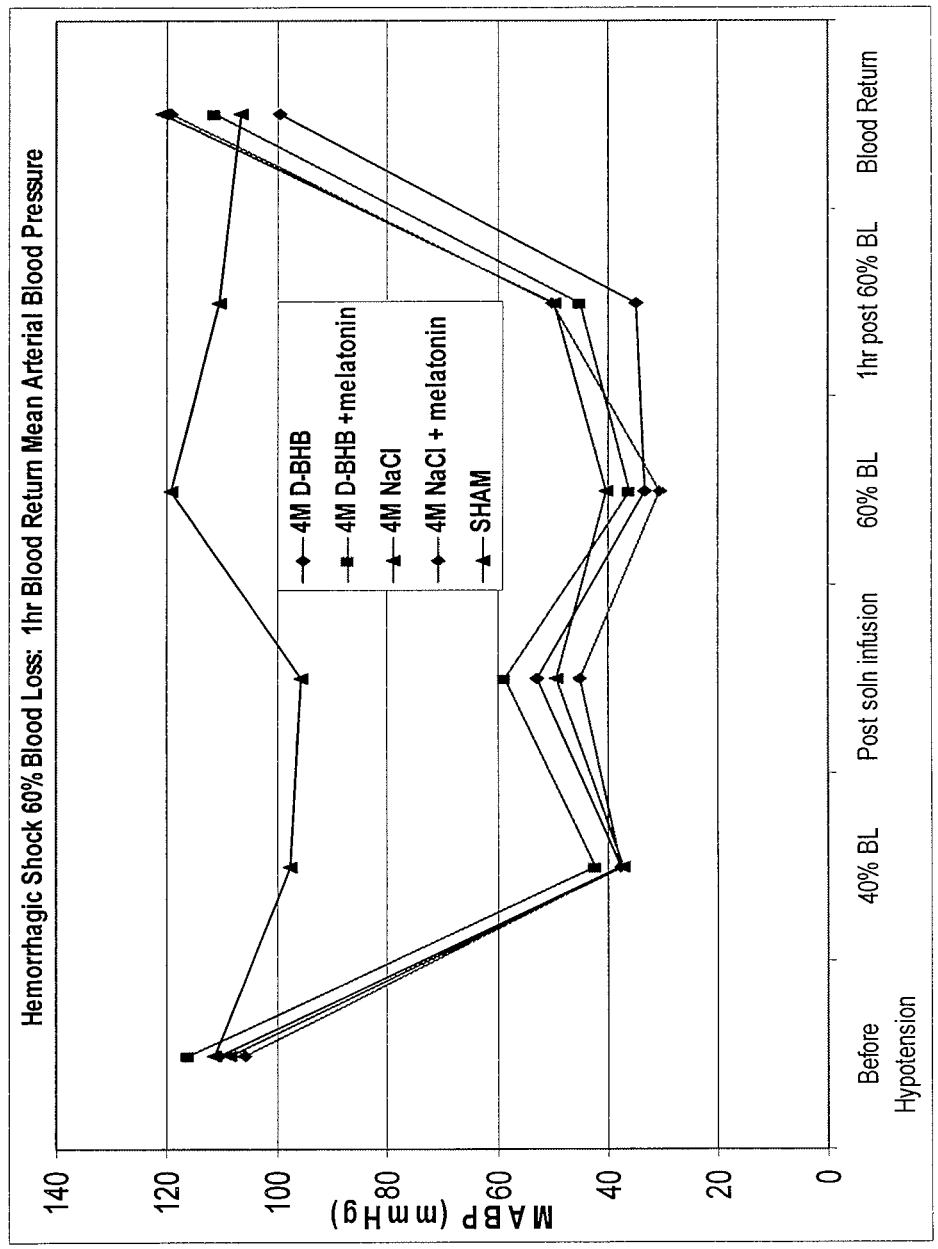
FIG. 16 is a graph showing the effect of the indicated treatment on the mean arterial blood pressure.
Figure 17:
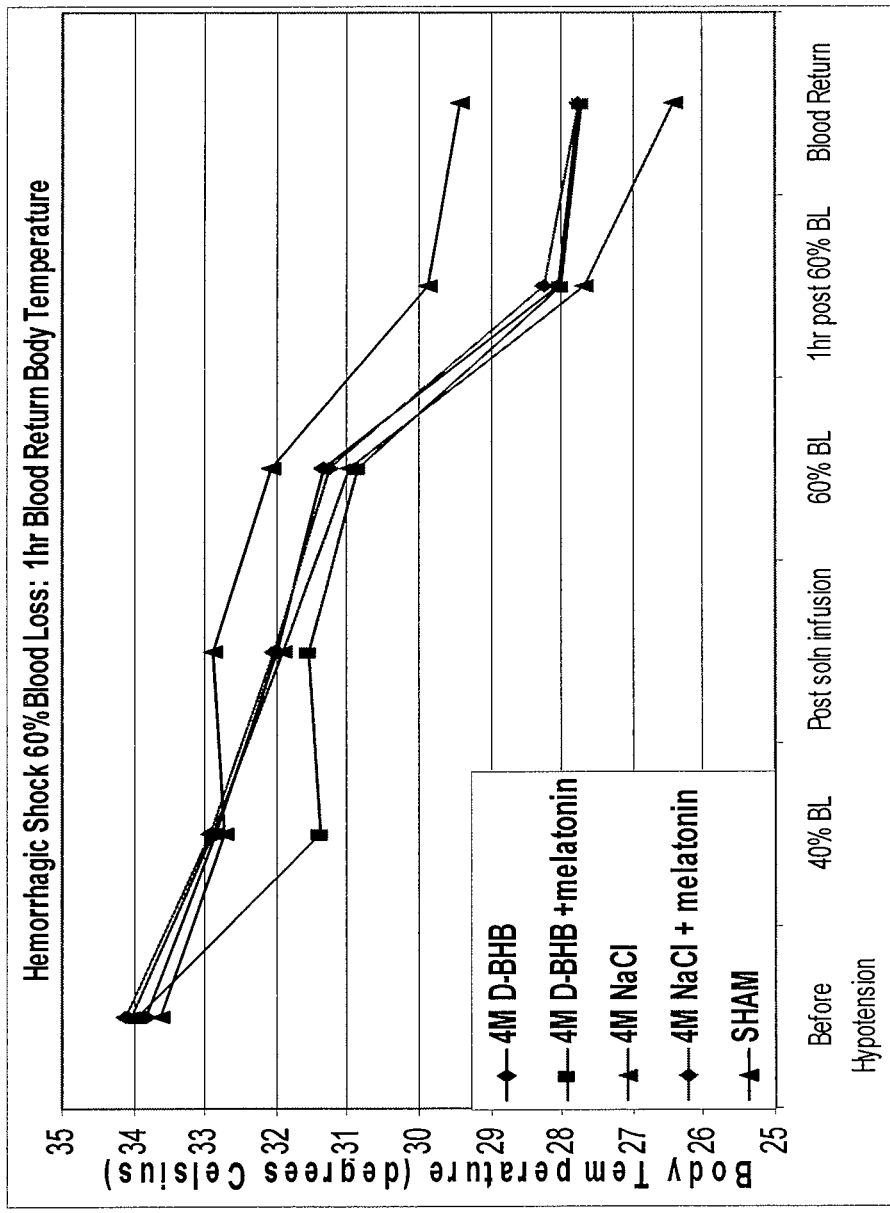
FIG. 17 is a graph showing the effect of the indicated treatment on body temperature.
Figure 19:
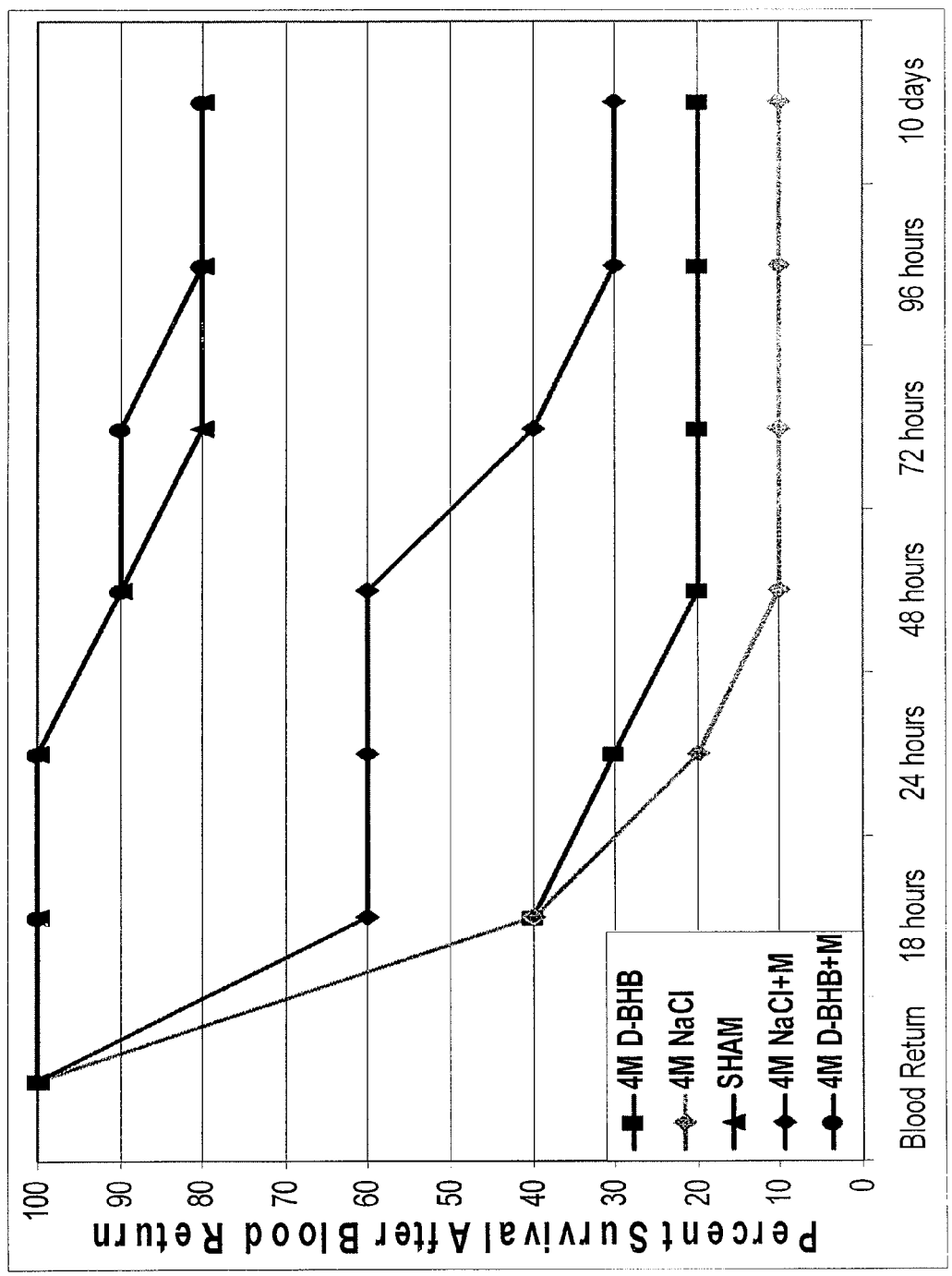
FIG. 19 shows Kaplan-Meyer survival curves for groups of rats that were subjected to 60% blood loss and administered either an ischemia/reperfusion protection composition containing 4M D-BHB and 43 mM melatonin (4M D-BHB+M) or a control solution containing 4M D-BHB, 4M NaCl, or 4M NaCl plus 43 mM melatonin (4M NaCl+M). The sham animals (SHAM) were not subjected to blood loss other than blood sampling, but were put under anesthesia, cannulated, and allowed to recover for the same amount of time as the animals in the other groups. Blood return=time at which shed blood was returned; 18 hours, 24 hours, 48 hours, 72 hours, 96 hours, and 10 days=18 hours, 24 hours, 48 hours, 72 hours, 96 hours, and 10 days after return of shed blood, respectively. Time points on the x-axis are not plotted to scale.

Significant additional benefits to survival after blood return were seen when 43 mM melatonin was added to the 4 M D-BHB (FIGS. 14 and 19). During the blood loss, heart rate (FIG. 15), mean arterial blood pressure (MABP; FIG. 16) and body temperature (FIG. 17) of the animals were monitored.

Additionally, at day 1-6 post-surgery, rats underwent neurological scoring; at 7-10 days post-surgery, rats underwent memory testing; and at day 10 post-surgery, rats were sacrificed and brain histology was performed.

SUMMARY

Animals given the ketone based solution of 4 M D-BHB survived longer following hemorrhagic shock than their counterparts given 4 M NaCl. In addition, animals artificially kept at 37° C. with a feedback lamp died considerably faster than animals allowed to drift to room temperature. Animals that were allowed to drift to ambient temperature survived, on average, over three times longer than the heat maintained animals. This suggests that mild hypothermia is important in regards to survival of hemorrhagic shock, and demonstrates the effect of temperature upon survival at 60% blood loss.

Example 4

Additional Experiments Regarding Significant Blood Loss in Rats

In additional experiments, an ischemia/reperfusion protection composition comprising 4M D-BHB and 43 mM melatonin in an aqueous solution containing 20% DMSO was compared with control solutions in a rat model of hemorrhagic shock as described in Example 3. The control solutions were aqueous solutions containing 20% DMSO and (1) 4M D-BHB, (2) 4M NaCl, or (3) 4M NaCl and 43 mM melatonin.

The solutions were prepared as described in Example 3 except that the melatonin/100% DMSO stock solution described in Example 3 was diluted by cutting the melatonin concentration in half, and twice the volume of melatonin stock solution was used to prepare solutions for infusion into a rat. The solutions for infusion contained 20% DMSO (instead of 10% DMSO as described in Example 3).

Typically, rats had lost about 40% of their blood at about 10 minutes after initiation of bleeding. After about 40% blood loss was achieved, the rats were infused with a 1 mL/kg bolus dose of ischemia/reperfusion protection composition containing D-BHB plus melatonin or a control solution. The bolus infusion occurred over a time span of about 10 minutes, after which a continuous infusion (100 µL/hour) of ischemia/reperfusion protection composition containing D-BHB and melatonin or a control solution was initiated. The blood pressure was further lowered for about the next 10 minutes until the total amount of shed blood was equal to about 60% of total blood. Infusion (100 µL/hour) of ischemia/reperfusion protection composition containing D-BHB and melatonin or control solution was continued until one hour after about 60% blood loss was achieved. Return of shed blood was then initiated. The endpoint of the study was death following blood return, or euthanasia after ten days of observation.

Figure 20:
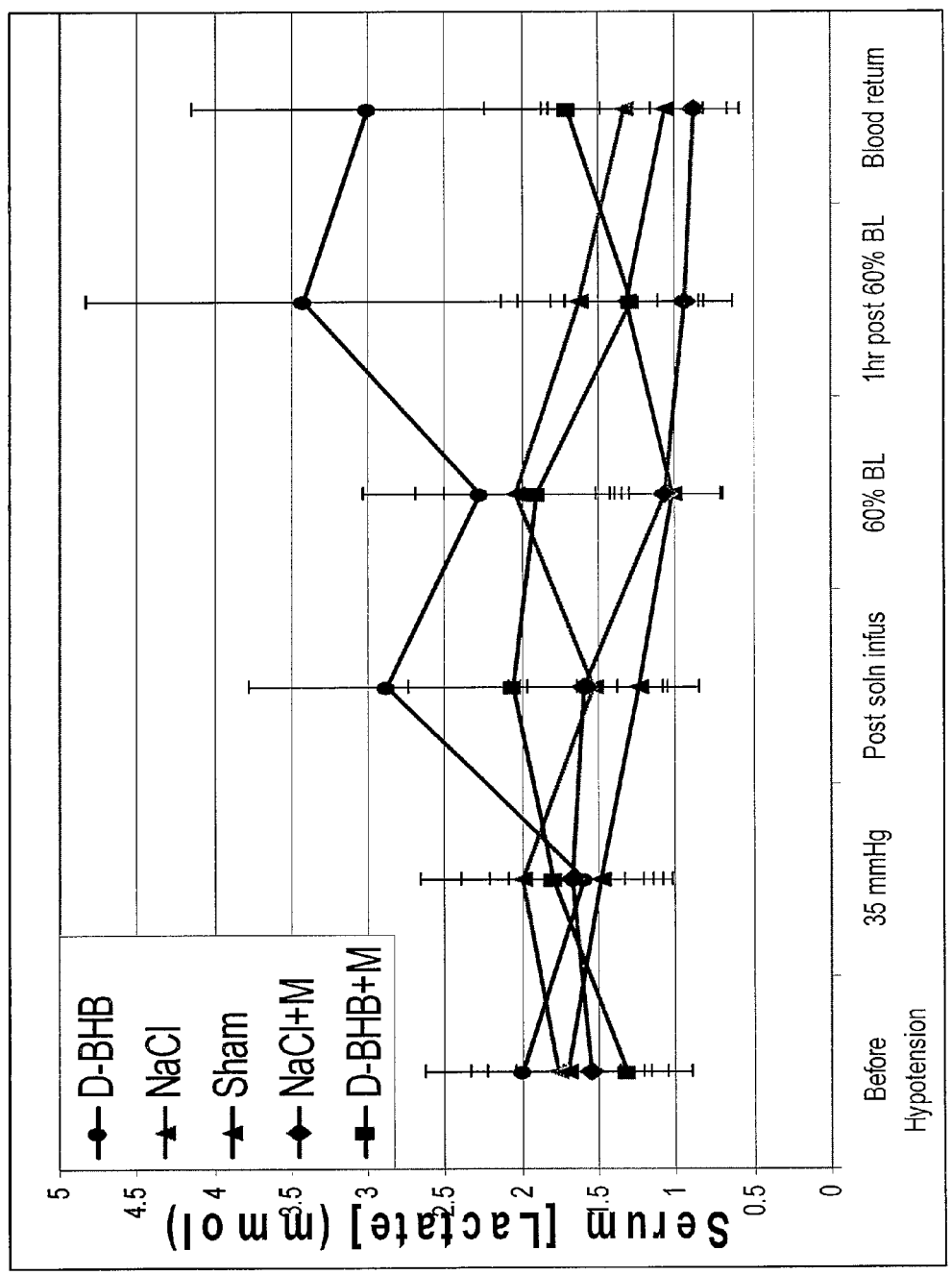
FIG. 20 is a graph plotting average lactate levels measured at various time points in serum from rats that were subjected to 60% blood loss and administered either an ischemia/reperfusion protection composition containing D-BHB and melatonin (4M D-BHB+M) or a control solution containing 4M D-BHB, 4M NaCl, or 4M NaCl plus melatonin (4M NaCl+M). There were 10 animals in each treatment group. The sham animals (SHAM) were not subjected to blood loss other than blood sampling, but were put under anesthesia, cannulated, and allowed to recover for the same amount of time as the animals in the other groups. Before hypotension=prior to blood loss; 35 mm Hg=about 40% blood loss; Post soln infus=post solution infusion; 60% BL=60% blood loss; 1 hr post 60% BL=one hour post 60% blood loss; blood return=time at which shed blood was returned.

The results of these studies showed that survival of rats subjected to 60% blood loss was dramatically increased in rats infused with ischemia/reperfusion protection composition containing D-BHB and melatonin, as compared to rats infused with a control solution containing 4M D-BHB, 4M NaCl, or 4M NaCl plus melatonin (FIG. 19). Indeed, there was no significant difference between rats treated with ischemia/reperfusion protection composition containing D-BHB plus melatonin and sham treated rats that were not subjected to blood loss. Serum lactate concentrations were not observed to differ significantly between any of the treatment groups (FIG. 20).

Example 5

Protection of Large Animals from Significant Blood Loss

Objective

The effectiveness of an ischemia/reperfusion protection composition is tested in a clinically-relevant large animal model of hemorrhagic shock. A controlled model of hemorrhagic shock is employed, which uses systolic blood pressure of 50 mm Hg as a bleeding endpoint to simulate large vessel injury and clot formation. See, for example, Skarda et al., 2006, *J. Amer. Coll. Surg.*, 203(3S):S32-S33.

Two groups of animals are used, and are treated to simulate a real life environment. Animals undergo the hemorrhagic shock protocol and then receive either ischemia/reperfusion protection composition or carrier solution intravenously 15 minutes after hemorrhage to simulate initial therapy by first-responders in the field. To simulate arrival at a treatment facility, all animals receive resuscitation using a standard protocol after 1.5 hours of shock. Animals are resuscitated to standard clinical endpoints of blood pressure, urine output, and hemoglobin for 8 hours, and then sacrificed for analysis.

TABLE 2

Measured endpoints during hemorrhagic shock/resuscitation

| | |
|---|---|
| Physiologic parameters | Oxygen delivery ($DO_2$) & consumption ($VO_2$), urine output, heart rate, blood pressure, cardiac output, pulmonary capillary wedge pressure (PCWP) |
| Near-infrared spectroscopy measures | Tissue oxyhemoglobin saturation ($StO_2$) skeletal muscle, stomach, liver |
| BIS monitor | Sedation measurements while under anesthesia |
| Laboratory measures | Lactate, BUN, creatinine, AST, ALT, alk phos, bilirubin, LDH, CPK, blood glucose, arterial and venous blood gasses |
| Indices of resuscitation | Fluid consumption, blood transfusion |

Primary endpoints of the experiments are parameters of adequacy of tissue perfusion. These include lactate level, base deficit, and $StO_2$. Lactate and base deficit are recognized, widely used endpoints for clinical resuscitation of trauma patients, while $StO_2$, a parameter measuring oxygen saturation in tissue hemoglobin, has been shown to correlate with oxygen delivery in trauma models. In a recent observational trial of severely-injured trauma patients, $StO_2$ predicted mortality as well as lactate and base deficit. Other parameters are listed in Table 2, and are recorded during the experiment as noted in Table 3.

TABLE 3

| | Baseline | Shock 30, 60, 90 | 1 hr resus | 2 hour resus | 4 hour resus | 6 hour resus | 8 hour resus |
|---|---|---|---|---|---|---|---|
| Invasive Hemodynamics[a] | x | x | x | x | x | x | x |
| Laboratory measures | x | x | x | x | x | x | x |
| NIR parameters (mm, gut, liver) | x | x | x | x | x | x | x |
| Muscle, liver biopsy | x | Shock 90 | | | | | x |

Experimental Protocol

Animals are anesthetized using a combination of althesin and ketamine. Animals receive anesthesia during initial surgery and during the shock period utilizing a protocol consisting of althesin, a steroid anesthetic (Schering-Plough Animal Health, Kenilworth, N.J.) and nitrous oxide, a combination that has been shown to preserve many of the body's reflex responses to shock while allowing an appropriate level of anesthesia. Animals are ventilated using mechanical ventilation through endotracheal tube with $FiO_2$ adjusted to $PaO_2$ of 80-120 mm Hg and $PaCO_2$ of 37-43 mm Hg during preparatory surgery. Preparatory surgery includes laparotomy for splenectomy (to prevent autotransfusion), cannulation of the IVC, and bladder catheterization. Arterial and pulmonary artery catheters are placed via neck cutdown. After a stabilization period, hemorrhagic shock is induced by withdrawal of blood into heparinized blood bags to obtain a systolic blood pressure of 50 mm Hg. After 15 minutes of shock, animals receive intravenously either an ischemia/reperfusion protection composition having either D-BHB and melatonin or acetoacetic acid and melatonin, or carrier solution.

After 90 minutes of shock, animals are started on a weight-based infusion of ischemia/reperfusion protection composition or carrier solution. Additionally, animals are resuscitated to clinical endpoints using a standard resuscitation strategy as outlined in FIG. 18. Throughout the shock and resuscitation periods, animals are maintained on the ventilator and receive adjusted-dose propofol and nitrous oxide to maintain an appropriate level of sedation and comfort using BIS monitor. Surviving animals are euthanized 8 hours after resuscitation is initiated.

Example 6

Protection of Large Animals from Significant Blood Loss

The effectiveness of an ischemia/reperfusion protection composition containing D-BHB plus melatonin was tested in a pig model of hemorrhagic shock described elsewhere (Example 5; Beilman et al., 1999, Shock, 12(3):196-200; Skarda et al., 2007, Resuscitation, 75(1):135-44; Taylor et al., 2004, Shock, 21(1):58-64; Taylor et al., 2004, J. Trauma, 56(2):251-258; Mulier et al., 2005, Shock, 23(3):248-52; Skarda et al., 2006, J. Amer. Coll. Surg., 203(3):S32-S33; Taylor et al., 2005, J. Trauma, 58(6):1119-25). A pig model was selected because of its acceptance as a clinically relevant model for human hemorrhagic shock. Blood loss to a systolic blood pressure of about 50 mm Hg was used to trigger the vascular decompensation observed in trauma patients suffering from severe blood loss.

Experiments were performed essentially as set forth in Example 5. Two experimental groups of pigs underwent hemorrhagic shock and received treatment simulating a real life situation. One group of pigs received an ischemia/reperfusion protection composition comprising 4M D-BHB and 43 mM melatonin in an aqueous solution containing 20% DMSO. The other group received a control solution containing 4M NaCl and 20% DMSO. Solutions were administered via a central venous catheter (administration of the ischemia/reperfusion protection composition via a peripheral vein can result in some necrosis of the localized tissue).

Each pig was administered a bolus infusion of 1 mL/kg of ischemia/reperfusion protection composition or control solution at 15 minutes after hemorrhage to simulate initial treatment by emergency medical personnel at the scene. Immediately following the bolus infusion, each of the two groups of pigs was further divided into one of three dosing groups. One dosing group was administered a continuous infusion of 0.66 mL/kg/hour of ischemia/reperfusion protection composition or control solution until four hours after resuscitation (high dose). A second dosing group was administered a continuous infusion of 0.33 mL/kg/hour of ischemia/reperfusion protection composition or control solution until four hours after resuscitation (medium dose). A third group was not administered a continuous infusion immediately following the bolus infusion (at 15 minutes after shock), but was administered a continuous infusion of 0.33 mL/kg/hour of ischemia/reperfusion protection composition or control solution beginning at 60-90 minutes after shock (at the time of resuscitation) and continuing until four hours after resuscitation (low dose).

Figure 18:
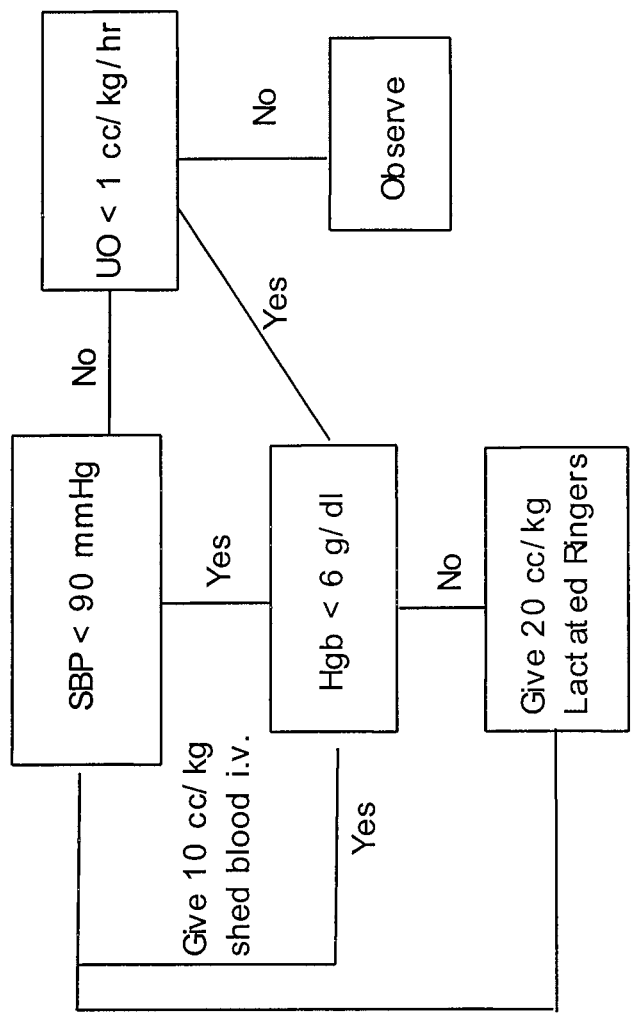
FIG. 18 shows a resuscitation strategy for porcine hemorrhagic shock. SBP=systolic blood pressure; UO=urine output; Hgb=hemoglobin.

To simulate arrival at a treatment facility, all animals were resuscitated after 60-90 minutes of shock. Resuscitation began when animals developed a lactate level >8 mg/dl, exhibited a drop in tissue hemoglobin oxygen saturation (StO2) below 50%, and displayed signs of loss of vasomotor tone (systolic blood pressure dropped more than 10 mm Hg). The animals were resuscitated to standard clinical endpoints of blood pressure, urine output, and hemoglobin (FIG. 18). After eight hours of resuscitation, the animals were sacrificed.

Figure 21:
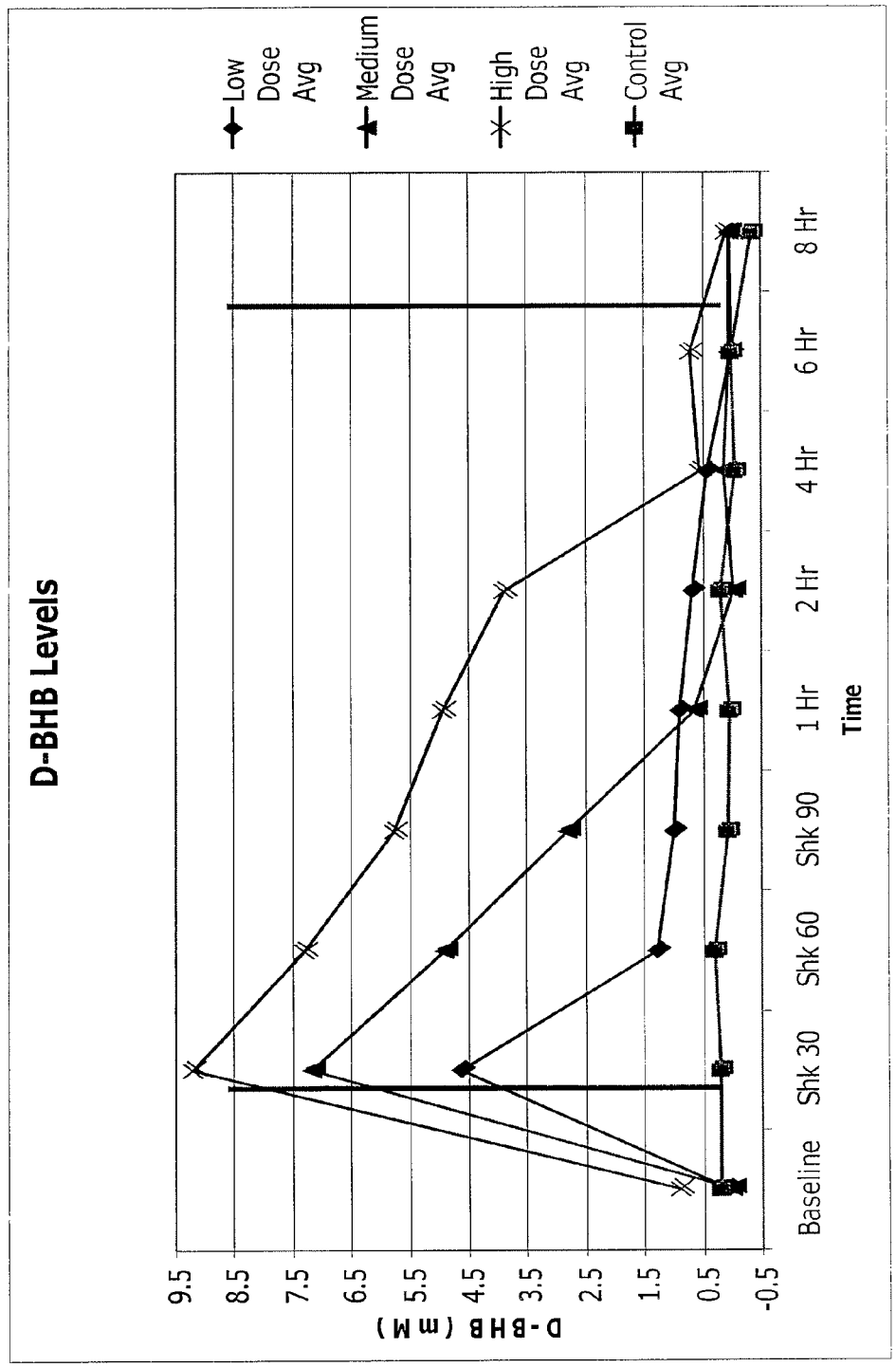
FIG. 21 is a graph plotting levels of D-BHB (mM) measured at numerous time points in serum from pigs that were subjected to blood loss and administered a low, medium, or high dose of ischemia/reperfusion protection composition comprising D-BHB plus melatonin. Serum D-BHB levels in control pigs also are plotted. Shk 30, 60, 90=30, 60, and 90 minutes after shock, respectively. 1 Hr, 2 Hr, 4 Hr, 6 Hr, and 8 Hr=1, 2, 4, 6, and 8 hours after initiation of resuscitation, respectively. The left and right vertical lines indicate the beginning and end, respectively, of fluid administration.

Serum levels of D-BHB (mM) were measured in control pigs as well as pigs that were administered a low, medium or high dose of the ischemia/reperfusion protection composition. Levels were measured at baseline; at 30, 60, and 90 minutes after shock; and at 1, 2, 4, 6, and 8 hours after initiation of resuscitation (FIG. 21). These results indicated that the serum D-BHB levels observed in pigs that were administered the ischemia/reperfusion protection composition were similar to the serum D-BHB levels observed in rats that were administered the ischemia/reperfusion protection composition (compare FIG. 21 with FIG. 11). The results of these experiments indicate that the ischemia/reperfusion protection composition comprising D-BHB plus melatonin was safe in the pig hemorrhagic shock model and improved the important clinical measurements monitored during resuscitation.

Figure 22:
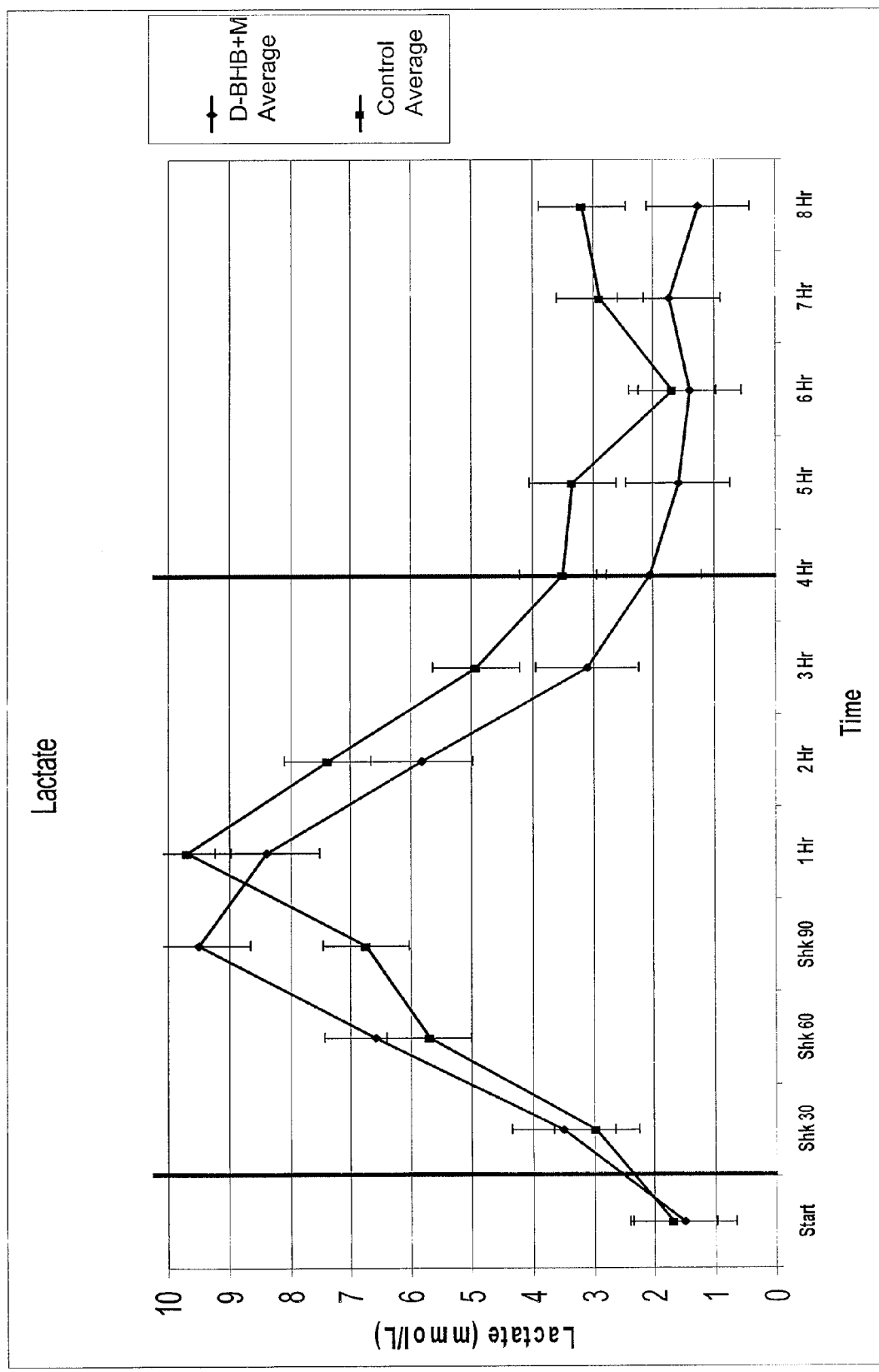
FIG. 22 is a graph plotting average lactate levels (mmol/L) measured at several time points in serum from pigs that were subjected to blood loss and treated with ischemia/reperfusion protection composition or control solution. Shk 30, Shk 60, and Shk 90=30, 60, and 90 minutes after shock, respectively. 1 Hr, 2 Hr, 3 Hr, 4 Hr, 5 Hr, 6 Hr, 7 Hr, and 8 Hr=1, 2, 3, 4, 5, 6, 7, and 8 hours post-resuscitation, respectively. The left and right vertical lines indicate the start and stop times, respectively, of fluid administration.

One of the primary endpoints measured during the pig hemorrhagic shock experiments was the level of lactate in the serum (FIG. 22). Serum lactate level is an indicator of the adequacy of tissue perfusion that is widely used as an endpoint for clinical resuscitation of trauma patients. Numerous studies have shown that patients who are going to survive traumatic shock normalize their lactate levels more quickly than those who are not going to survive. Lactate buildup in the blood can be a prognostic indicator of death. Lactate levels were observed to decline more rapidly in animals treated with the ischemia/reperfusion protection composition relative to controls (FIG. 22). It took six hours of resuscitation for the average lactate level in control animals to reach the same average lactate level found after only four hours of resuscitation in animals treated with the ischemia/reperfusion protection composition. These data indicate that tissue homeostasis following hemorrhagic shock was superior in pigs treated with the ischemia/reperfusion protection composition relative to the control animals. It is noted that measurements in pigs that received the ischemia/reperfusion protection composition were averaged together, as were measurements in pigs that received the control solution.

Figure 23:
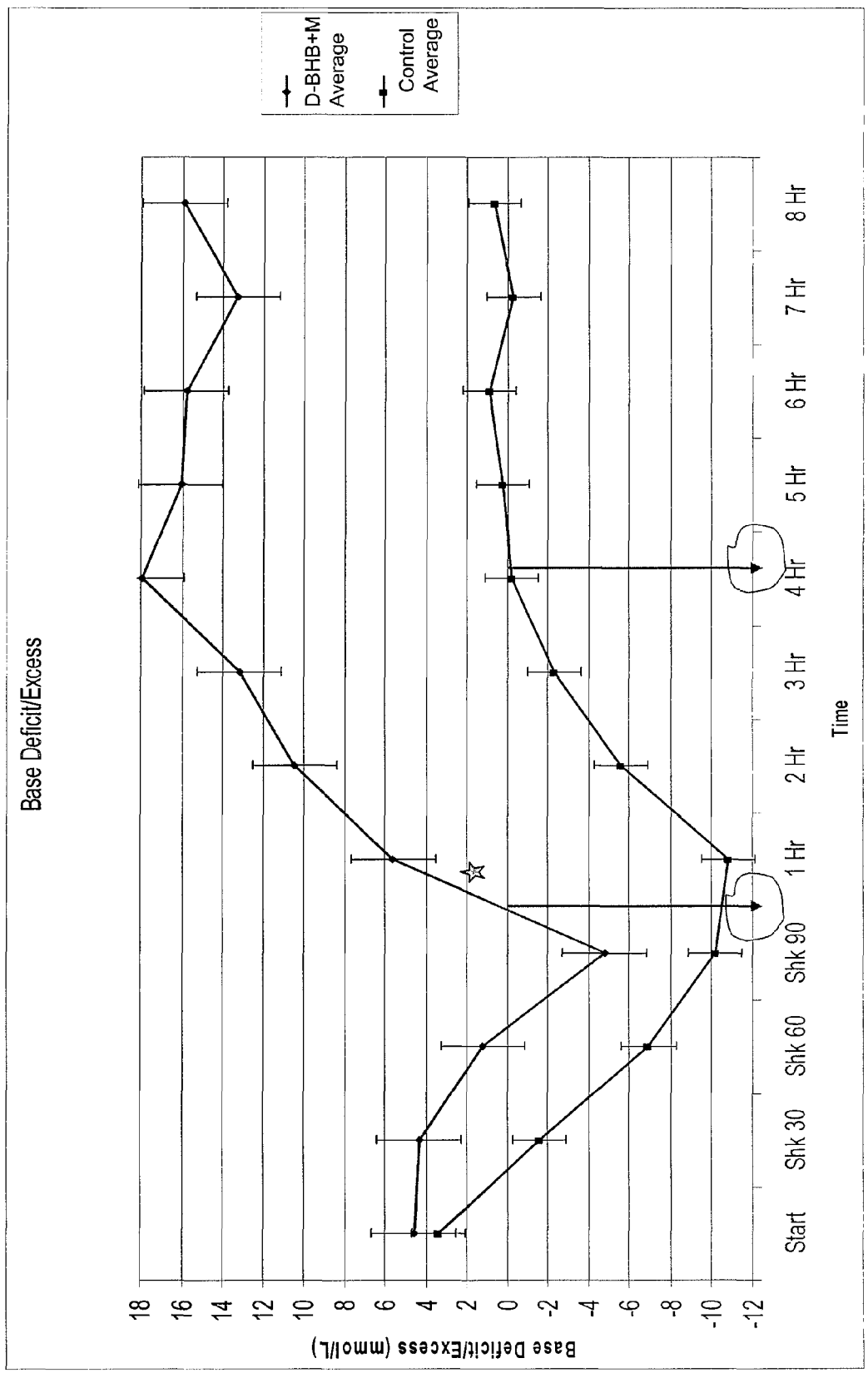
FIG. 23 is a graph plotting base deficit/excess values (mmol/L) at numerous time points in pigs that underwent hemorrhagic shock and were treated with ischemia/reperfusion protection composition or control solution. Start=time at which the hemorrhagic shock protocol was initiated; Shk 30, Shk 60, and Shk 90=30, 60, and 90 minutes after shock, respectively; 1 Hr, 2 Hr, 3 Hr, 4 Hr, 5 Hr, 6 Hr, 7 Hr, and 8 Hr=1, 2, 3, 4, 5, 6, 7, and 8 hours post-resuscitation, respectively.

Base deficit/excess is another parameter that was assessed during the large animal experiments (FIG. 23; Siggaard-Andersen, 1974, *The acid-base status of the blood*, 4$^{th}$ Ed., Copenhagen: Munksgaard; Schmelzer et al., 2008, *Am. J. Emerg. Med.*, 26:119-23; Eastridge et al., 2007, *J. Trauma*, 63:291-9; Englehart & Schreiber, 2006, *Curr. Opin. Crit. Care*, 12:569-74). Base deficit was measured using a blood gas analyzer (Gem Premier Model 3000 with Base Deficit Cartridge No. 24315009; Instrumentation Laboratories Inc., Lexington, Mass.). Like lactate level, base deficit/excess also is recognized as a measure of the adequacy of tissue perfusion and is widely used to assess clinical resuscitation of trauma patients. The base deficit that was reached at 90 minutes after the start of shock was not as severe in animals treated with the ischemia/reperfusion protection composition as that in animals administered the control solution (FIG. 23). In addition, the base deficit was observed to recover faster in the group treated with ischemia/reperfusion protection composition than in the control group. A base deficit of greater than 6 mEq/L, which was observed beginning at about 45 minutes after shock and lasting until about 2 hours after resuscitation in the control group but not in the group treated with the ischemia/reperfusion protection composition, is a predictor of mortality (Cohn et al., 2007, *J. Trauma*, 62(1):44-54).

Taken together, the results presented in FIGS. 22 and 23 show that treatment with the ischemia/reperfusion protection composition comprising D-BHB and melatonin was associated with a trend toward more rapid clearance of lactate and base deficit. These results provide strong evidence that treatment with ischemia/reperfusion protection composition can lower mortality and improve outcome for human trauma patients.

Figure 24:
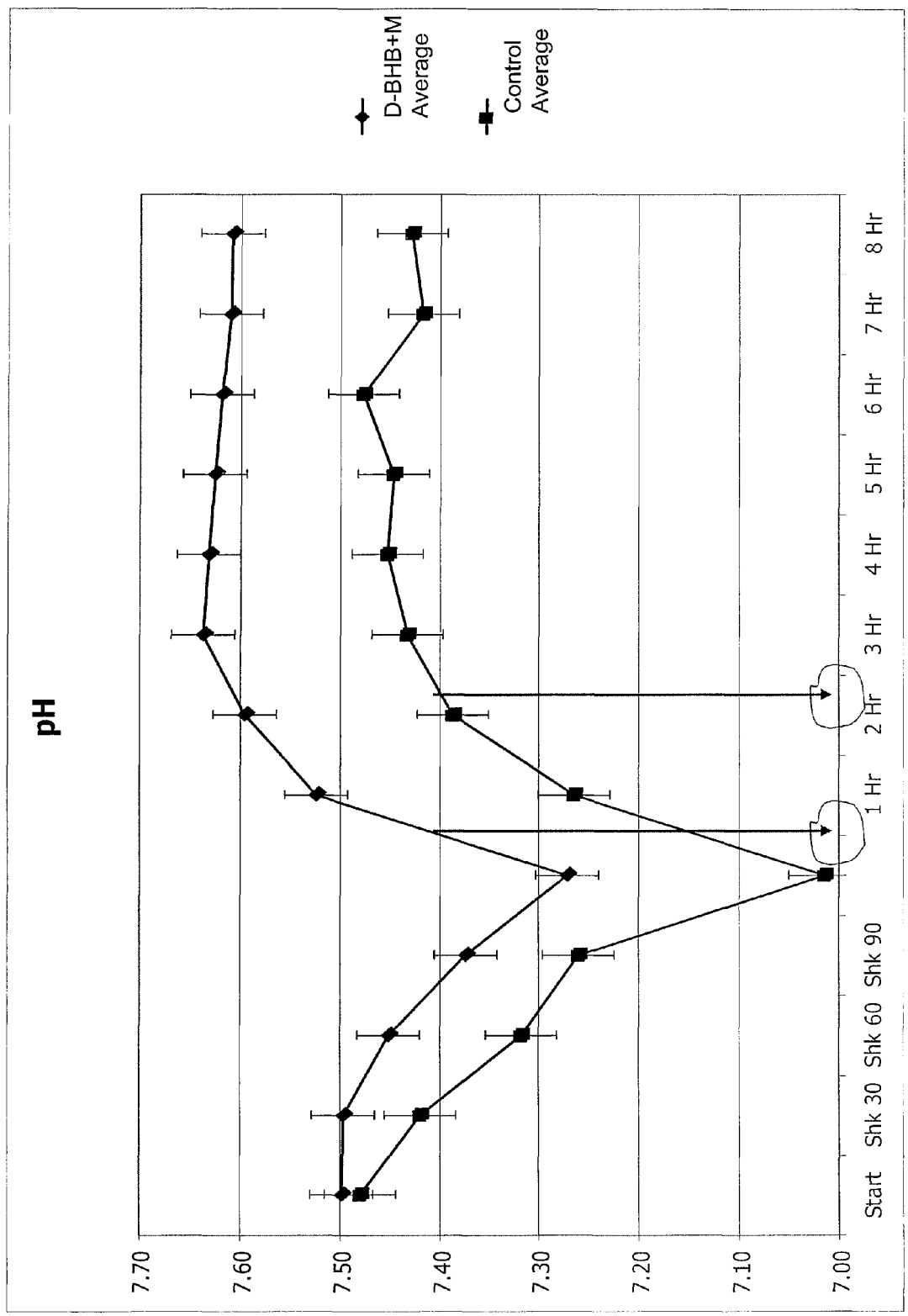
FIG. 24 is a graph plotting pH values measured at several time points in serum from pigs that underwent hemorrhagic shock and were treated with ischemia/reperfusion protection composition or control solution. Start=time at which the hemorrhagic shock protocol was initiated; Shk 30, Shk 60, and Shk 90=30, 60, and 90 minutes after shock, respectively; 1 Hr, 2 Hr, 3 Hr, 4 Hr, 5 Hr, 6 Hr, 7 Hr, and 8 Hr=1, 2, 3, 4, 5, 6, 7, and 8 hours post-resuscitation, respectively.

Serum pH values also were measured in pigs that were administered the ischemia/reperfusion protection composition or the control solution (FIG. 24). In animals treated with ischemia/reperfusion protection composition, the serum pH levels did not drop as low as in the control animals. In addition, the pH levels in animals treated with ischemia/reperfusion protection composition were observed to normalize faster relative to the control animals.

Figure 25:
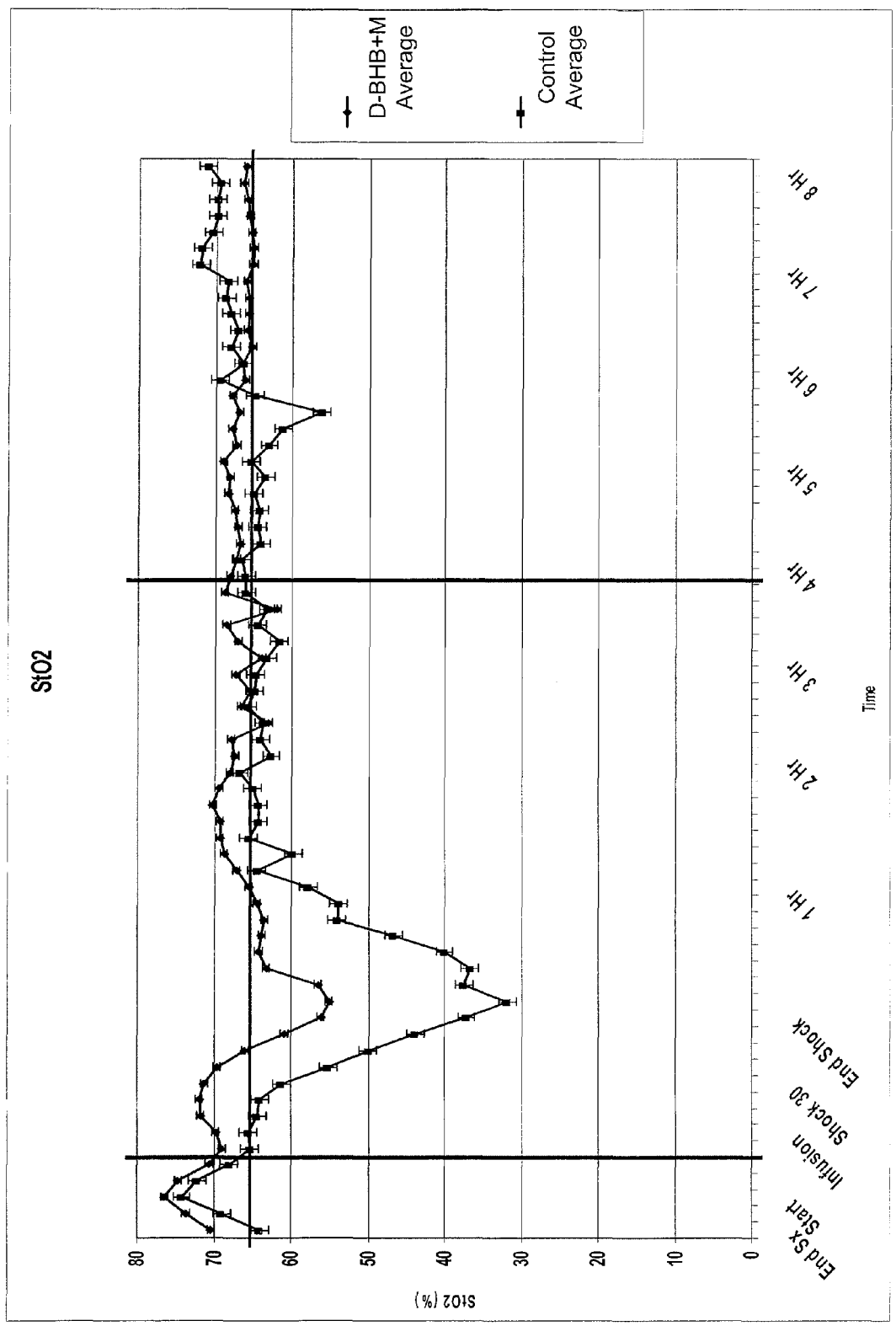
FIG. 25 is a graph plotting peripheral tissue perfusion (StO2; %) measured at several time points in pigs that were hemorrhagically shocked and treated with ischemia/reperfusion protection composition or control solution. End Sx=stabilization of animals prior to shock; Start=start of hemorrhagic shock protocol; Infusion=initiation of infusion with ischemia/reperfusion protection composition or control solution; Shock 30=30 minutes after shock; End Shock=time at which the systolic pressure was about 50 mmHg; 1 Hr, 2 Hr, 3 Hr, 4 Hr, 5 Hr, 6 Hr, 7 Hr, and 8 Hr=1, 2, 3, 4, 5, 6, 7, and 8 hours post-resuscitation, respectively. The vertical left and right vertical lines indicate the start and stop, respectively, of infusion with ischemia/reperfusion protection composition or control solution.
Figure 26:
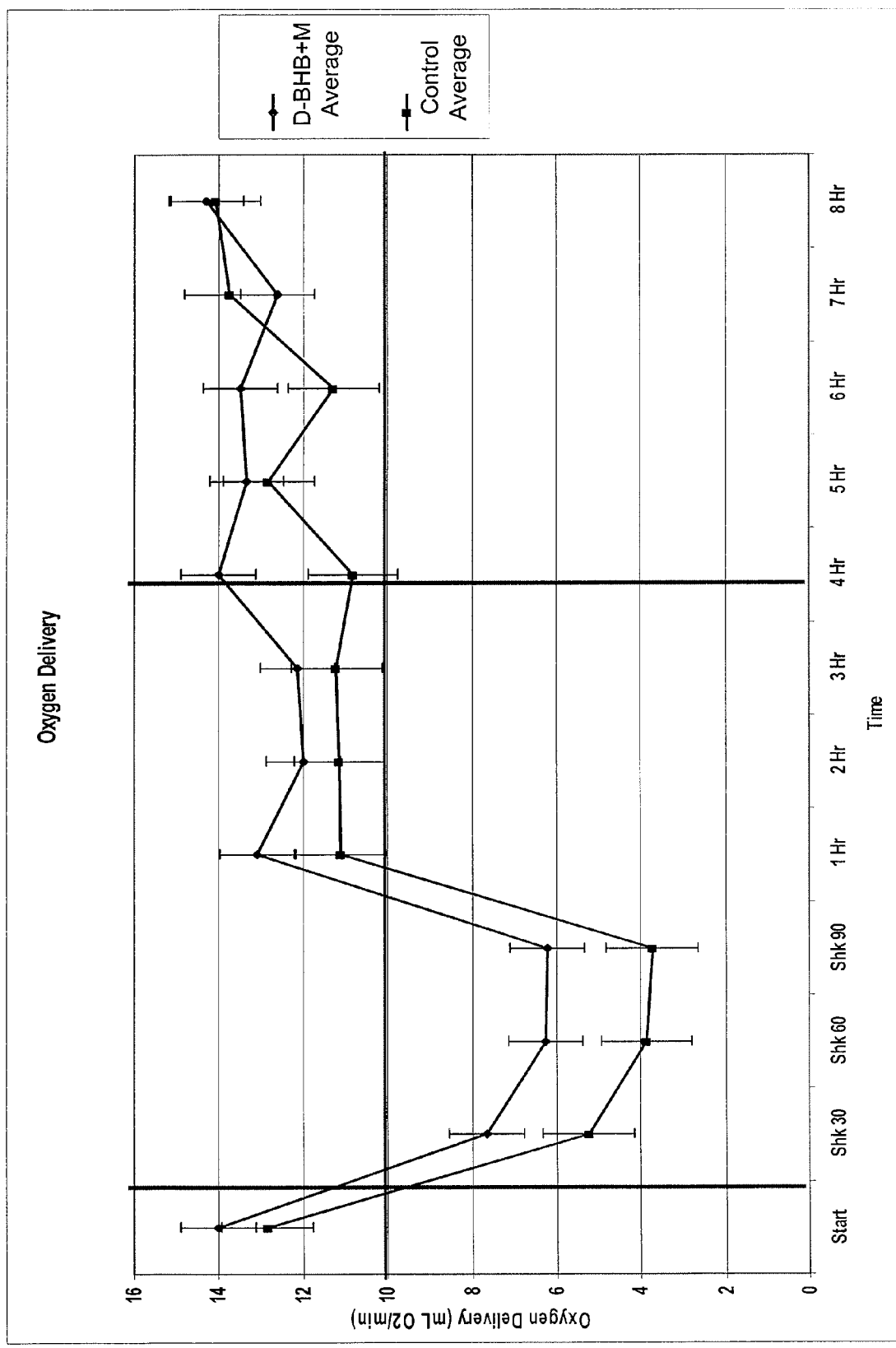
FIG. 26 is a graph plotting oxygen delivery (mL $O_2$ per minute) at several time points in pigs that underwent hemorrhagic shock and were administered ischemia/reperfusion protection composition or control solution. Start=time at which the hemorrhagic shock protocol was initiated; Shk 30, Shk 60, and Shk 90=30, 60, and 90 minutes after shock, respectively; 1 Hr, 2 Hr, 3 Hr, 4 Hr, 5 Hr, 6 Hr, 7 Hr, and 8 Hr=1, 2, 3, 4, 5, 6, 7, and 8 hours post-resuscitation, respectively.

The adequacy of tissue perfusion also was evaluated by measuring the tissue oxyhemoglobin saturation (StO$_2$; FIG. 25; Zenker et al., 2007, *J. Trauma*, 63:573-80; Puyana & Pinsky, 2007, Crit. Care, 11:116; Cohn et al., 2007, *J. Trauma*, 62:44-55; and Myers et al., 2005, *J. Biomed. Opt.*, 10:034017). StO$_2$ values indicate the oxygen saturation in tissue hemoglobin and have been shown to correlate with oxygen delivery in trauma models. In a study of severely injured trauma patients, StO$_2$ predicted mortality at least as well as lactate and base deficit (Cohn et al., 2007, *J. Trauma*, 62(1):44-54). In addition, it is recognized that patients are more likely to survive traumatic shock if their tissue oxygen delivery and consumption is maximized in the early post-resuscitative phase. Preservation of tissue perfusion during shock, as measured by StO$_2$ levels, was observed in animals treated with the ischemia/reperfusion protection composition relative to controls (FIG. 25). Higher StO$_2$ levels in animals treated with the ischemia/reperfusion protection composition indicate that there was more oxygen available to vital organs in the presence of the ischemia/reperfusion protection composition described herein, which generally leads to improved patient survival and outcome. In addition to higher StO$_2$ levels in animals treated with the ischemia/reperfusion protection composition, improved oxygen delivery was observed in pigs treated with ischemia/reperfusion protection composition relative to pigs treated with control solution (FIG. 26).

Figure 27:
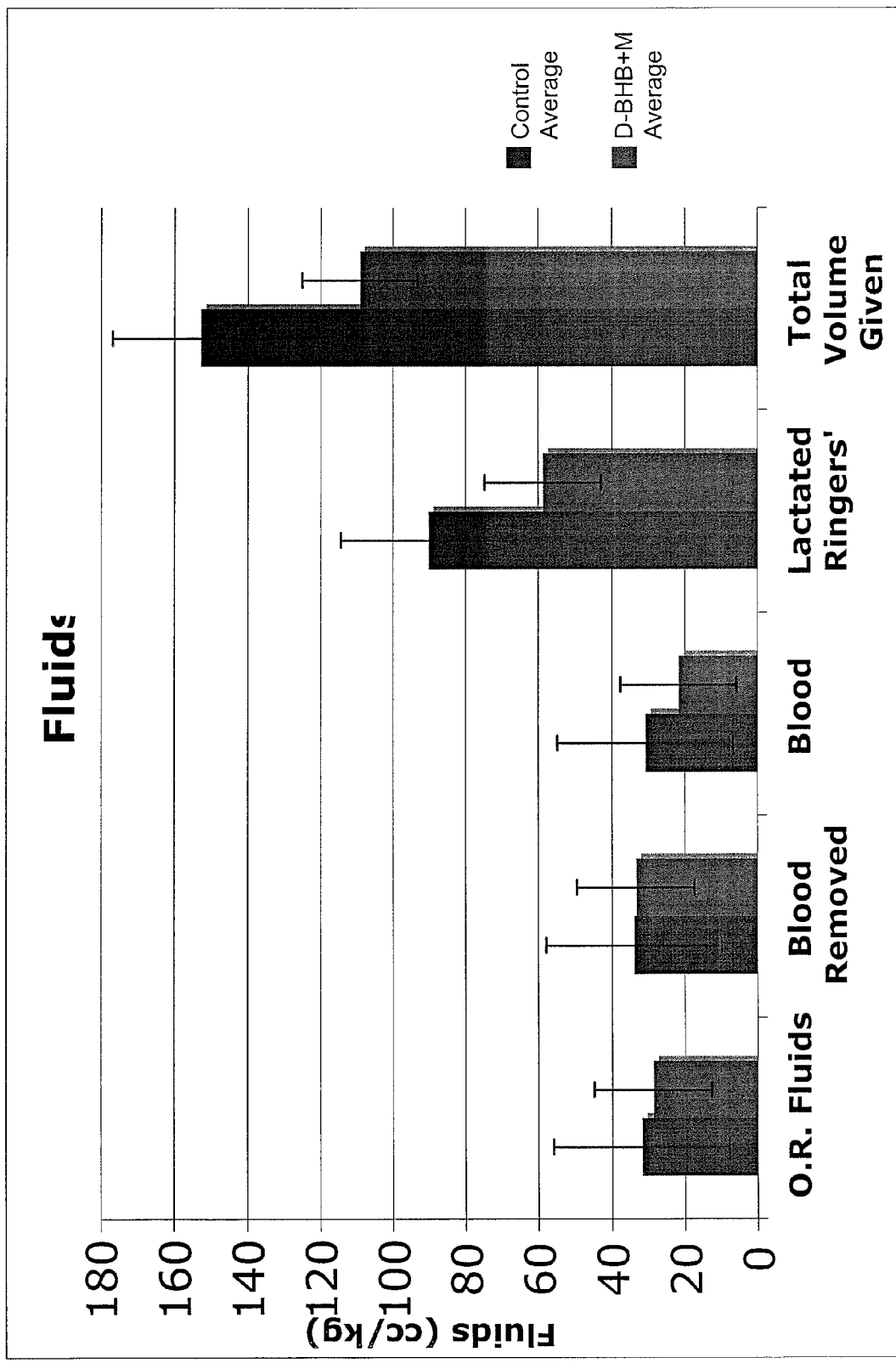
FIG. 27 is a graph plotting total volumes of blood removed and fluids administered to pigs that underwent hemorrhagic shock and were treated with ischemia/reperfusion protection composition or control solution.
Figure 28:
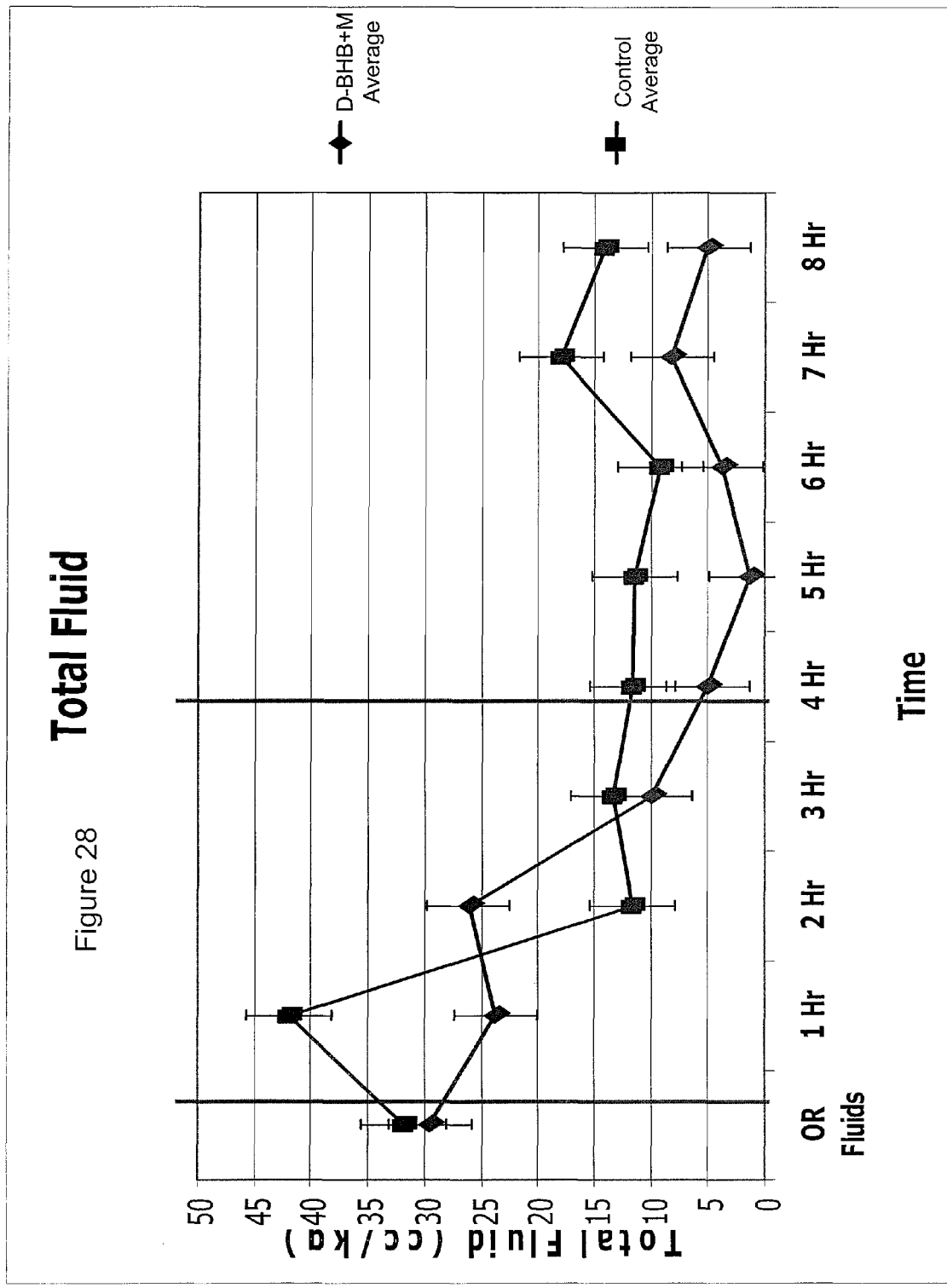
FIG. 28 is a graph plotting total fluids administered (cc/kg) at numerous time points to pigs that underwent hemorrhagic shock and were administered ischemia/reperfusion protection composition or control solution. OR Fluids—operating room fluids; 1 Hr, 2 Hr, 3 Hr, 4 Hr, 5 Hr, 6 Hr, 7 Hr, and 8 Hr=1, 2, 3, 4, 5, 6, 7, and 8 hours post resuscitation, respectively.

In addition to using multiple metrics to assess the success of tissue perfusion and return toward normal homeostasis in hemorrhagically shocked pigs treated with the ischemia/reperfusion protection composition or control solution, the volumes of fluid that needed to be administered during resuscitation also were measured (FIGS. 27 and 28). The total amount of fluid needed for resuscitation is an important parameter because aggressive fluid administration can lead to increased mortality. In particular, aggressive fluid administration that reverses hypotension before achieving hemostasis can dislodge partially formed clots and dilute existing clotting factors, resulting in further blood loss. Administration of ischemia/reperfusion protection composition was associated with a consistent trend toward lower volumes of fluid needed for resuscitation (FIG. 27). These results provide further evidence that administration of ischemia/reperfusion protection composition can reduce the mortality of individuals suffering from hemorrhagic shock.

Figure 29:
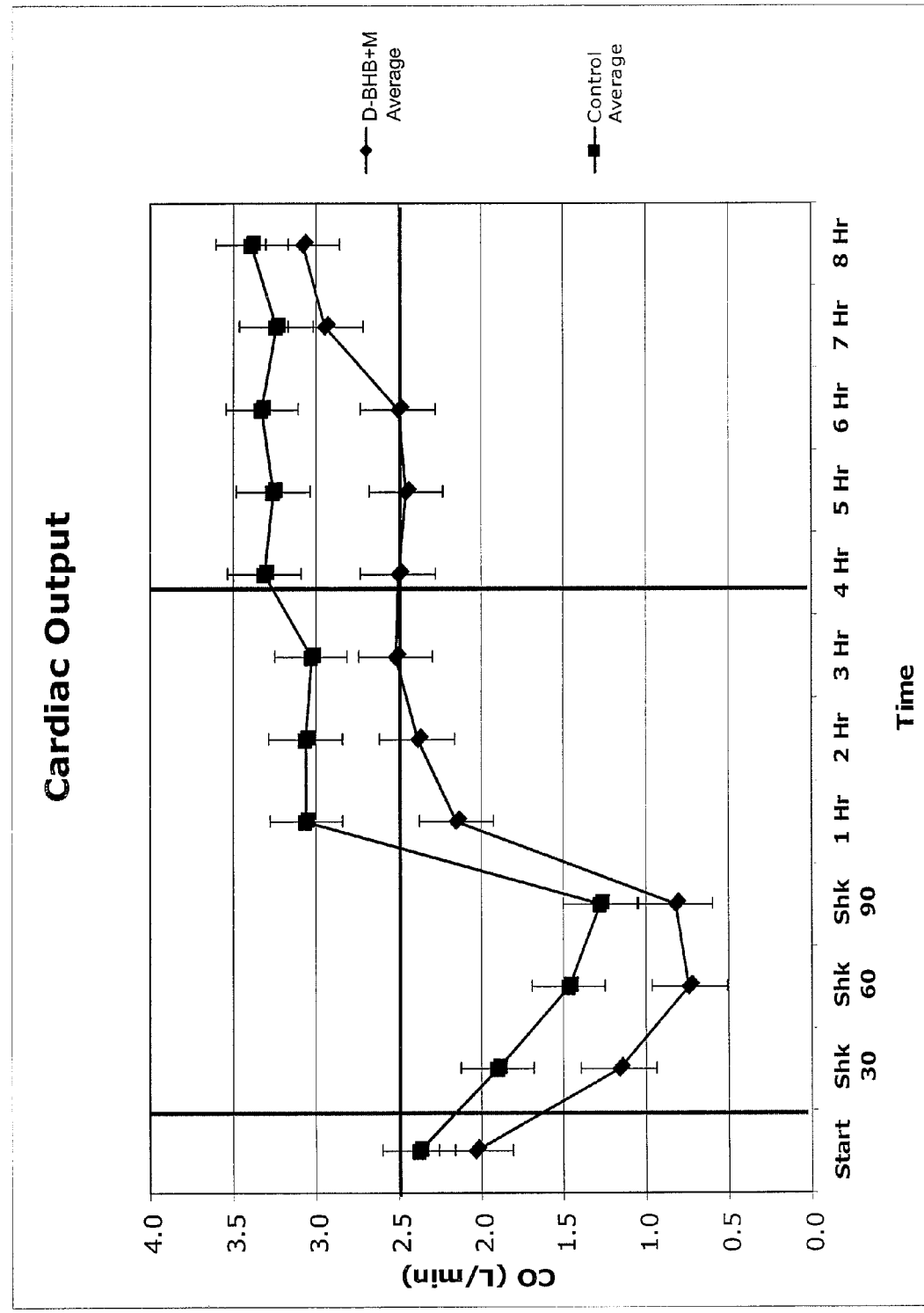
FIG. 29 is a graph plotting cardiac output (L/minute) at several time points in pigs that underwent hemorrhagic shock and were treated with ischemia/reperfusion protection composition or control solution. Start=time at which the hemorrhagic shock protocol was initiated; Shk 30, Shk 60, and Shk 90=30, 60, and 90 minutes after shock, respectively; 1 Hr, 2 Hr, 3 Hr, 4 Hr, 5 Hr, 6 Hr, 7 Hr, and 8 Hr=1, 2, 3, 4, 5, 6, 7, and 8 hours post-resuscitation, respectively.
Figure 30:
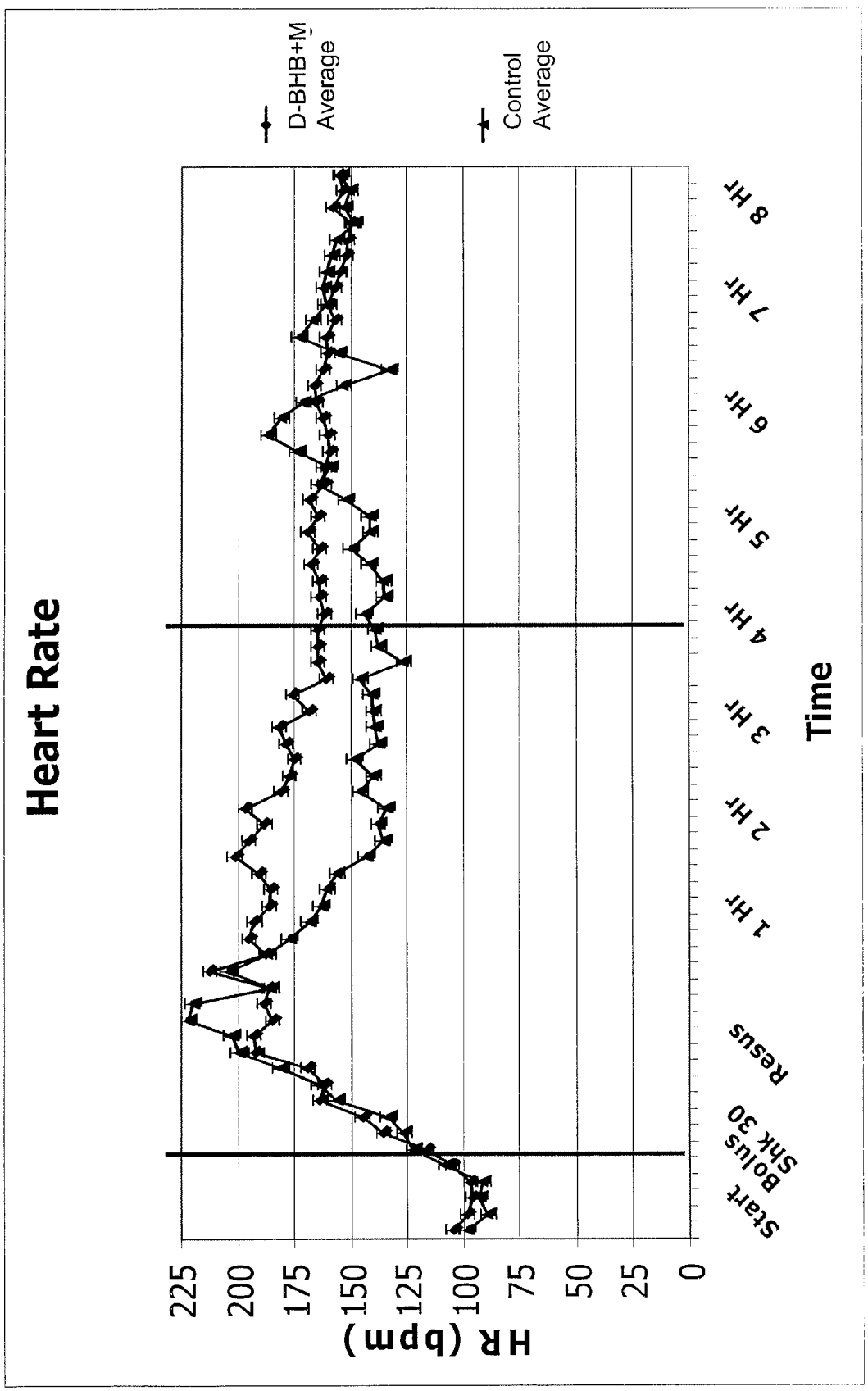
FIG. 30 is a graph plotting heart rate (beats/minute) at several time points in pigs that underwent hemorrhagic shock and were treated with ischemia/reperfusion protection composition or control solution. Start=the time at which the hemorrhagic shock protocol was initiated; Bolus=the time at which the bolus dose was administered; Shk 30=30 minutes after shock; Resus=resuscitation; 1 Hr, 2 Hr, 3 Hr, 4 Hr, 5 Hr, 6 Hr, 7 Hr, and 8 Hr=1, 2, 3, 4, 5, 6, 7, and 8 hours post-resuscitation, respectively. The left and right vertical lines indicate the start and stop, respectively, of infusion with ischemia/reperfusion protection composition or control solution.
Figure 31:
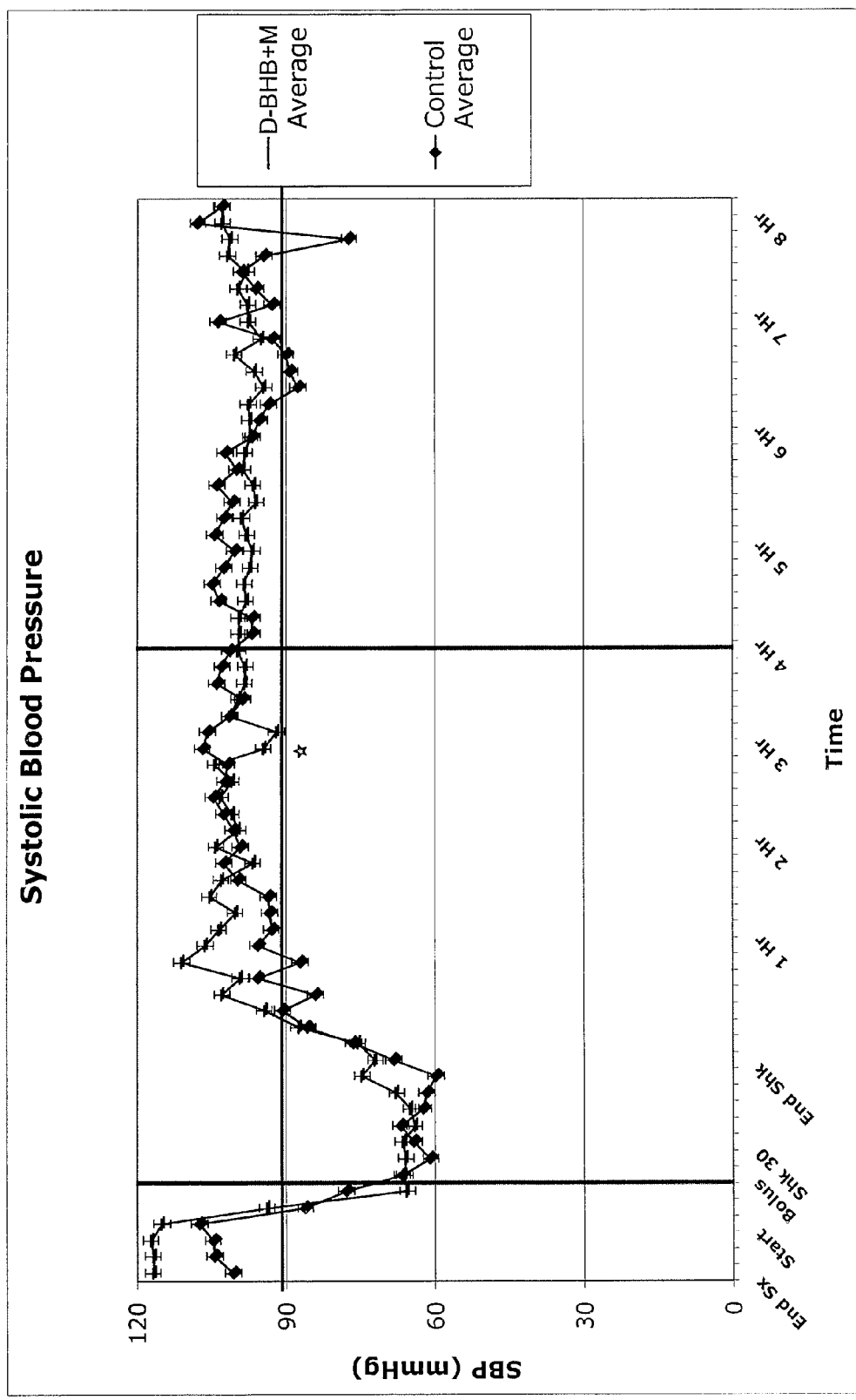
FIG. 31 is a graph plotting systolic blood pressure (mmHg) at numerous time points in pigs that underwent hemorrhagic shock and were treated with ischemia/reperfusion protection composition or control solution. End Sx=stabilization of animals prior to shock; Start=time at which the hemorrhagic shock protocol was initiated; Bolus=time at which bolus dose was administered; Shock 30=30 minutes after shock; End Shk=time at which shock ended; 1 Hr, 2 Hr, 3 Hr, 4 Hr, 5 Hr, 6 Hr, 7 Hr, and 8 Hr=1, 2, 3, 4, 5, 6, 7, and 8 hours post-resuscitation, respectively. The left and right vertical lines indicate the start and stop times, respectively, of infusion with ischemia/reperfusion protection composition or control solution.
Figure 32:
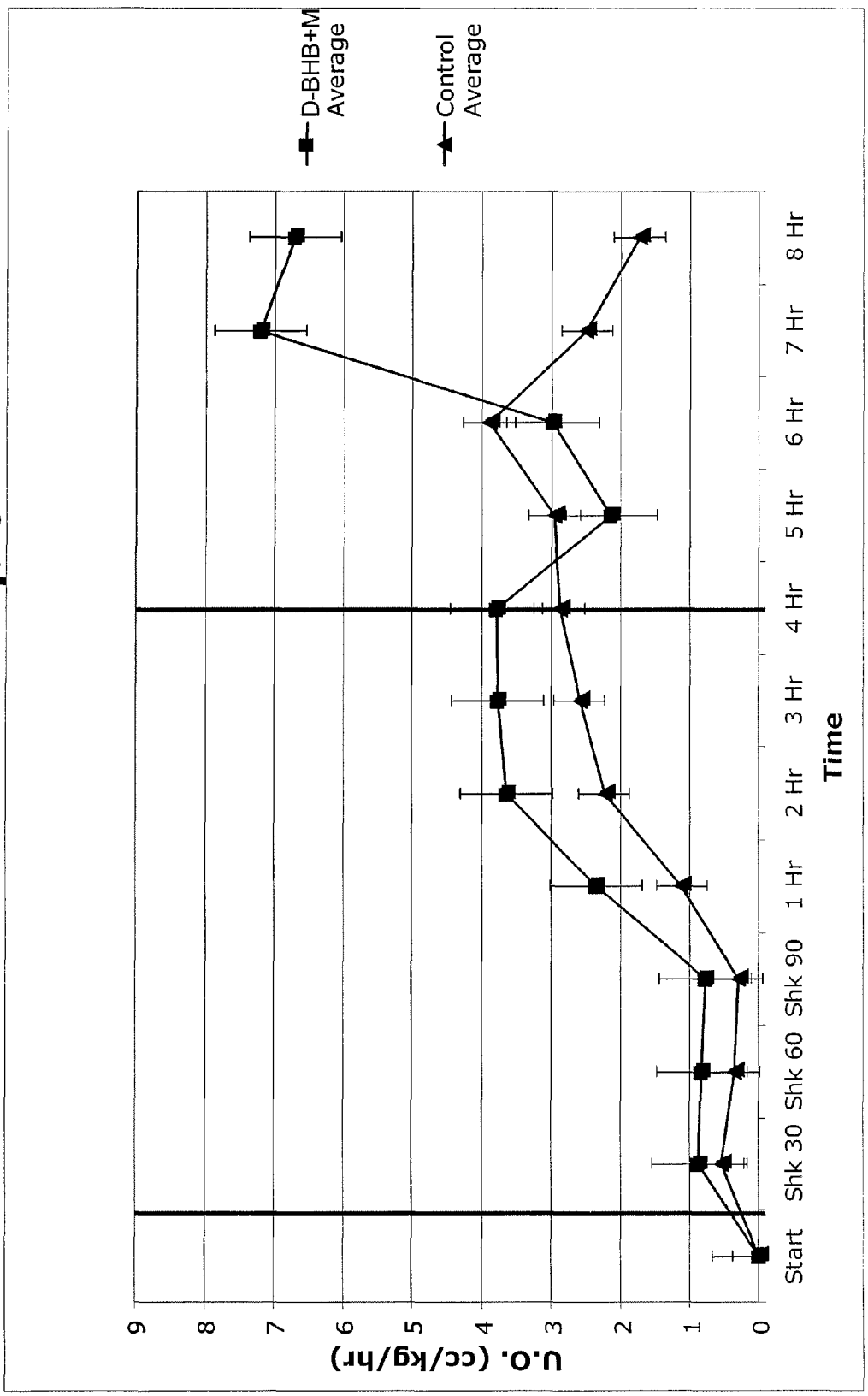
FIG. 32 is a graph plotting urine output (cc/kg/hour) measured at numerous time points in pigs that were subjected to hemorrhagic shock and treated with ischemia/reperfusion protection composition or control solution. Start=time at which the hemorrhagic shock protocol was initiated; Shk 30, Shk 60, and Shk 90=30, 60, and 90 minutes after shock, respectively; 1 Hr, 2 Hr, 3 Hr, 4 Hr, 5 Hr, 6 Hr, 7 Hr, and 8 Hr=1, 2, 3, 4, 5, 6, 7, and 8 hours post-resuscitation, respectively. The left and right vertical lines indicate the start and stop times, respectively, of infusion with ischemia/reperfusion protection composition or control solution.

Basic vital signs of cardiac output, heart rate, systolic blood pressure, and urine output also were monitored during the pig experiments, as they would be for human hemorrhagic shock patients. Lethal shock occurs when peripheral tissues have become so deprived of blood and oxygen that cellular energy levels are too low and toxic byproducts are too high. Under these conditions, the peripheral tissues can no longer maintain peripheral vasoconstriction in order to maintain blood flow to the brain and heart. This loss of vasoconstriction is frequently the final cause of death. In the control group, blood loss accompanied by peripheral loss of vasomotor tone resulted in a decrease in systolic blood pressure (FIG. 31) with subsequent compensatory increase in cardiac output (FIG. 28) in order to maintain brain and cardiac blood flow. Animals treated with the ischemia/reperfusion protection composition, however, appear to have maintained peripheral tissue vasoconstriction, which resulted in decreased cardiac output (FIG. 28) in the presence of increased heart rate (FIG. 29) and increased systolic blood pressure (FIG. 30) compared to controls. In addition, renal output more rapidly recovered in pigs treated with the ischemia/reperfusion protection composition (FIG. 32). Urine output is an indicator of kidney function, which in turn is determined by blood flow to the kidneys and the integrity of the kidney cells. These results indicate that the ischemia/reperfusion protection compositions described herein can promote the viability of peripheral tissues by providing a more efficient energy supply and counteracting the build up of toxic by-products.

Treating animals with ischemia/reperfusion protection composition prevented intra-abdominal compartment syndrome (IACS), further demonstrating the beneficial effects of the ischemia/reperfusion protection composition in supplying tissues with energy and maintaining cellular integrity. IACS is a syndrome involving rapid swelling of the abdomen that can develop during resuscitation of trauma patients and that is a harbinger of pending death. While two pigs that received a low dose of ischemia/reperfusion protection composition died prior to definitive resuscitation, none of the pigs treated with the ischemia/reperfusion protection composition developed IACS. In the control group, on the other hand, an animal died due to IACS at 4.5 hours after resuscitation began. Table 4 shows the number of pigs that lived and died in each of the groups that were subjected to hemorrhagic shock and administered a control solution or the low, medium and high dosing of the ischemia/reperfusion protection composition as described herein.

TABLE 4

Pig Mortality

| Dosing (n = 16) | | Control | | D-BHB + M | |
|---|---|---|---|---|---|
| | | Lived | Died | Lived | Died |
| Low: | bolus + interval 1x infusion | 2 | 1 | 2 | 2 |
| Medium: | bolus − interval 1x infusion | 1 | 0 | 2 | 0 |
| High: | bolus − interval 2x infusion | 2 | 0 | 4 | 0 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating ischemic damage and/or reperfusion injury in an individual who is experiencing or has experienced hemorrhagic external blood loss, comprising administering a composition comprising 4M D-beta-hydroxybutyrate and 43 mM melatonin to said individual, thereby treating ischemic damage and/or reperfusion injury in said individual.

2. The method of claim 1, wherein the individual is experiencing or has experienced a major hemorrhagic event.

3. The method of claim 1, wherein said individual has lost a blood volume of at least about 10%.

4. The method of claim 1, wherein said blood loss in said individual results in a systolic blood pressure of about 70 mm Hg or less.

5. The method of claim 1, wherein said composition is administered at a volume of 0.3 to 2 milliliters (mls) per kilogram (kg) of weight of said individual.

6. The method of claim 1, wherein said composition is administered at a volume of 0.3 to 2 mls per kg of weight of said individual per hour.

7. The method of claim 1, wherein said composition is administered at a volume of 0.3 to 2 mls per kg of weight of said individual followed by administration of said composition at a volume of 0.3 to 2 mls per kg of weight of said individual per hour.

8. The method of claim 1, wherein said composition is administered intravenously or intraosseously.

9. The method of claim 1, wherein said individual's StO2 levels are less than 75%.

10. The method of claim 9, wherein said administering results in said individual's StO2 levels returning to greater than 75%.

11. The method of claim 1, wherein said individual has been treated when the individual's StO2 levels are greater than 75%.

12. The method of claim 1, wherein said individual's lactate levels are greater than 2.1 mg/dl.

13. The method of claim 12, wherein said administering results in said individuals lactate levels returning to less than 2.1 mg/dl.

14. The method of claim 1, wherein said individual has been treated when the individual's lactate levels are less than 2.1 mg/dl.

15. The method of claim 1, wherein said administering prevents the base deficit of said individual from reaching 6 mEq/L.

16. The method of claim 1, further comprising transfusing said individual with blood or plasma after said composition is administered.

* * * * *

UNITED STATES PATENT AND TRADEMARK OFFICE
CERTIFICATE OF CORRECTION

| | | |
|---|---|---|
| PATENT NO. | : 9,186,340 B2 | Page 1 of 1 |
| APPLICATION NO. | : 12/595586 | |
| DATED | : November 17, 2015 | |
| INVENTOR(S) | : Matthew T. Andrews et al. | |

It is certified that error appears in the above-identified patent and that said Letters Patent is hereby corrected as shown below:

IN THE SPECIFICATION

Column 1, Lines 19-22, please delete:

"The U.S. Government has certain rights in the invention pursuant to Grant Nos. W911NF-05-1-0432 and W911NF-06-1-0088 awarded by the Defense Advanced Research Projects Agency (DARPA)."

and insert, therefor:

-- This invention was made with government support under W911NF-05-1-0432, W911NF-06-1-0088, and DAAD19-01-1-0014 awarded by the Army, and NS037764 awarded by the National Institutes of Health. The government has certain rights in the invention. --

Signed and Sealed this
Twenty-ninth Day of March, 2016

Michelle K. Lee
*Director of the United States Patent and Trademark Office*